United States Patent
Priestley

(10) Patent No.: US 6,846,806 B2
(45) Date of Patent: Jan. 25, 2005

(54) PEPTIDE INHIBITORS OF HEPATITIS C VIRUS NS3 PROTEIN

(75) Inventor: E. Scott Priestley, Hockessin, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 392 days.

(21) Appl. No.: 10/039,317

(22) Filed: Oct. 23, 2001

(65) Prior Publication Data

US 2002/0177725 A1 Nov. 28, 2002

Related U.S. Application Data

(60) Provisional application No. 60/242,557, filed on Oct. 23, 2000.

(51) Int. Cl.$^7$ .............................................. A61K 38/00
(52) U.S. Cl. ......................................................... 514/18
(58) Field of Search ........................................... 514/18

(56) References Cited

FOREIGN PATENT DOCUMENTS

| | | |
|---|---|---|
| WO | WO 97/43310 | 11/1997 |
| WO | WO 98/17679 | 4/1998 |
| WO | WO 98/22496 | 5/1998 |
| WO | WO 98/46630 | 10/1998 |
| WO | WO 99/07733 | 2/1999 |
| WO | WO 99/07734 | 2/1999 |
| WO | WO 99/50230 | 10/1999 |
| WO | WO 00/09543 | 2/2000 |
| WO | WO 00/09558 | 2/2000 |

OTHER PUBLICATIONS

Benet et al. Pharmacokinetics: The dynamics of Drug Absorption, Distribution, adn Elimination. McGraw–Hill (1990): 3–32.*

Manning et al. Stability of Protein Pharmaceuticals. Pharmaceutical Research (1989) 6: 903–918.*

Dimasi et al. Characterization of engineered hepatitis C virus NS3 protease inhibitors affinity selected from human pancreatic secretory trypsin inhibitor and minibody repertoires. J Virol. 1997 Oct; 71(10):7461–9.*

C. Steinkuhler, et al, "Product Inhibition of the Hepatitis C Virus NS3 Protease," Biochemistry, 37, pp. 8899–8905, 1998.

P. Ingallinella, et al, "Potent Peptide Inhibitors of Human Hepatitis C Virus NS3 Protease Are Obtained by Optimizing the Cleavage Products," Biochemistry, 37, pp. 8906–8914, 1998.

E. Pizzi, et al, "Molecular Model of the Specificity Pocket of the Hepatitis C Virus Protease: Implications for Substrate Recognition," Proc. Natl. Acad. Sci. USA, 91, pp. 888–892, 1994.

A. Urbani, et al, "Substrate Specificity of the Hepatitis C Virus Serine Protease NS3," The Journal of Biological Chemistry, 272(14), pp. 9204–9209, 1997.

R. B. Perni, "NS3•4A Protease as a Target for Interfering with Hepatitis C Virus Replication," Drug News Perspect, 13(2), pp. 69–77, 2000.

* cited by examiner

Primary Examiner—Christopher R. Tate
Assistant Examiner—Maury A. Audet
(74) Attorney, Agent, or Firm—James Epperson; Scott K. Larsen

(57) ABSTRACT

This invention relates to a novel class of peptides having the Formula (I):

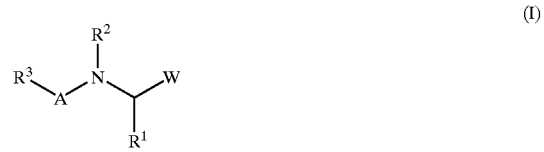

(I)

which are useful as serine protease inhibitors, and more particularly as Hepatitis C virus(HCV) NS3 protease inhibitors. This invention also relates to pharmaceutical compositions comprising these compounds and methods of using the same in the treatment of HCV infection.

1 Claim, No Drawings

PEPTIDE INHIBITORS OF HEPATITIS C VIRUS NS3 PROTEIN

FIELD OF THE INVENTION

The present invention relates generally to a novel class of peptides, which are useful as serine protease inhibitors, and more particularly as Hepatitis C virus (HCV) NS3 protease inhibitors. This invention also relates to pharmaceutical compositions comprising these compounds and methods of using the same in the treatment of HCV infection.

BACKGROUND OF THE INVENTION

Hepatitis C virus is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chronicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard, T. et al. *Lancet* (1998), 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus, agents that inhibit NS3 proteolytic processing of the viral polyprotein are expected to have antiviral activity.

Extensive efforts toward the development of HCV NS3 protease inhibitors have resulted in the following disclosures: WO 98/17679 (Tung et al.) describes a large class of generic peptide and peptidomimetic inhibitors with the following formula: $U-E^8-E^7-E^6-E^5-E^4-NH-CH(CH_2G^1)-W^1$, wherein $W^1$ is a variety of electrophilic groups. E4 represents either an amino acid or one of a series of peptidomimetic groups. No example of compounds wherein $W^1$ is boronic acid or ester is disclosed or enabled in WO 98/17679. Additionally, compounds with extended aralkyl or heteroaralkyl P1 substituents as disclosed in the present application are not disclosed, enabled or exemplified in WO 98/17679.

WO 98/22496 (Attwood et al.) discloses solely hexapeptide inhibitors of the following general formula: $R^9-NH-CH(R^8)-CO-NH-CH(R^7)-CO-N(R^6)-CH(R^5)-CO-NH-CH(R^4)-CO-N(R^3)-CH(R^2)-CO-NH-CH(R^1)-E$ wherein E is either an aldehyde or a boronic acid. Compounds with extended aralkyl or heteroaralkyl P1 substituents as disclosed in the present application are not specifically disclosed, enabled or exemplified in WO 98/22496.

WO 99/07734 (Llinas-Brunet et al.) discloses tetra- to hexa-peptide analogs containing a $P_1$ electrophilic carbonyl group, a phosphonate ester, or an aza-aminoacid analog. WO 99/07733 (Llinas-Brunet et al.) describes related peptides terminating in a carboxylate. Similar compounds are reported by Steinkuhler et al. *Biochemistry* (1998), 37, 8899–8905 and Ingallinella et al. *Biochemistry* (1998), 37, 8906–8914. None of these publiscations teaches the making and use of compounds with aralkyl or heteroaralkyl P1 substituents.

WO 99/50230 (Tung et al.) discloses peptidomimetics containing a 5 or 6-membered carbocyclic ring at the P2 position. Tung et al. does not teach the aralkyl or heteroaralkyl P1 substituents of the present invention.

WO 00/09543 (Llinas-Brunet et al.) discloses tripeptides containing a substituted proline residue at P2 and an aminocyclopropanecarboxylate derivative at P1. A related disclosure, WO 00/09558 (Llinas-Brunet et al.), discloses tetra- to hexapeptides with the same P1 and P2 structure as WO 00/09543.

Other peptide inhibitors of HCV protease have been disclosed. WO 98/46630 (Hart et al.) has described heptapeptide analogs containing an ester linkage at the scissile bond. WO 97/43310 (Zhang et al.) discloses high molecular weight peptide inhibitors. The present invention is distinct from the compounds of WO 98/46630 or WO 97/43310.

Additionally, literature regarding HCV NS3 protease inhibitors suggest that the S1 pocket of the NS3 protease enzyme can only accommodate small aliphatic P1 residues. (Pizzi et al. *Proc. Natl. Acad. Sci. USA* (1994), 91, 888–892; Urbani et al. *J. Biol. Chem.* (1997) 272, 9204–9209; Perni, Robert B. *Drug News Perspective* (2000), 13, 69–77). Thus, the general literature regarding HCV NS3 protease inhibitors does not suggest or provide the motivation to one skilled in the art to make extended aralkyl P1 inhibitors of the present invention.

Based on the large number of persons currently infected with HCV and the limited treatments available, it is desirable to discover new inhibitors of HCV NS3 protease. The instant invention discloses a class of novel peptides with extended P1 residues that exhibit inhibitory activity against HCV NS3 protease. Further, the present invention discloses unexpected benefit of HCV NS3 protease inhibitory selectivity over inhibition of elastase and/or chymotrypsin.

SUMMARY OF THE INVENTION

One object of the present invention is to provide compounds, or pharmaceutically acceptable salt forms or prodrugs thereof, which are useful as inhibitors of hepatitis C virus protease, more specifically, the NS3 protease.

It is another object of the present invention to provide pharmaceutical compositions comprising a pharmaceutically acceptable carrier and a therapeutically effective amount of a compound of Formula (I), or pharmaceutically acceptable salt form or prodrug thereof.

It is another object of the present invention to provide a method for the treatment or prevention of HCV comprising administering to a host in need of such treatment a therapeutically effective amount of a compound of Formula (I), or a pharmaceutically acceptable salt form or prodrug thereof.

These and other objects of the invention, which will become apparent during the following detailed description, have been achieved by the discovery that compounds of Formula (I):

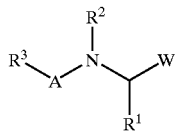

(I)

Or pharmaceutically acceptable salt forms or prodrugs thereof, wherein $R^1$, $R^2$, $R^3$, W, and A are defined below, are effective inhibitors of HCV NS3 protease.

DETAILED DESCRIPTION OF THE INVENTION

[1] Thus, in one embodiment, the present invention provides a compound of Formula (I):

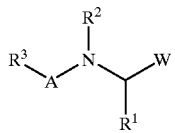

(I)

or a pharmaceutically acceptable salt form or prodrug thereof, wherein:

W is selected from the group:
—$B(Y^1)(Y^2)$,
—$C(=O)C(=O)$—Q,
—$C(=O)C(=O)NH$—Q,
—$C(=O)C(=O)$—O—Q,
—$C(=O)CF_2C(=O)NH$—Q;
—$C(=O)CF_3$,
—$C(=O)CF_2CF_3$, and
—$C(=O)H$;

$Y^1$ and $Y^2$ are independently selected from:
a) —OH,
b) —F,
c) —$NR^4R^5$,
d) $C_1$–$C_8$ alkoxy, and when taken together with B, $Y^1$ and $Y^2$ form:
e) a cyclic boronic ester where said cyclic boronic ester contains from 2 to 20 carbon atoms, and, optionally, 1, 2, or 3 heteroatoms which can be N, S, or O;
f) a cyclic boronic amide where said cyclic boronic amide contains from 2 to 20 carbon atoms and, optionally, 1, 2, or 3 heteroatoms which can be N, S, or O; or
g) a cyclic boronic amide-ester where said cyclic boronic amide-ester contains from 2 to 20 carbon atoms and, optionally, 1, 2, or 3 heteroatoms which can be N, S, or O;

Q is selected from —$(CR^6R^{6c})_p$—$Q^1$, —$(CR^6R^{6c})_p$—$Q^2$, $C_2$–$C_4$ alkenyl substituted with $Q^1$, $C_2$–$C_4$ alkynyl substituted with $Q^1$, and an amino acid residue;

p is 1, 2, 3 or 4;

$Q^1$ is selected from the group:
—$CO_2R^7$, —$SO_2R^7$, —$SO_3R^7$, —$P(O)_2R^7$, —$P(O)_3R^7$, aryl substituted with 0–4 $Q^{1a}$, and 5–6 membered heterocyclic ring system consisting of carbon atoms and 1–4 heteroatoms selected from the group: O, S, and N; optionally saturated, partially unsaturated or unsaturated; and said 5–6 membered heterocyclic ring system is substituted with 0–4 $Q^{1a}$;

$Q^{1a}$ is H, F, Cl, Br, I, —$NO_2$, —CN, —NCS, —$CF_3$, —$OCF_3$, —$CO_2R^8$, —$C(=O)NR^8R^9$, —$NHC(=O)R^8$, —$SO_2R^8$, —$SO_2NR^8R^9$, —$NR^8R^9$, —$OR^8$, —$SR^8$, $C_1$–$C_4$ alkyl, $C_1$–$C_4$ haloalkyl, or $C_1$–$C_4$ haloalkoxy;

$Q^2$ is —$X^1$—$NR^{10}$—Z, —$NR^{10}$—$X^2$—Z, or —$X^1$—$NR^{10}$—$X^2$—Z;

$X^1$ and $X^2$ are independently selected from: —$C(=O)$—, —S—, —$S(=O)$—, —$S(=O)_2$—, —$P(O)$—, —$P(O)_2$—, and —$P(O)_3$—;

Z is $C_1$–$C_4$ haloalkyl,
$C_1$–$C_4$ alkyl substituted with 0–3 $Z^a$,
$C_2$–$C_4$ alkenyl substituted with 0–3 $Z^a$,
$C_2$–$C_4$ alkynyl substituted with 0–3 $Z^a$,
$C_3$–$C_{10}$ cycloalkyl substituted with 0–5 $Z^b$,
$C_3$–$C_{10}$ carbocyle substituted with 0–5 $Z^b$,
6–10 membered aryl substituted with 0–5 $Z^b$, or
5–10 membered heterocyclic ring system consisting of carbon atoms and 1–4 heteroatoms selected from the group: O, S, and N; optionally saturated, partially unsaturated or unsaturated; and said 5–10 membered heterocyclic ring system is substituted with 0–4 $Z^b$;

$Z^a$ is H, F, Cl, Br, I, —$NO_2$, —CN, —NCS, —$CF_3$, —$OCF_3$, —$CO_2R^8$, —$C(=O)NR^8R^9$, —$NHC(=O)R^8$, —$NR^8R^9$, —$OR^8$, —$SR^8$, —$S(=O)R^8$, —$SO_2R^8$, —$SO_2NR^8R^9$,
$C_1$–$C_4$ alkyl,
$C_1$–$C_4$ haloalkyl, $C_1$–$C_4$ haloalkoxy,
$C_3$–$C_7$ cycloalkyl substituted with 0–5 $Z^b$,
$C_3$–$C_{10}$ carbocyle substituted with 0–5 $Z^b$,
6–10 membered aryl substituted with 0–5 $Z^b$, or
5–10 membered heterocyclic ring system consisting of carbon atoms and 1–4 heteroatoms selected from the group: O, S, and N; optionally saturated, partially unsaturated or unsaturated; and said 5–10 membered heterocyclic ring system is substituted with 0–4 $Z^b$;

$Z^b$ is H, F, Cl, Br, I, $-NO_2$, $-CN$, $-NCS$, $-CF_3$, $-OCF_3$, $-CO_2R^8$, $-C(=O)NR^8R^9$, $-NHC(=O)R^8$, $-NR^8R^9$, $-OR^8$, $-SR^8$, $-S(=O)R^8$, $-SO_2R^8$, $-SO_2NR^8R^9$, $C_1-C_4$ alkyl, $C_1-C_4$ haloalkyl, $C_1-C_4$ haloalkoxy, $C_3-C_7$ cycloalkyl substituted with 0–5 $Z^c$, $C_3-C_{10}$ carbocycle substituted with 0–5 $Z^c$, 6–10 membered aryl substituted with 0–5 $Z^c$, or 5–10 membered heterocyclic ring system consisting of carbon atoms and 1–4 heteroatoms selected from the group: O, S, and N; optionally saturated, partially unsaturated or unsaturated; and said 5–10 membered heterocyclic ring system is substituted with 0–4 $Z^c$;

$Z^c$ is H, F, Cl, Br, I, $-NO_2$, $-CN$, $-NCS$, $-CF_3$, $-OCF_3$, $-CO_2R^8$, $-C(=O)NR^8R^9$, $-NHC(=O)R^8$, $-NR^8R^9$, $-OR^8$, $-SR^8$, $-S(=O)R^8$, $-SO_2R^8$, $-SO_2NR^8R^9$, $C_1-C_4$ alkyl, $C_1-C_4$ haloalkyl, or $C_1-C_4$ haloalkoxy;

A is $A^2-A^3$, $A^2-A^3-A^4$, $A^2-A^3-A^4-A^5$, $A^2-A^3-A^4-A^5-A^6$, or $A^2-A^3-A^4-A^5-A^6-A^7$;

$A^2$ is a natural amino acid, a modified amino acid, an unnatural amino acid, or

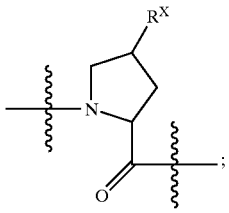

wherein said amino acid is of either D or L configuration;

$R^x$ is H, F, Cl, Br, I, $-CF_3$, $-OCF_3$, $-(CH_2)_m-R^{16}-(CH_2)_n-R^{12}$, or $-CO_2R^{12}$;

m and n are independently selected from 0, 1, 2, and 3;

$A^3$, $A^4$, $A^5$, $A^6$, and $A^7$ are independently selected from an amino acid residue; wherein said amino acid residue, at each occurence, is independently selected from a natural amino acid, a modified amino acid, or an unnatural amino acid; wherein said natural, modified or unnatural amino acid is of either D or L configuration;

$R^1$ is $-CH_2CH_2-R^{1a}$, $-CH_2CH_2CH_2-R^{1a}$, $-CH_2CH_2CH_2CH_2-R^{1a}$, $-CH_2CH_2CH_2CH_2CH_2-R^{1a}$, $-CH_2CH_2CH_2CH_2CH_2CH_2-R^{1a}$, $-CH_2CH_2CH_2CH_2CH_3$, $-CH_2CH_2CH_2CH_2CH_2CH_3$, $-CH_2CH_2CH_2C(CH_3)_2$, $-CH_2CH_2CH_2C(CH_2CH_3)_2$, or $-CH_2CH_2CH_2$-cyclobutyl;

$R^{1a}$ is

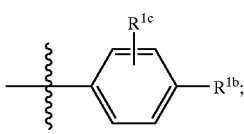

$R^{1b}$ is selected at each occurrence from the group: H, $C_1-C_4$ alkyl, F, Cl, Br, I, $-OH$, $C_1-C_4$ alkoxy, phenoxy, benzyloxy, $-SH$, $-CN$, $-NO_2$, $-C(=O)OR^{1d}$, $-NR^{1d}R^{1d}$, $-CF_3$, $-OCF_3$, $C_3-C_6$ cycloalkyl, and aryl substituted by 0–3 $R^{1c}$;

$R^{1c}$ is selected at each occurrence from the group: methyl, ethyl, Cl, F, Br, I, OH, methoxy, ethoxy, $-CN$, $-NO_2$, $-C(=O)OR^{1d}$, $NR^{1d}R^{1d}$, $-CF_3$, and $-OCF_3$;

$R^{1d}$ is H, $C_1-C_4$ alkyl, phenyl or benzyl;

$R^2$ is H, $C_1-C_4$ alkyl, aryl, aryl($C_1-C_4$ alkyl)-, or $C_3-C_6$ cycloalkyl;

$R^3$ is H, $C_1-C_4$ alkyl, aryl, aryl($C_1-C_4$ alkyl)-, $-C(=O)R^{11}$, $-CO_2R^{11}$, $-C(=O)NHR^{11}$, $-S(=O)R^{11}$, $-S(=O)_2R^{11}$, or an $NH_2$-blocking group;

$R^4$ and $R^5$, are independently selected from: H, $C_1-C_4$ alkyl, aryl($C_1-C_4$ alkyl)-, and $C_3-C_7$ cycloalkyl;

$R^6$ is selected from the group: H, $-CO_2R^7$, $-NR^7R^7$, and $C_1-C_6$ alkyl substituted with 0–1 $R^{6a}$;

$R^{6a}$ is selected from the group: halo, $-NO_2$, $-CN$, $-CF_3$, $-CO_2R^7$, $-NR^7R^7$, $-OR^7$, $-SR^7$, $-C(=NH)NH_2$, and aryl substituted with 0–1 $R^{6b}$;

$R^{6b}$ is selected from the group: $-CO_2H$, $-NH_2$, $-OH$, $-SH$, and $-C(=NH)NH_2$;

$R^{6c}$ is H or $C_1-C_4$ alkyl;

$R^7$ at each occurrence is independently selected from the group: H, $C_1-C_4$ alkyl, aryl, and aryl($C_1-C_4$ alkyl)-, wherein aryl is optionally substituted with 0–3 substituents selected from $-CH_3$, $-NO_2$, $-CN$, $-OH$, $-OCH_3$, $-SO_2CH_3$, $-CF_3$, Cl, Br, I, and F;

alternatively, $-NR^7R^7$ may optionally form a 5–6 membered heterocycle consisting of carbon atoms, a nitrogen atom, and optionally a second heteroatom selected from the group: O, S, and N;

$R^8$ and $R^9$ are independently selected from H, $C_1-C_4$ alkyl, aryl, aryl($C_1-C_4$ alkyl)-, and $C_3-C_7$ cycloalkyl;

alternatively, $NR^8R^9$ may form a 5–6 membered heterocycle consisting of carbon atoms, a nitrogen atom, and optionally a second heteroatom selected from the group: O, S, and N;

$R^{10}$ is selected from the group: H, $C_1-C_4$ alkyl substituted with 0–3 $R^{13}$, $C_3-C_{10}$ carbocycle substituted with 0–3 $R^{13}$, 6–10 membered aryl substituted with 0–3 $R^{13}$, and 5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–3 $R^{13}$;

$R^{11}$ is $C_1-C_4$ alkyl substituted with 0–1 $R^{11a}$,

6–10 membered aryl substituted with 0–2 $R^{11b}$, or

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{11b}$;

$R^{11a}$ is $C_1-C_4$ alkyl, halogen, $-OR^{14}$, $-SR^{14}$, $-NR^{14}R^{15}$, aryl, or a 5–6 membered heterocyclic ring system containing 1, 2 or 3 heteroatoms selected from nitrogen, oxygen and sulfur;

$R^{11b}$ is $-NO_2$, $-NH_2$, $-SO_3H$, $-SO_2CH_3$, $-CO_2H$, $-CF_3$, $-OH$, $-SH$, $-OCF_3$, Cl, Br, I, F, $=O$, $C_1-C_4$ alkyl, $C_1-C_4$ alkoxy, $C_1-C_4$ thioalkoxy, aryl, or aryl ($C_1-C_4$ alkyl)-, wherein aryl is optionally substituted with 0–3 substituents selected from $-CH_3$, $-NO_2$, $-CN$, $-OH$, $-OCH_3$, $-SO_2CH_3$, $-CF_3$, Cl, Br, I, and F;

$R^{12}$ is selected from the group: H;

$C_1-C_6$ alkyl substituted with 0–3 $R^{12a}$;

$C_2-C_6$ alkenyl substituted with 0–3 $R^{12a}$;

$C_2-C_6$ alkynyl substituted with 0–3 $R^{12a}$;

$C_3-C_7$ cycloalkyl substituted with 0–3 $R^{12a}$;

$C_4-C_{10}$ (cycloalkyl-alkyl) substituted with 0–3 $R^{12a}$;

6–10 membered aryl substituted with 0–3 $R^{12a}$; and

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: $C_1$–$C_6$ alkoxy; lower thioalkyl; sulfonyl; —$NO_2$; halogen; haloalkyl; carboxyl; carboxy(lower alkyl); —$OR^{14}$; —$SR^{14}$; —$NR^{14}R^{15}$; —C(=O)$NR^{14}R^{15}$; —$NR^{14}$C(=O) $R^{15}$; —S(=O)$_2R^{14}$;

$C_1$–$C_6$ alkyl substituted with 0–3 $R^{12b}$;

$C_2$–$C_6$ alkenyl substituted with 0–3 $R^{12b}$;

$C_2$–$C_6$ alkynyl substituted with 0–3 $R^{12b}$;

$C_3$–$C_7$ cycloalkyl substituted with 0–3 $R^{12b}$;

$C_4$–$C_{10}$ (alkylcycloalkyl) substituted with 0–3 $R^{12b}$;

6–10 membered aryl substituted with 0–3 $R^{12b}$; and

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12b}$;

$R^{12b}$ is independently selected from the group: $C_1$–$C_6$ alkyl; $C_3$–$C_7$ cycloalkyl; $C_1$–$C_6$ alkoxy; halogen; —$OR^{14}$; —$SR^{14}$; —$NR^{14}R^{15}$; —C(=O)$NR^{14}R^{15}$; —$NR^{14}$C(=O) $R^{15}$; —S(=O)$_2R^{14}$; —$NO_2$; haloalkyl; carboxyl; carboxy (lower alkyl); aryl;

and 5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with $C_1$–$C_6$ alkyl;

$R^{13}$ at each occurrence is independently selected from the group: H, —$NO_2$, —$SO_2OH$, —$SO_2CH_3$, —$CF_3$, Cl, Br, I, F, —$NH_2$, —NH($CH_3$), —N($CH_3$)$_2$, —NH($CH_2CH_3$), —N($CH_2CH_3$)$_2$, and $C_1$–$C_4$ alkyl;

$R^{14}$ and $R^{15}$ are independently selected from the group: H, $C_1$–$C_4$ alkyl, aryl, aryl($C_1$–$C_4$ alkyl)-, and $C_3$–$C_7$ cycloalkyl;

$R^{16}$ is a bond, —O—, —S— or —$NR^{17}$—; and $R^{17}$ is H, $C_1$–$C_4$ alkyl, aryl, aryl($C_1$–$C_4$ alkyl)-, or $C_3$–$C_6$ cycloalkyl.

[2] In another embodiment, the present invention provides a compound of Formula (I) or a pharmaceutically acceptable salt or prodrug thereof, wherein:

W is —B($Y^1$)($Y^2$) or —C(=O)C(=O)NH—Q;

$Y^1$ and $Y^2$ are independently selected from:

a) —OH, b) —F, c) —$NR^4R^5$, d) $C_1$–$C_8$ alkoxy, and when taken together with B, $Y^1$ and $Y^2$ form:

e) a cyclic boronic ester where said cyclic boronic ester contains from 2 to 20 carbon atoms, and, optionally, 1, 2, or 3 heteroatoms which can be N, S, or O;

Q is selected from —(C$R^6R^{6c}$)$_p$—$Q^1$, $C_2$–$C_4$ alkenyl substituted with $Q^1$, $C_2$–$C_4$ alkynyl substituted with $Q^1$, and an amino acid residue;

p is 1, 2 or 3;

$Q^1$ is selected from the group:

—$CO_2R^7$, —$SO_2R^7$, —$SO_3R^7$, aryl substituted with 0–4 $Q^{1a}$, and

5–6 membered heterocyclic ring system consisting of carbon atoms and 1–4 heteroatoms selected from the group: O, S, and N; optionally saturated, partially unsaturated or unsaturated; and said 5–6 membered heterocyclic ring system is substituted with 0–4 $Q^{1a}$;

$Q^{1a}$ is H, F, Cl, Br, I, —$NO_2$, —CN, —NCS, —$CF_3$, —$OCF_3$, —$CO_2R^8$, —C(=O)$NR^8R^9$, —NHC(=O)$R^8$, —$SO_2R^8$, —$SO_2NR^8R^9$, —$NR^8R^9$, —$OR^8$, —$SR^8$, $C_1$–$C_4$ alkyl, $C_1$–$C_4$ haloalkyl, or $C_1$–$C_4$ haloalkoxy;

A is $A^2$-$A^3$, $A^2$-$A^3$-$A^4$, $A^2$-$A^3$-$A^4$-$A^5$, or $A^2$-$A^3$-$A^4$-$A^5$-$A^6$;

$A^2$ is a natural amino acid, a modified amino acid, an unnatural amino acid, or

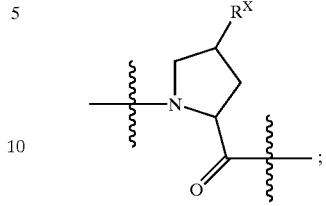

wherein said amino acid is of either D or L configuration;

$R^x$ is H or —(CH$_2$)$_m$—$R^{16}$—(CH$_2$)$_n$—$R^{12}$;

m and n are independently selected from 0, 1, or 2;

$A^3$, $A^4$, $A^5$, and $A^6$ are independently selected from an amino acid residue wherein said amino acid residue, at each occurence, is independently selected from a natural amino acid, a modified amino acid, or an unnatural amino acid wherein said natural, modified or unnatural amino acid is of either D or L configuration;

$R^1$ is —$CH_2CH_2$—$R^{1a}$, —$CH_2CH_2CH_2$—$R^{1a}$, —$CH_2CH_2CH_2CH_2$—$R^{1a}$, —$CH_2CH_2CH_2CH_2CH_2$—$R^{1a}$, —$CH_2CH_2CH_2CH_2CH_2CH_2$—$R^{1a}$, —$CH_2CH_2CH_2CH_2CH_3$, —$CH_2CH_2CH_2CH_2CH_2CH_3$, —$CH_2CH_2CH_2$C($CH_3$)$_2$, —$CH_2CH_2CH_2$C($CH_2CH_3$)$_2$, or —$CH_2CH_2CH_2$-cyclobutyl;

$R^{1a}$ is

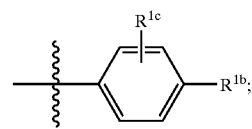

$R^{1b}$ is selected at each occurrence from the group: H, $C_1$–$C_4$ alkyl, F, Cl, Br, I, —OH, $C_1$–$C_4$ alkoxy, phenoxy, benzyloxy, —SH, —CN, —$NO_2$, —C(=O)$OR^{1d}$, —$NR^{1d}R^{1d}$, —$CF_3$, —$OCF_3$, $C_3$–$C_6$ cycloalkyl, and aryl substituted by 0–3 $R^{1c}$;

$R^{1c}$ is selected at each occurrence from the group: methyl, ethyl, Cl, F, Br, I, OH, methoxy, ethoxy, —CN, —$NO_2$, —C(=O)$OR^{1d}$, $NR^{1d}R^{1d}$, —$CF_3$, and —$OCF_3$;

$R^{1d}$ is H, $C_1$–$C_4$ alkyl, phenyl or benzyl;

$R^2$ is H, $C_1$–$C_4$ alkyl, aryl, aryl($C_1$–$C_4$ alkyl)-, or $C_3$–$C_6$ cycloalkyl;

$R^3$ is H, $C_1$–$C_4$ alkyl, aryl, aryl($C_1$–$C_4$ alkyl)-, —C(=O) $R^{11}$, —$CO_2R^{11}$, —C(=O)$NHR^{11}$, —S(=O)$R^{11}$, —S(=O)$_2R^{11}$, or an $NH_2$-blocking group;

$R^4$ and $R^5$, are independently selected from: H, $C_1$–$C_4$ alkyl, aryl($C_1$–$C_4$ alkyl)-, and $C_3$–$C_7$ cycloalkyl;

$R^6$ is selected from the group: H, —$CO_2R^7$, —$NR^7R^7$, and $C_1$–$C_6$ alkyl substituted with 0–1 $R^{1a}$;

$R^{6a}$ is selected from the group: halo, —$NO_2$, —CN, —$CF_3$, —$CO_2R^7$, —$NR^7R^7$, —$OR^7$, —$SR^7$, —C(=NH)$NH_2$, and aryl substituted with 0–1 $R^{6b}$;

$R^{6b}$ is selected from the group: —$CO_2H$, —$NH_2$, —OH, —SH, and —C(=NH)$NH_2$;

$R^{6c}$ is H or $C_1$–$C_4$ alkyl;

$R^7$ at each occurrence is independently selected from the group: H, $C_1$–$C_4$ alkyl, aryl, and aryl($C_1$–$C_4$ alkyl)-, wherein aryl is optionally substituted with 0–3 substituents selected from —$CH_3$, —$NO_2$, —CN, —OH, —$OCH_3$, —$SO_2CH_3$, —$CF_3$, Cl, Br, I, and F;

alternatively, —$NR^7R^7$ may optionally form a 5–6 membered heterocycle consisting of carbon atoms, a nitrogen atom, and optionally a second heteroatom selected from the group: O, S, and N;

$R^8$ and $R^9$ are independently selected from H, $C_1$–$C_4$ alkyl, aryl($C_1$–$C_4$ alkyl)-, and $C_3$–$C_7$ cycloalkyl;

alternatively, $NR^8R^9$ may form a 5–6 membered heterocycle consisting of carbon atoms, a nitrogen atom, and optionally a second heteroatom selected from the group: O, S, and N;

$R^{11}$ is $C_1$–$C_4$ alkyl substituted with 0–1 $R^{11a}$,
6–10 membered aryl substituted with 0–2 $R^{11b}$, or
5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{11b}$;

$R^{11a}$ is $C_1$–$C_4$ alkyl, halogen, —$OR^{14}$, —$SR^{14}$, —$NR^{14}R^{15}$, aryl, or a 5–6 membered heterocyclic ring system containing 1, 2 or 3 heteroatoms selected from nitrogen, oxygen and sulfur;

$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, $C_1$–$C_4$ alkyl, $C_1$–$C_4$ alkoxy, $C_1$–$C_4$ thioalkoxy, aryl, or aryl ($C_1$–$C_4$ alkyl)-, wherein aryl is optionally substituted with 0–3 substituents selected from —$CH_3$, —$NO_2$, —CN, —OH, —$OCH_3$, —$SO_2CH_3$, —$CF_3$, Cl, Br, I, and F;

$R^{12}$ is selected from the group: H;
$C_1$–$C_6$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
$C_3$–$C_7$ cycloalkyl substituted with 0–3 $R^{12a}$;
$C_4$–$C_{10}$ (cycloalkyl-alkyl) substituted with 0–3 $R^{12a}$;
6–10 membered aryl substituted with 0–3 $R^{12a}$; and
5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: $C_1$–$C_6$ alkoxy; lower thioalkyl; sulfonyl; —$NO_2$; halogen; haloalkyl; carboxyl; carboxy(lower alkyl); —$OR^{14}$; —$SR^{14}$; —$NR^{14}R^{15}$; —C(=O)$NR^{14}R^{15}$; —$NR^{14}$C(=O)$R^{15}$; —S(=O)$_2R^{14}$;
$C_1$–$C_6$ alkyl substituted with 0–3 $R^{12b}$;
$C_2$–$C_6$ alkenyl substituted with 0–3 $R^{12b}$;
$C_2$–$C_6$ alkynyl substituted with 0–3 $R^{12b}$;
$C_3$–$C_7$ cycloalkyl substituted with 0–3 $R^{12b}$;
$C_4$–$C_{10}$ (alkylcycloalkyl) substituted with 0–3 $R^{12b}$;
6–10 membered aryl substituted with 0–3 $R^{12b}$; and
5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2

$R^{12b}$ is independently selected from the group: $C_1$–$C_6$ alkyl; $C_3$–$C_7$ cycloalkyl; $C_1$–$C_6$ alkoxy; halogen; —$OR^{14}$; —$SR^{14}$; —$NR^{14}R^{15}$; —C(=O)$NR^{14}R^{15}$; —$NR^{14}$C(=O) $R^{15}$; —S(=O)$_2R^{14}$; —$NO_2$; haloalkyl; carboxyl; carboxy (lower alkyl); aryl; and 5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with $C_1$–$C_6$ alkyl;

$R^{14}$ and $R^{15}$ are independently selected from the group: H, $C_1$–$C_4$ alkyl, aryl, aryl($C_1$–$C_4$ alkyl)-, and $C_3$–$C_7$ cycloalkyl;

$R^{16}$ is a bond, —O—, —S— or —$NR^{17}$—; and
$R^{17}$ is H, $C_1$–$C_4$ alkyl, aryl, aryl($C_1$–$C_4$ alkyl)-, or $C_3$–$C_6$ cycloalkyl.

[3] In an alternative embodiment, the present invention provides a compound of Formula (I) or a pharmaceutically acceptable salt or prodrug thereof, wherein:

W is —B($Y^1$)($Y^2$);
$Y^1$ and $Y^2$ are independently selected from:
a) —OH,
b) —F,
c) $C_1$–$C_8$ alkoxy, and
when taken together with B, $Y^1$ and $Y^2$ form:
d) a cyclic boronic ester where said cyclic boronic ester contains from 2 to 16 carbon atoms, and, optionally, 1, 2, or 3 heteroatoms which can be N, S, or O;

A is $A^2$-$A^3$, $A^2$-$A^3$-$A^4$, $A^2$-$A^3$-$A^4$-$A^5$, or $A^2$-$A^3$-$A^4$-$A^5$-$A^6$;

$A^2$ is Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O′Bu), Glu(O′Bu), Hyp(O′Bu), Thr (O′Bu), Asp(OBzl), Glu(OBzl), Hyp(OBzl), Thr(OBzl), cyclohexylglycine, cyclohexylalanine, cyclopropylglycine, t-butylglycine, phenylglycine, 3,3-diphenylalanine, or

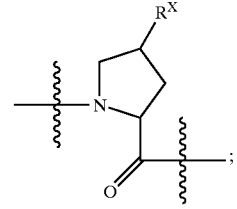

$A^3$, $A^4$, $A^5$, and $A^6$ are independently selected from an amino acid residue wherein said amino acid residue, at each occurence, is independently selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O′Bu), Glu(O′Bu), Hyp(O′Bu), Thr (O′Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine;

$R^x$ is H or —(CH$_2$)$_m$—$R^{16}$—(CH$_2$)$_n$—$R^{12}$;
m and n are independently selected from 0, 1, or 2;
$R^1$ is —$CH_2CH_2$—$R^{1a}$, —$CH_2CH_2CH_2$—$R^{1a}$, or —$CH_2CH_2CH_2CH_2CH_2$—$R^{1a}$.
$R^{1a}$ is

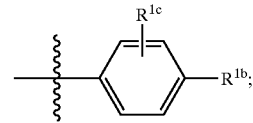

$R^{1b}$ is selected at each occurrence from the group: H, $C_1$–$C_4$ alkyl, F, Cl, Br, I, —OH, $C_1$–$C_4$ alkoxy, phenoxy, benzyloxy, —SH, —CN, —$NO_2$, —C(=O)$OR^{1d}$, —$NR^{1d}R^{1d}$, —$CF_3$, —$OCF_3$, $C_3$–$C_6$ cycloalkyl, and aryl substituted by 0–3 $R^{1c}$;

$R^{1c}$ is selected at each occurrence from the group: methyl, ethyl, Cl, F, Br, I, OH, methoxy, ethoxy, —CN, —$NO_2$, —C (=O) $OR^{1d}$, $NR^{1d}R^{1d}$, —$CF_3$, and —$OCF_3$;

$R^{1d}$ is H, $C_1$–$C_4$ alkyl, phenyl or benzyl;

$R^2$ is H, $C_1$–$C_4$ alkyl, phenyl or benzyl;

$R^3$ is H, $C_1$–$C_4$ alkyl, aryl, aryl($C_1$–$C_4$ alkyl)-, —C(=O)$R^{11}$, —CO$_2R^{11}$, —C(=O)NHR$^{11}$, or an NH$_2$-blocking group;

$R^{11}$ is $C_1$–$C_4$ alkyl substituted with 0–1 $R^{11a}$,

6–10 membered aryl substituted with 0–2 $R^{11b}$, or

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{11b}$;

$R^{11a}$ is $C_1$–$C_4$ alkyl, halogen, —OR$^{14}$, —SR$^{14}$, —NR$^{14}R^{15}$, aryl, or a 5–6 membered heterocyclic ring system containing 1, 2 or 3 heteroatoms selected from nitrogen, oxygen and sulfur;

$R^{11b}$ is —NO$_2$, —NH$_2$, —SO$_3$H, —SO$_2$CH$_3$, —CO$_2$H, —CF$_3$, —OH, —SH, —OCF$_3$, Cl, Br, I, F, =O, $C_1$–$C_4$ alkyl, $C_1$–$C_4$ alkoxy, $C_1$–$C_4$ thioalkoxy, aryl, or aryl ($C_1$–$C_4$ alkyl)-, wherein aryl is optionally substituted with 0–3 substituents selected from —CH$_3$, —NO$_2$, —CN, —OH, —OCH$_3$, —SO$_2$CH$_3$, —CF$_3$, Cl, Br, I, and F;

$R^{12}$ is selected from the group: H;

$C_1$–$C_6$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_3$–$C_7$ cycloalkyl substituted with 0–3 $R^{12a}$;

$C_4$–$C_{10}$ (cycloalkyl-alkyl) substituted with 0–3 $R^{12a}$;

6–10 membered aryl substituted with 0–3 $R^{12a}$; and

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: $C_1$–$C_6$ alkoxy; lower thioalkyl; sulfonyl; —NO$_2$; halogen; haloalkyl; carboxyl; carboxy(lower alkyl); —OR$^{14}$; —SR$^{14}$; —NR$^{14}R^{15}$; —C(=O)NR$^{14}R^{15}$; —NR$^{14}$C(=O)$R^{15}$; —S(=O)$_2R^{14}$;

$C_1$–$C_6$ alkyl substituted with 0–3 $R^{12b}$;

$C_2$–$C_6$ alkenyl substituted with 0–3 $R^{12b}$;

$C_2$–$C_6$ alkynyl substituted with 0–3 $R^{12b}$;

$C_3$–$C_7$ cycloalkyl substituted with 0–3 $R^{12b}$;

$C_4$–$C_{10}$ (alkylcycloalkyl) substituted with 0–3 $R^{12b}$;

6–10 membered aryl substituted with 0–3 $R^{12b}$; and

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12b}$;

$R^{12b}$ is independently selected from the group: $C_1$–$C_6$ alkyl; $C_3$–$C_7$ cycloalkyl; $C_1$–$C_6$ alkoxy; halogen; —OR$^{14}$; —SR$^{14}$; —NR$^{14}R^{15}$; —C(=O)NR$^{14}R^{15}$; —NR$^{14}$C(=O)$R^{15}$; —S(=O)$_2R^{14}$; —NO$_2$; haloalkyl; carboxyl; carboxy (lower alkyl); and 5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with $C_1$–$C_6$ alkyl;

$R^{14}$ and $R^{15}$ are independently selected from the group: H, $C_1$–$C_4$ alkyl, aryl, aryl($C_1$–$C_4$ alkyl)-, and $C_3$–$C_7$ cycloalkyl;

$R^{16}$ is a bond, —O—, —S— or —NR$^{17}$—; and $R^{17}$ is H, $C_1$–$C_4$ alkyl, aryl or aryl($C_1$–$C_4$ alkyl).

[4] In another alternative embodiment, the present invention provides a compound of Formula (I) or a pharmaceutically acceptable salt or prodrug thereof, wherein:

W is —B (Y$^1$)(Y$^2$)

$Y^1$ and $Y^2$ are independently selected from:

a) —OH, b) $C_1$–$C_6$ alkoxy, or when taken together with B, $Y^1$ and $Y^2$ form:

d) a cyclic boronic ester where said cyclic boronic ester contains from 2 to 16 carbon atoms;

A is $A^2$-$A^3$-$A^4$, $A^2$-$A^3$-$A^4$-$A^5$, or $A^2$-$A^3$-$A^4$-$A^5$-$A^6$;

$A^2$ is Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O$^t$Bu), Glu(O$^t$Bu), Hyp(O$^t$Bu), Thr (O$^t$Bu), Asp(OBzl), Glu(OBzl), Hyp(OBzl), Thr(OBzl), cyclohexylglycine, cyclohexylalanine, cyclopropylglycine, t-butylglycine, phenylglycine, 3,3-diphenylalanine, or

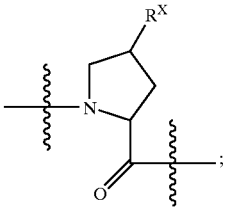

$A^3$, $A^4$, $A^5$, and $A^6$ are independently selected from an amino acid residue wherein said amino acid residue, at each occurence, is independently selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O$^t$Bu), Glu(O$^t$Bu), Hyp(O$^t$Bu), Thr (O$^t$Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine;

$R^x$ is H or —(CH$_2$)$_m$—R$^{16}$—(CH$_2$)$_n$—R$^{12}$;

m and n are independently selected from 0, 1, or 2;

$R^1$ is —CH$_2$CH$_2$—R$^{1a}$, —CH$_2$CH$_2$CH$_2$CH$_2$—R$^{1a}$, or —CH$_2$CH$_2$CH$_2$CH$_2$CH$_2$—R$^{1a}$.

$R^{1a}$ is

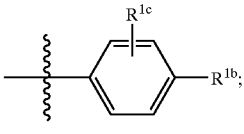

$R^{1b}$ is selected at each occurrence from the group: H, $C_1$–$C_4$ alkyl, F, Cl, Br, I, —OH, $C_1$–$C_4$ alkoxy, phenoxy, benzyloxy, —SH, —CN, —NO$_2$, —C(=O)OR$^{1d}$, —NR$^{1d}R^{1d}$, —CF$_3$, —OCF$_3$, $C_3$–$C_6$ cycloalkyl, and aryl substituted by 0–3 $R^{1c}$;

$R^{1c}$ is selected at each occurrence from the group: methyl, ethyl, Cl, F, Br, I, OH, methoxy, ethoxy, —CN, —NO$_2$, —C(=O)OR$^{1d}$, NR$^{1d}R^{1d}$, —CF$_3$, and —OCF$_3$;

$R^{1d}$ is H, $C_1$–$C_4$ alkyl, phenyl or benzyl;

$R^2$ is H, methyl, ethyl, propyl, or butyl;

$R^3$ is H, $C_1$–$C_4$ alkyl, aryl, aryl($C_1$–$C_4$ alkyl)-, —C(=O)$R^{11}$, —CO$_2R^{11}$, —C(=O)NHR$^{11}$ or acetyl;

13

$R^{11}$ is $C_1$–$C_4$ alkyl substituted with 0–1 $R^{11a}$, phenyl substituted with 0–2 $R^{11b}$, or 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{11b}$;

$R^{11a}$ is $C_1$–$C_4$ alkyl, halogen, —$OR^{14}$, —$SR^{14}$, —$NR^{14}R^{15}$, phenyl, or a 5–6 membered heterocyclic ring system containing 1, 2 or 3 heteroatoms selected from nitrogen, oxygen and sulfur;

$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, methyl, ethyl, propyl, butyl, —$OCH_3$, —$OCH_2CH_3$, —$SCH_3$, —$SCH_2CH_3$, phenyl, or benzyl;

$R^{12}$ is selected from the group: H;
$C_1$–$C_4$ alkyl substituted with 0–2 $R^{12a}$;
6–10 membered substituted with 0–3 $R^{12a}$; and
5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: —$NO_2$; halogen; haloalkyl; carboxyl; carboxy(lower alkyl); —$OR^{14}$; —$SR^{14}$; —$NR^{14}R^{15}$; —$C(=O)NR^{14}R^{15}$; —$NR^{14}C(=O)R^{15}$; $C_1$–$C_4$ alkyl substituted with 0–2 $R^{12b}$; phenyl substituted with 0–3 $R^{12b}$; and 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{12b}$;

$R^{12b}$ is independently selected from the group: $C_1$–$C_4$ alkyl; $C_3$–$C_6$ cycloalkyl; F; Cl; Br; I; —$OR^{14}$; —$SR^{14}$; —$NR^{14}R^{15}$; —$C(=O)NR^{14}R^{15}$; —$NR^{14}C(=O)R^{15}$; —$S(=O)_2R^{14}$; —$NO_2$; haloalkyl; carboxyl; carboxy (lower alkyl); and 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with $C_1$–$C_6$ alkyl;

$R^{14}$ and $R^{15}$ are independently selected from the group: H, $C_1$–$C_4$ alkyl, phenyl and benzyl;

$R^{16}$ is a bond, —O—, —S— or —$NR^7$—; and $R^{17}$ is H, methyl, ethyl, propyl, butyl, phenyl or benzyl.

[5] In another alternative embodiment, the present invention provides a compound of Formula (I) or a pharmaceutically acceptable salt or prodrug thereof, wherein:
W is —$B(Y^1)(Y^2)$;
$Y^1$ and $Y^2$ are independently selected from:
a) —OH,
b) $C_1$–$C_6$ alkoxy, or
when taken together with B, $Y^1$ and $Y^2$ form:
d) a cyclic boronic ester where said cyclic boronic ester contains from 2 to 14 carbon atoms;
A is $A^2$-$A^3$-$A^4$, $A^2$-$A^3$-$A^4$-$A^5$, or $A^2$-$A^3$-$A^4$-$A^5$-$A^6$;
$A^2$ is Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O'Bu), Glu(O'Bu), Hyp(O'Bu), Thr (O'Bu), Asp(OBzl), Glu(OBzl), Hyp(OBzl), Thr(OBzl), cyclohexylglycine, cyclohexylalanine, cyclopropylglycine, t-butylglycine, phenylglycine, 3,3-diphenylalanine, or

14

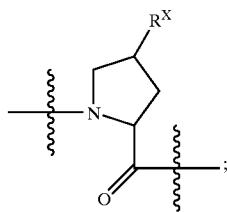

$A^3$, $A^4$, $A^5$, and $A^6$ are independently selected from an amino acid residue wherein said amino acid residue, at each occurence, is independently selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O'Bu), Glu(O'Bu), Hyp(O'Bu), Thr (O'Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine;

$R^x$ is H or —$(CH_2)_m$—$R^{16}$—$(CH_2)_n$—$R^{12}$;
m and n are independently selected from 0 or 1;
$R^1$ is —$CH_2CH_2$—$R^{1a}$ or —$CH_2CH_2CH_2CH_2$—$R^{1a}$;
$R^{1a}$ is

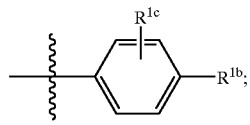

$R^{1b}$ is selected at each occurrence from the group: H, $C_1$–$C_4$ alkyl, F, Cl, Br, I, —OH, $C_1$–$C_4$ alkoxy, phenoxy, benzyloxy, —SH, —CN, —$NO_2$, —$C(=O)OR^{1d}$, —$NR^{1d}R^{1d}$, —$CF_3$, —$OCF_3$, $C_3$–$C_6$ cycloalkyl, and aryl substituted by 0–3 $R^{1c}$;

$R^{1c}$ is selected at each occurrence from the methyl, ethyl, Cl, F, Br, I, OH, methoxy, ethoxy, —CN, —$NO_2$, —$C(=O)OR^{1d}$, $NR^{1d}R^{1d}$, —$CF_3$, and —$OCF_3$;

$R^{1d}$ is H, methyl, ethyl, propyl, butyl, phenyl or benzyl;
$R^2$ is H or methyl;
$R^3$ is H, methyl, ethyl, propyl, butyl, phenyl, benzyl, —$C(=O)R^{11}$, —$CO_2R^{11}$, —$C(=O)NHR^{11}$ or acetyl;
$R^{11}$ is $C_1$–$C_4$ alkyl substituted with 0–1 $R^{11a}$, phenyl substituted with 0–2 $R^{11b}$, or 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{11b}$;

$R^{11a}$ is methyl, ethyl propyl, butyl, F, Cl, Br, Cl, —OH, —$OCH_3$, —SH, —$SCH_3$, —$NH_2$, —$NHCH_3$, —$N(CH_3)_2$, phenyl, or a 5–6 membered heterocyclic ring system containing 1, 2 or 3 heteroatoms selected from nitrogen, oxygen and sulfur;

$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, methyl, ethyl, propyl, butyl, —$OCH_3$, —$OCH_2CH_3$, —$SCH_3$, —$SCH_2CH_3$, phenyl, or benzyl;

$R^{12}$ is selected from the group: H;
$C_1$–$C_4$ alkyl substituted with 0–2 $R^{12a}$;
6–10 membered aryl substituted with 0–3 $R^{12a}$; and 5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: —$NO_2$; halogen; haloalkyl; carboxyl; carboxy(lower alkyl); —$OR^{14}$; —$SR^{14}$; —$NR^{14}R^{15}$; —$C(=O)NR^{14}R^{15}$; —$NR^{14}C(=O)R^{15}$;

$C_1$–$C_4$ alkyl substituted with 0–3 $R^{12b}$;

phenyl substituted with 0–3 $R^{12b}$; and

5–6 membered heterocyclic ring system consisting of carbon atoms and 1–4 heteroatoms selected from the group: O, S, and N; optionally saturated, partially unsaturated or unsaturated;

$R^{12b}$ is independently selected from the group: $C_1$–$C_4$ alkyl; $C_3$–$C_6$ cycloalkyl; F; Cl; Br; I; —$OR^{14}$; —$SR^{14}$; —$NR^{14}R^{15}$; —$C(=O)NR^{14}R^{15}$; —$NR^{14}C(=O)R^{15}$; —$S(=O)_2R^{14}$; —$NO_2$; haloalkyl; carboxyl; carboxy (lower alkyl); and 5–6 membered heterocyclic ring system consisting of carbon atoms and 1–4 heteroatoms selected from the group: O, S, and N; optionally saturated, partially unsaturated or unsaturated;

$R^{14}$ and $R^{15}$ are independently selected from the group: H, methyl, ethyl, propyl, butyl, phenyl, and benzyl;

$R^{16}$ is a bond, —O—, —S— or —$NR^{17}$—; and $R^{17}$ is H, methyl, ethyl, propyl, butyl, phenyl, or benzyl.

[6] In another alternative embodiment, the present invention provides a compound of Formula (I) or a pharmaceutically acceptable salt or prodrug thereof, wherein:

W is —$B(Y^1)(Y^2)$;

$Y^1$ and $Y^2$ are independently selected from:

a) —OH, b) $C_1$–$C_6$ alkoxy, or when taken together with B, $Y^1$ and $Y^2$ form:

c) a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanediol, 5,6-decanediol, 1,2-dicyclohexylethanediol, diethanolamine, and 1,2-diphenyl-1,2-ethanediol;

A is $A^2$-$A^3$-$A^4$, $A^2$-$A^3$-$A^4$-$A^5$, or $A^2$-$A^3$-$A^4$-$A^5$-$A^6$;

$A^2$ is Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O′Bu), Glu(O′Bu), Hyp(O′Bu), Thr(O′Bu), Asp(OBzl), Glu(OBzl), Hyp(OBzl), Thr(OBzl), cyclohexylglycine, cyclohexylalanine, cyclopropylglycine, t-butylglycine, phenylglycine, 3,3-diphenylalanine, or

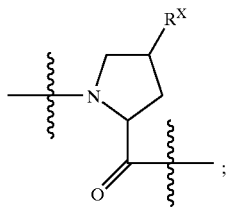

$A^3$, $A^4$, $A^5$, and $A^6$ are independently selected from an amino acid residue wherein said amino acid residue, at each occurence, is independently selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O′Bu), Glu(O′Bu), Hyp(O′Bu), Thr (O′Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine;

$R^x$ is H, or —$(CH_2)_m$—$R^{16}$—$(CH_2)_n$—$R^{12}$;

m and n are independently selected from 0 or 1;

$R^1$ is —$CH_2CH_2$—$R^{1a}$ or —$CH_2CH_2CH_2CH_2$—$R^{1a}$;

$R^{1a}$ is

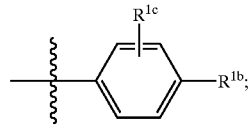

$R^{1b}$ is selected at each occurrence from the group: H, $C_1$–$C_4$ alkyl, F, Cl, Br, I, —OH, $C_1$–$C_4$ alkoxy, phenoxy, benzyloxy, —SH, —CN, —$NO_2$, —$C(=O)OR^{1d}$, —$NR^{1d}R^{1d}$, —$CF_3$, —$OCF_3$, $C_3$–$C_6$ cycloalkyl, and aryl substituted by 0–3 $R^{1c}$;

$R^{1c}$ is selected at each occurrence from the methyl, ethyl, Cl, F, Br, I, OH, methoxy, ethoxy, —CN, —$NO_2$, —$C(=O)OR^{1d}$, $NR^{1d}R^{1d}$, —$CF_3$, and —$OCF_3$;

$R^{1d}$ is H, methyl, ethyl, propyl, butyl, phenyl or benzyl;

$R^2$ is H or methyl;

$R^3$ is H, methyl, ethyl propyl, butyl, phenyl, benzyl, —$C(=O)R^{11}$, —$CO_2R^{11}$, —$C(=O)NHR^{11}$ or acetyl;

$R^{11}$ is $C_1$–$C_4$ alkyl substituted with 0–1 $R^{11a}$, phenyl substituted with 0–2 $R^{11b}$, or 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{11b}$;

$R^{11a}$ is methyl, ethyl propyl, butyl, F, Cl, Br, Cl, —OH, —$OCH_3$, —SH, —$SCH_3$, —$NH_2$, —$NHCH_3$, —$N(CH_3)_2$, phenyl, or a 5–6 membered heterocyclic ring system containing 1, 2 or 3 heteroatoms selected from nitrogen, oxygen and sulfur;

$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, methyl, ethyl, propyl, butyl, —$OCH_3$, —$OCH_2CH_3$, —$SCH_3$, —$SCH_2CH_3$, phenyl, or benzyl;

$R^{12}$ is selected from the group: H;

$C_1$–$C_4$ alkyl substituted with 0–2 $R^{12a}$;

6–10 member aryl substituted with 0–3 $R^{12a}$; and

5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;

$R^{12a}$ is independently selected from the group: —$NO_2$; halogen; haloalkyl; carboxyl; carboxy(lower alkyl); —$OR^{14}$; —$SR^{14}$; —$NR^{14}R^{15}$; —$C(=O)NR^{14}R^{15}$; —$NR^{14}C(=O)R^{15}$; $C_1$–$C_4$ alkyl; phenyl; and 5–6 membered heterocyclic ring system consisting of carbon atoms and 1–4 heteroatoms selected from the group: O, S, and N; optionally saturated, partially unsaturated or unsaturated;

$R^{14}$ and $R^{15}$ are independently selected from the group: H, methyl, and ethyl; and $R^{16}$ is a bond, —O— or —S—.

[7] In another alternative embodiment, the present invention provides a compound of Formula (I) or a pharmaceutically acceptable salt or prodrug thereof, wherein:

W is pinanediol boronic ester;
A is $A^2$-$A^3$-$A^4$, $A^2$-$A^3$-$A^4$-$A^5$, or $A^2$-$A^3$-$A^4$-$A^5$-$A^6$;
$A^2$ is Ala, Arg, Asn, Asp, Cys, Gln, Glu, Gly, His, Hyp, Ile, Leu, Lys, Met, Phe, Pro, Ser, Thr, Trp, Tyr, Val, Abu, Asp(OMe), Glu(OMe), Hyp(OMe), Asp(O$^t$Bu), Glu(O$^t$Bu), Hyp(O$^t$Bu), Thr(O$^t$Bu), Asp(OBzl), Glu(OBzl), Hyp(OBzl), Thr(OBzl), cyclohexylalanine, or

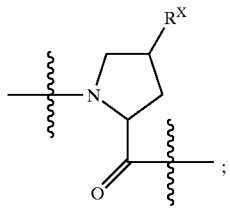

$A^3$, $A^4$, $A^5$, and $A^6$ are independently selected from an amino acid residue wherein said amino acid residue, at each occurence, is independently selected from the group: Ala, Arg, Asn, Asp, Cys, Gln, Glu, Gly, His, Hyp, Ile, Leu, Lys, Met, Phe, Pro, Ser, Thr, Trp, Tyr, Val, Asp(OMe), Glu(OMe), Hyp(OMe), Asp(O$^t$Bu), Gla; Glu(O$^t$Bu), Hyp(O$^t$Bu), Thr(O$^t$Bu), Asp(OBzl), Glu(OBzl), Hyp(OBzl), Thr(OBzl), cyclohexylglycine, cyclohexylalanine, cyclohexylglycine, cyclopropylglycine, t-butylglycine, phenylglycine, and 3,3-diphenylalanine;
$R^1$ is —$CH_2CH_2$—$R^{1a}$ or —$CH_2CH_2CH_2CH_2$—$R^{1a}$;
$R^{1a}$ is selected from the group: phenyl, 2-naphthyl, 2-methylphenyl, 3-methylphenyl, 4-methylphenyl, 4-(1,1'-biphenyl)-, 2,5-dimethylphenyl, 2,4-dimethylphenyl, 3-$CF_3$-phenyl, 4-$CF_3$-phenyl, 2-F-phenyl, 3-F-phenyl, 4-F-phenyl, 4-Cl-phenyl, 4-Br-phenyl, 4-phenoxyphenyl, 4-isopropylphenyl, 4-cyclohexylphenyl, 4-tBu-phenyl, 4-methoxyphenyl, 2,6-diF-phenyl, 4-hydroxy-phenyl, (4-methyoxyphenoxy)phenyl, methyl, ethyl, propyl, i-propyl, n-butyl, i-butyl, and cyclobutyl;
$R^X$ is H or —$(CH_2)_m$—$R^{16}$—$(CH_2)_n$—$R^{12}$;
m and n are independently selected from 0 or 1;
$R^2$ is H or methyl;
$R^3$ is H, methyl, ethyl propyl, butyl, phenyl, benzyl, —C(=O)$R^{11}$, —$CO_2R^{11}$, —C(=O)NH$R^{11}$ or acetyl;
$R^{11}$ is $C_1$-$C_4$ alkyl substituted with 0-1 $R^{11a}$, phenyl substituted with 0-2 $R^{11b}$, or
  5-6 membered heterocyclic ring system consisting of carbon atoms and 1-4 heteroatoms selected from the group: O, S, and N; optionally saturated, partially unsaturated or unsaturated; said 5-6 membered heterocyclic ring system is substituted with 0-2 $R^{11b}$;
$R^{11a}$ is methyl, ethyl propyl, butyl, F, Cl, Br, Cl, —OH, —$OCH_3$, —SH, —$SCH_3$, —$NH_2$, —$NHCH_3$, —$N(CH_3)_2$, phenyl, or a
  5-6 membered heterocyclic ring system containing 1, 2 or 3 heteroatoms selected from nitrogen, oxygen and sulfur;
$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, methyl, ethyl, propyl, butyl, —$OCH_3$, —$OCH_2CH_3$, —$SCH_3$, —$SCH_2CH_3$, phenyl, or benzyl;
$R^{12}$ is selected from the group: H;
  $C_1$-$C_4$ alkyl substituted with 0-2 $R^{12a}$;
  6-10 member aryl substituted with 0-3 $R^{12a}$; and
  5-10 membered heterocyclic ring system consisting of carbon atoms and 1-4 heteroatoms selected from the group: O, S, and N; optionally saturated, partially unsaturated or unsaturated; said 5-10 membered heterocyclic ring system is substituted with 0-2 $R^{12a}$;
$R^{12a}$ is independently selected from the group: —$NO_2$; halogen; haloalkyl; carboxyl; carboxy(lower alkyl); —$OR^{14}$; —$SR^{14}$; —$NR^{14}R^{15}$; —C(=O)$NR^{14}R^{15}$; —$NR^{14}C$(=O)$R^{15}$; $C_1$-$C_4$ alkyl; phenyl; and
  5-6 membered heterocyclic ring system consisting of carbon atoms and 1-4 heteroatoms selected from the group: O, S, and N; optionally saturated, partially unsaturated or unsaturated;
$R^{14}$ and $R^{15}$ are independently selected from the group: H, methyl, and ethyl; and
$R^{16}$ is a bond, —O— or —S—.

[8] In another alternative embodiment, the present invention provides a compound of Formula (I) or a pharmaceutically acceptable salt or prodrug thereof, wherein:

W is pinanediol boronic ester;
A is $A^2$-$A^3$-$A^4$, $A^2$-$A^3$-$A^4$-$A^5$, or $A^2$-$A^3$-$A^4$-$A^5$-$A^6$;
$A^2$ is Ala, Arg, Asn, Asp, Cys, Gln, Glu, Gly, His, Hyp, Ile, Leu, Lys, Met, Phe, Pro, Ser, Thr, Trp, Tyr, Val, Abu, Asp(OMe), Glu(OMe), Hyp(OMe), Asp(O$^t$Bu), Glu(O$^t$Bu), Hyp(O$^t$Bu), Thr(O$^t$Bu), Asp(OBzl), Glu(OBzl), Hyp(OBzl), Thr(OBzl), cyclohexylalanine, or

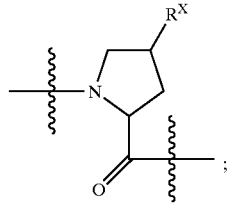

$A^3$, $A^4$, $A^5$, and $A^6$ are independently selected from an amino acid residue wherein said amino acid residue, at each occurence, is independently selected from the group: Ala, Arg, Asn, Asp, Cys, Gln, Glu, Gly, His, Hyp, Ile, Leu, Lys, Met, Phe, Pro, Ser, Thr, Trp, Tyr, Val, Asp(OMe), Glu(OMe), Hyp(OMe), Asp(O$^t$Bu), Gla; Glu(O$^t$Bu), Hyp(O$^t$Bu), Thr(O$^t$Bu), Asp(OBzl), Glu(OBzl), Hyp(OBzl), Thr(OBzl), cyclohexylglycine, cyclohexylalanine, cyclohexylglycine, cyclopropylglycine, t-butylglycine, phenylglycine, and 3,3-diphenylalanine;
$R^1$ is —$CH_2CH_2$—$R^{1a}$ or —$CH_2CH_2CH_2CH_2$—$R^{1a}$;
$R^{1a}$ is selected from the group: phenyl, 2-naphthyl, 2-methylphenyl, 3-methylphenyl, 4-methylphenyl, 4-(1,1'-biphenyl)-, 2,5-dimethylphenyl, 2,4-dimethylphenyl, 3-$CF_3$-phenyl, 4-$CF_3$-phenyl, 2-F-phenyl, 3-F-phenyl, 4-F-phenyl, 4-Cl-phenyl, 4-Br-phenyl, 4-phenoxyphenyl, 4-isopropylphenyl, 4-cyclohexylphenyl, 4-tBu-phenyl, 4-methoxyphenyl, 2,6-diF-phenyl, 4-hydroxy-phenyl, (4-methyoxyphenoxy) phenyl, methyl, ethyl, propyl, i-propyl, n-butyl, i-butyl, and cyclobutyl;
$R^X$ is H or benzoxy;
$R^2$ is H;
$R^3$ is H, —C(=O)$R^{11}$ or acetyl;
$R^{11}$ is 5-6 membered heterocyclic ring system consisting of carbon atoms and 1-4 heteroatoms selected from the group: O, S, and N; optionally saturated, partially unsaturated or unsaturated; said 5-6 membered heterocyclic ring system is substituted with 0-2 $R^{11b}$; and
$R^{11b}$ is —$NO_2$, —$NH_2$, —$SO_3H$, —$SO_2CH_3$, —$CO_2H$, —$CF_3$, —OH, —SH, —$OCF_3$, Cl, Br, F, methyl, ethyl, propyl, butyl, —$OCH_3$, or —$OCH_2CH_3$.

[9] In another alternative embodiment, the present invention provides a compound of Formula (I) or a pharmaceutically acceptable salt or prodrug thereof, wherein:
W is pinanediol boronic ester;
A is $A^2$-$A^3$-$A^4$, $A^2$-$A^3$-$A^4$-$A^5$, or $A^2$-$A^3$-$A^4$-$A^5$-$A^6$;
$A^2$ is Pro, Leu, Asp, Abu, Val, cyclohexylalanine, or

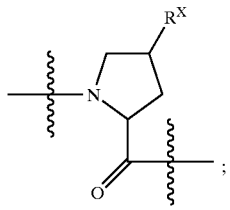

$A^3$ is Val, Glu, Ile, Thr, cyclohexylglycine, or cyclohexylalanine;
$A^4$ is Val, Ile, Leu, cyclohexylglycine, cyclopropylglycine, t-butylglycine, phenylglycine, or 3,3-diphenylalanine;
$A^5$ is Asp, Glu, Val, Ile, t-butylglycine or Gla;
$A^6$ is Asp or Glu;
$R^1$ is —$CH_2CH_2$—$R^{1a}$ or —$CH_2CH_2CH_2CH_2$—$R^{1a}$;
$R^{1a}$ is selected from the group: phenyl, 2-naphthyl, 2-methylphenyl, 3-methylphenyl, 4-methylphenyl, 4-(1,1'-biphenyl)-, 2,5-dimethylphenyl, 2,4-dimethylphenyl, 3-$CF_3$-phenyl, 4-$CF_3$-phenyl, 2-F-phenyl, 3-F-phenyl, 4-F-phenyl, 4-Cl-phenyl, 4-Br-phenyl, 4-phenoxyphenyl, 4-isopropylphenyl, 4-cyclohexylphenyl, 4-tBu-phenyl, 4-methoxyphenyl, 2,6-diF-phenyl, 4-hydroxy-phenyl, (4-methyoxyphenoxy)phenyl, methyl, ethyl, propyl, i-propyl, n-butyl, i-butyl, and cyclobutyl;
$R^X$ is H or —$(CH_2)_m$—$R^{16}$—$(CH_2)_n$—$R^{12}$;
m and n are independently selected from 0 or 1;
$R^2$ is H or methyl;
$R^3$ is H, methyl, ethyl propyl, butyl, phenyl, benzyl, —C(=O)$R^{11}$, —$CO_2R^{11}$, —C(=O)NH$R^{11}$ or acetyl;
$R^{11}$ is $C_1$-$C_4$ alkyl substituted with 0–1 $R^{11a}$, phenyl substituted with 0–2 $R^{11b}$, or
  5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{11b}$;
$R^{11a}$ is methyl, ethyl propyl, butyl, F, Cl, Br, Cl, —OH, —$OCH_3$, —SH, —$SCH_3$, —$NH_2$, —$NHCH_3$, —$N(CH_3)_2$, phenyl, or a
  5–6 membered heterocyclic ring system containing 1, 2 or 3 heteroatoms selected from nitrogen, oxygen and sulfur;
$R^{11b}$ is —$NO_2$, —$NH_2$, —$SO_3H$, —$SO_2CH_3$, —$CO_2H$, —$CF_3$, —OH, —SH, —$OCF_3$, Cl, Br, I, F, =O, methyl, ethyl, propyl, butyl, —$OCH_3$, —$OCH_2CH_3$, —$SCH_3$, —$SCH_2CH_3$, phenyl, or benzyl;
$R^{12}$ is selected from the group: H;
  $C_1$-$C_4$ alkyl substituted with 0–2 $R^{12a}$;
  6–10 member aryl substituted with 0–3 $R^{12a}$; and
  5–10 membered heterocyclic ring system consisting of carbon atoms and 1–4 heteroatoms selected from the group: O, S, and N; optionally saturated, partially unsaturated or unsaturated; said 5–10 membered heterocyclic ring system is substituted with 0–2 $R^{12a}$;
$R^{12a}$ is independently selected from the group: —$NO_2$; halogen; haloalkyl; carboxyl; carboxy(lower alkyl); —$OR^{14}$; —$SR^{14}$; —$NR^{14}R^{15}$; —C(=O)$NR^{14}R^{15}$; —$NR^{14}C(=O)R^{15}$; $C_1$-$C_4$ alkyl; phenyl; and
  5–6 membered heterocyclic ring system consisting of carbon atoms and 1–4 heteroatoms selected from the group: O, S, and N; optionally saturated, partially unsaturated or unsaturated;
$R^{14}$ and $R^{15}$ are independently selected from H, methyl, or ethyl; and
$R^{16}$ is a bond, —O— or —S—.

[10] In another alternative embodiment, the present invention provides a compound of Formula (I) or a pharmaceutically acceptable salt or prodrug thereof, wherein:
W is pinanediol boronic ester;
A is $A^2$-$A^3$-$A^4$, $A^2$-$A^3$-$A^4$-$A^5$, or $A^2$-$A^3$-$A^4$-$A^5$-$A^6$;
$A^2$ is Pro, Leu, Asp, Abu, Val, cyclohexylalanine, or

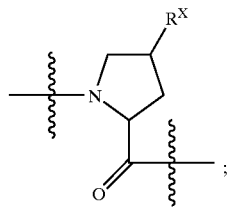

$A^3$ is Val, Glu, Ile, Thr, cyclohexylglycine, or cyclohexylalanine;
$A^4$ is Val, Ile, Leu, cyclohexylglycine, cyclopropylglycine, t-butylglycine, phenylglycine, or 3,3-diphenylalanine;
$A^5$ is Asp, Glu, Val, Ile, t-butylglycine or Gla;
$A^6$ is Asp or Glu;
$R^1$ is —$CH_2CH_2$—$R^{1a}$ or —$CH_2CH_2CH_2CH_2$—$R^{1a}$;
$R^{1a}$ is selected from the group: phenyl, 2-naphthyl, 2-methylphenyl, 3-methylphenyl, 4-methylphenyl, 4-(1,1'-biphenyl)-, 2,5-dimethylphenyl, 2,4-dimethylphenyl, 3-$CF_3$-phenyl, 4-$CF_3$-phenyl, 2-F-phenyl, 3-F-phenyl, 4-F-phenyl, 4-Cl-phenyl, 4-Br-phenyl, 4-phenoxyphenyl, 4-isopropylphenyl, 4-cyclohexylphenyl, 4-tBu-phenyl, 4-methoxyphenyl, 2,6-diF-phenyl, 4-hydroxy-phenyl, (4-methyoxyphenoxy)phenyl, methyl, ethyl, propyl, i-propyl, n-butyl, i-butyl, and cyclobutyl;
$R^X$ is H or benzoxy;
$R^2$ is H;
$R^3$ is H, —C(=O)$R^{11}$ or acetyl;
$R^{11}$ is 5–6 membered heterocyclic ring system consisting of carbon atoms and 1–4 heteroatoms selected from the group: O, S, and N; optionally saturated, partially unsaturated or unsaturated; said 5–6 membered heterocyclic ring system is substituted with 0–2 $R^{11b}$; and
$R^{11b}$ is —$NO_2$, —$NH_2$, —$SO_3H$, —$SO_2CH_3$, —$CO_2H$, —$CF_3$, —OH, —SH, —$OCF_3$, Cl, Br, F, methyl, ethyl, propyl, butyl, —$OCH_3$, or —$OCH_2CH_3$.

It is understood that any and all embodiments of the present invention may be taken in conjunction with any other embodiment to descibe additional even more preferred embodiments of the present invention.

[11] In another alternative embodiment, the present invention provides a compound, or a stereoisomer or a pharmaceutically acceptable salt form or prodrug thereof, selected from:

H-Asp-Glu-Val-Val-Pro-(1R)-1-amino-3-phenylpropylboronic acid (+)-pinanediol ester;
H-Asp-Glu-Val-Val-Pro-(1R)-1-amino-4-phenylbutylboronic acid (+)-pinanediol ester;
H-Asp-Glu-Val-Val-Pro-(1R)-1-amino-5-phenylpentylboronic acid (+)-pinanediol ester;

H-Asp-Glu-Val-Val-Pro-(1R)-1-amino-3-(2-naphthyl)
propylboronic acid (+)-pinanediol ester;
H-Asp-Glu-Val-Val-Pro-(1R)-1-amino-3-(2-methyl)
phenylpropylboronic acid (+)-pinanediol ester;
H-Asp-Glu-Val-Val-Pro-(1R)-1-amino-3-(3-methyl)
phenylpropylboronic acid (+)-pinanediol ester;
H-Asp-Glu-Val-Val-Pro-(1R)-1-amino-3-(4-methyl)
phenylpropylboronic acid (+)-pinanediol ester;
H-Asp-Glu-Val-Val-Pro-(1R)-1-amino-3-(1,1'-biphenyl)-4-
ylpropylboronic acid (+)-pinanediol ester;
H-Asp-Glu-Val-Val-Pro-(1R)-1-amino-3-(2,5-dimethyl)
phenylpropylboronic acid (+)-pinanediol ester;
H-Asp-Glu-Val-Val-Pro-(1R)-1-amino-3-(2,4-dimethyl)
phenylpropylboronic acid (+)-pinanediol ester;
H-Asp-Glu-Val-Val-Pro-(1R)-1-amino-3-(4-trifluoromethyl)phenylpropylboronic acid (+)-pinanediol ester;
H-Asp-Glu-Val-Val-Pro-(1R)-1-amino-3-(3-trifluoromethyl)phenylpropylboronic acid (+)-pinanediol ester;
H-Asp-Glu-Val-Val-Pro-(1R)-1-amino-3-(4-fluoro)
phenylpropylboronic acid (+)-pinanediol ester;
H-Asp-Glu-Val-Val-Pro-(1R)-1-amino-3-(4-phenoxy)
phenylpropylboronic acid (+)-pinanediol ester;
H-Asp-Glu-Val-Val-Pro-(1R)-1-amino-3-(4-isopropyl)
phenylpropylboronic acid (+)-pinanediol ester;
H-Asp-Glu-Val-Val-Pro-(1R)-1-amino-3-(4-cyclohexyl)
phenylpropylboronic acid (+)-pinanediol ester;
H-Asp-Glu-Val-Val-Pro-(1R)-1-amino-3-(4-tert-butyl)
phenylpropylboronic acid (+)-pinanediol ester;
H-Asp-Glu-Val-Val-Pro-(1R)-1-amino-3-(4-methoxy)
phenylpropylboronic acid (+)-pinanediol ester;
H-Asp-Glu-Val-Val-Pro-(1R)-1-amino-3-(4-chloro)
phenylpropylboronic acid (+)-pinanediol ester;
H-Asp-Glu-Val-Val-Pro-(1R)-1-amino-3-(4-bromo)
phenylpropylboronic acid (+)-pinanediol ester;
H-Asp-Glu-Val-Val-Pro-(1R)-1-amino-3-(2-fluoro)
phenylpropylboronic acid (+)-pinanediol ester;
H-Asp-Glu-Val-Val-Pro-(1R)-1-amino-3-(3-fluoro)
phenylpropylboronic acid (+)-pinanediol ester;
H-Asp-Glu-Val-Val-Pro-(1R)-1-amino-3-(2,6-difluoro)
phenylpropylboronic acid (+)-pinanediol ester;
H-Asp-Glu-Val-Val-Pro-(1R)-1-amino-3-(4-hydroxy)
phenylpropylboronic acid (+)-pinanediol ester;
H-Asp-Glu-Val-Val-Pro-(1R)-1-aminohexylboronic acid
(+)-pinanediol ester;
H-Asp-Glu-Val-Val-Pro-(1R)-1-amino-5-methylhexylboronic acid (+)-pinanediol ester;
H-Asp-Glu-Val-Val-Pro-(1R)-1-aminoheptylboronic acid
(+)-pinanediol ester;
H-Asp-Glu-Val-Val-Pro-(1R)-1-amino-4-cyclobutylbutylboronic acid (+)-pinanediol ester; and
H-Asp-Glu-Val-Val-Pro-(1R)-1-amino-5-ethylheptylboronic acid (+)-pinanediol ester.
[12] In another alternative embodiment, the present invention provides a compound, or a stereoisomer or a pharmaceutically acceptable salt form or prodrug thereof, selected from:
Ac-Val-Pro-(1R)-1-amino-3-phenylpropylboronic acid (+)-pinanediol ester;
Ac-Val-Pro-(1R)-1-amino-3-(4-trifluoromethyl)phenyl propylboronic acid (+)-pinanediol ester;
Ac-Val-Pro-(1R)-1-amino-3-(4-phenoxy)
phenylpropylboronic acid (+)-pinanediol ester;
Ac-Val-Pro-(1R)-1-amino-3-(4-hydroxy)
phenylpropylboronic acid (+)-pinanediol ester;
Ac-Val-Pro-(1R)-1-amino-3-(4-(4-methoxyphenoxy)
phenyl) propylboronic acid (+)-pinanediol ester;
Ac-Val-Pro-(1R)-1-amino-3-(4-(4-methylphenoxy)phenyl)
propylboronic acid (+)-pinanediol ester; and
(2-pyrazinecarbonyl)-Val-Val-Hyp(OBn)-(1R)-1-amino-3-(4-trifluoromethyl)phenylpropylboronic acid (+)-pinanediol ester.

This invention also provides compositions comprising one or more of the foregoing compounds and methods of using such compositions in the treatment of hepatitis C virus, such as inhibition of hepatitis C virus protease, in mammals or as reagents used as inhibitors of hepatitis C virus protease in the processing of blood to plasma for diagnostic and other commercial purposes.

In another embodiment, the present invention provides a pharmaceutical composition comprising a compound of Formula (I) and a pharmaceutically acceptable carrier.

In another embodiment, the present invention provides a method of treating a viral infection which comprises administering to a host in need of such treatment a therapeutically effective amount of compounds of Formula (I) or pharmaceutically acceptable salt forms or prodrug thereof.

In another embodiment, the present invention provides A method of treating HCV which comprises administering to a host in need of such treatment a therapeutically effective amount of compounds of Formula (I) or pharmaceutically acceptable salt forms or prodrug thereof.

Definitions

As used throughout the specification, the following abbreviations for amino acid residues or amino acids apply:

Abu is L-aminobutyric acid;
Ala is L-alanine;
Alg is L-2-amino-4-pentenoic acid;
Ape is L-2-aminopentanoic acid;
Arg is L-arginine;
Asn is L-asparagine;
Asp is L-aspartic acid;
Aze is azedine-2-carboxlic acid;
Cha is L-2-amino-3-cyclohexylpropionic acid;
Cpa is L-2-amino-3-cyclopropylpropionic acid
Cpg is L-2-amino-2-cyclopropylacetic acid;
Cys is L-cysteine;
Dfb is L-4,4'-difluoro-1-amino-butyric acid;
Dpa is L-2-amino-3,3-diphenylpropionic acid;
Gla is gamma-carboxyglutamic acid;
Gln is L-glutamine;
Glu is L-glutamic acid;
Gly is glycine;
His is L-histidine;
HomoLys is L-homolysine;
Hyp is L-4-hydroxyproline;
Ile is L-isoleucine;
Irg is isothiouronium analog of L-Arg;
Leu is L-leucine;
Lys is L-lysine;
Met is L-methionine;
Orn is L-ornithine;
Phe is L-phenylalanine;
Phe(4-fluoro) is para-fluorophenylalanine;
Pro is L-proline;
Sar is L-sarcosine;
Ser is L-serine;
Thr is L-threonine;
Tpa is L-2-amino-5,5,5-trifluoropentanoic acid;
Trp is L-tryptophan;
Tyr is L-tyrosine; and
Val is L-valine.

The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic ester. For example, if $R^1$ is isopropyl and $Y^1$ and $Y^2$ are OH, the C-terminal residue is abbreviated "boroVal-OH" where "—OH" indicates the boronic acid is in the form of the free acid. The pinanediol boronic ester and the pinacol boronic ester are abbreviated "—$C_{10}H_{16}$" and "—$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Analogs containing sidechain substituents are described by indicating the substituent in parenthesis following the name of the parent residue. For example the analog of boroPhenylalanine containing a meta cyano group is -boroPhe(mCN)—.

The following abbreviations may also be used herein and are defined as follows. The abbreviation "DIBAL" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate. Other abbreviations are: "BSA", benzene sulfonic acid; "THF", tetrahydrofuran; "DMF", dimethylformamide; "EDCI", 1-dimethylaminopropyl-3-ethylcarbodiimide hydrochloride; "HOAt", 1-hydroxy-7-azabenzotriazole; "DIEA", N,N-diisopropylethylamine; "Boc-", t-butoxycarbonyl-; "Ac-", acetyl; "pNA ", p-nitro-aniline; "DMAP", 4-N,N-dimethylaminopyridine; "Tris", Tris(hydroxymethyl)aminomethane; "PyAOP", 7-azabenzotriazol-1-yloxytris(pyrrolidino)phosphonium hexafluorophosphate; "MS", mass spectrometry; "FAB/MS", fast atom bombardment mass spectrometry. LRMS ($NH_3$—CI) and HRMS($NH_3$—CI) are low and high resolution mass spectrometry, respectively, using $NH_3$ as an ion source.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then two hydrogens on the atom are replaced.

When any variable (e.g., $R^7$ or $R^{13}$) occurs more than one time in any constituent or formula for a compound, its definition at each occurrence is independent of its definition at every other occurrence. Thus, for example, if a group is shown to be substituted with 0–3 $R^{13}$, then said group may optionally be substituted with up to three $R^{13}$ groups and $R^{13}$ at each occurrence is selected independently from the definition of $R^{13}$. Also, combinations of substituents and/or variables are permissible only if such combinations result in stable compounds. By stable compound it is meant herein a compound that is sufficiently robust to survive isolation to a useful degree of purity from a reaction mixture.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In Formula (I) the substituent A is intended to be a peptide of 2 to 6 amino acid residues. For example, the scope of A can be described as $A^2$-$A^3$, $A^2$-$A^3$-$A^4$, $A^2$-$A^3$-$A^4$-$A^5$, $A^2$-$A^3$-$A^4$-$A^5$-$A^6$, $A^2$-$A^3$-$A^4$-$A^5$-$A^6$-$A^7$. Alternatively, A can be described as $(A")_n$ wherein n is 2, 3, 4, 5, or 6. By either description when A is comprised of two amino acid residues or greater, each amino acid residue of A is independently selected apart from each other amino acid residue. For example, $A^2$, $A^3$, $A^4$, $A^5$, $A^6$, and $A^7$ are independently selected from the defined list of possible amino acid residues, including modified or unnatural amino acid residues, disclosed herein. Likewise, each A", when n is 2 or greater, is independently selected from the defined list of possible amino acid residues, including modified or unnatural amino acid residues, disclosed herein.

"Amino acid residue" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,α-disubstituted amino acids. Included in the scope of the present invention are N-alkyl, aryl, and alkylaryl analogs of both in chain and N-terminal amino acid residues. Similarly, alkyl, aryl, and alkylaryl maybe substituted for the alpha hydrogen. Illustrated below are examples of N-alkyl and alpha alkyl amino acid residues, respectively.

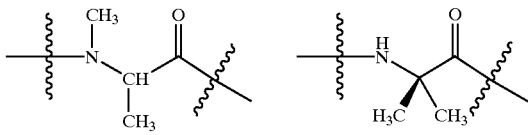

Modified amino acids which can be used to practice the invention include, but are not limited to, D-amino acids, hydroxylysine, 4-hydroxyproline, 3-hydroxyproline, an N-CBZ-protected amino acid, 2,4-diaminobutyric acid, homoarginine, norleucine, N-methylaminobutyric acid, 3,3-diphenylalanine, naphthylalanine, phenylglycine, β-phenylproline, tert-leucine, cyclohexylalanine, 4-aminocyclohexylalanine, N-methyl-norleucine, 3,4-dehydroproline, t-butylglycine, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, 2-benzyl-5-aminopentanoic acid.

Unnatural amino acids that fall within the scope of this invention are by way of example and without limitation: 2-aminobutanoic acid, 2-aminopentanoic acid, 2-aminohexanoic acid, 2-aminoheptanoic acid, 2-aminooctanoic acid, 2-aminononanoic acid, 2-aminodecanoic acid, 2-aminoundecanoic acid, 2-amino-3,3-dimethylbutanoic acid, 2-amino-4,4-dimethylpentanoic acid, 2-amino-3-methylhexanoic acid, 2-amino-3-methylheptanoic acid, 2-amino-3-methyloctanoic acid, 2-amino-3-methylnonanoic acid, 2-amino-4-methylhexanoic acid, 2-amino-3-ethylpentanoic acid, 2-amino-3,4-dimethylpentanoic acid, 2-amino-3,5-dimethylhexanoic acid, 2-amino-3,3-dimethylpentanoic acid, 2-amino-3-ethyl-3-methylpentanoic acid, 2-amino-3,3-diethylpentanoic acid, 2-amino-5-methylhexanoic acid, 2-amino-6-methylheptanoic, 2-amino-7-methyloctanoic, 2-amino-2-cyclopentylacetic, 2-amino-2-clycohexylacetic acid, 2-amino-2-(1-methylcylcohexyl)acetic acid, 2-amino-2-(2-methyl-1-methylcylcohexyl)acetic acid, 2-amino-2-(3-methyl-1-methylcylcohexyl)acetic acid, 2-amino-2-(4-methyl-1-methylcylcohexyl)acetic acid, 2-amino-2-(1-ethylcycolhexyl)acetic acid, 2-amino-3-(cyclohexyl) propanoic acid, 2-amino-4-(cyclohexyl)butanoic acid, 2-amino-3-(1-adamantyl)propanoic acid, 2-amino-3-butenoic acid, 2-amino-3-methyl-3-butenoic acid, 2-amino-4-pentenoic acid, 2-amino-4-hexenoic acid, 2-amino-5-heptenoic acid, 2-amino-4-methyl-4-hexenoic acid, 2-amino-5-methyl-4-hexenoic acid, 2-amino-4-methyl-5-hexenoic acid, 2-amino-6-heptenoic acid, 2-amino-3,3,4-trimethyl-4-pentenoic acid, 2-amino-4-chloro-4-pentenoic, 2-amino-4,4-dichloro-3-butenoic acid, 2-amino-3-(2-methylenecyclopropyl)-propanoic acid, 2-amino-2-(2-cyclopentenyl)acetic acid, 2-amino-2-(cyclohexenyl)acetic acid, 2-amino-3-(2-cyclopentenyl)propanoic acid, 2-amino-3-(3-cyclopentenyl)propanoic acid, 2-amino-3-(1-cyclohexyl)propanoic acid, 2-amino-2-(1-cyclopentenyl) acetic acid, 2-amino-2-(1-cylcohexyl)acetic acid, 2-amino-2-(1-cylcoheptenyl)acetic acid, 2-amino-2-(1-cyclooctenyl) acetic acid, 2-amino-3-(1-cycloheptenyl)propanoic acid, 2-amino-3-(1,4-cyclohexadienyl)propanoic acid, 2-amino-3-(2,5-cyclohexadienyl)propanoic acid, 2-amino-2-(7-cycloheptatrienyl)acetic acid, 2-amino-4,5-hexadienoic acid, 2-amino-3-butynoic acid, 2-amino-4-pentyoic acid, 2-amino-4-hexynoic acid, 2-amino-4-hepten-6-ynoic acid, 2-amino-3-fluoropropanoic acid, 2-amino-3,3,3-trifluoropropanoic acid, 2-amino-3-fluorobutanoic acid, 2-amino-3-fluoropentanoic acid, 2-amino-3-fluorohexanoic acid, 2-amino-3,3-difluorobutanoic acid, 2-amino-3,3-difluoro-3-phenylpropanoic acid, 2-amino-3-perfluoroethylpropanoic acid, 2-amino-3-perfluoropropylpropanoic acid, 2-amino-3-fluoro-3-methylbutanoic acid, 2-amino-5,5,5-trifluoropentanoic acid, 2-amino-3-methyl-4,4,4-trifluorobutanoic acid, 2-amino-3-trifluoromethyl-4,4,4-trifluorobutanoic acid, 2-amino-3,3,4,4,5,5-heptafluoropentanoic acid, 2-amino-3-methyl-5-fluoropentanoic acid, 2-amino-3-methyl-4-fluoropentanoic acid, 2-amino-5,5-difluorohexanoic acid, 2-amino-4-(fluoromethyl)-5-fluoropentanoic acid, 2-amino-4-trifluoromethyl-5,5,5-trifluoropentanoic acid, 2-amino-3-fluoro-3-methylbutanoic acid, 2-amino-3-fluoro-3-phenylpentanoic acid, 2-amino-2-(1-fluorocyclopentyl) acetic acid, 2-amino-2-(1-fluorocyclohexyl)acetic acid, 2-amino-3-chloropropanoic acid acid, 2-amino-3-chlorobutanoic acid acid, 2-amino-4,4-dichlorobutanoic acid acid, 2-amino4,4-trichlorobutanoic acid acid, 2-amino-3,4,4-trichlorobutanoic acid, 2-amino-6-chlorohexanoic acid, 2-amino-4-bromobutanoic acid, 2-amino-3-bromobutanoic acid, 2-amino-3-mercaptobutanoic acid, 2-amino-4-mercaptobutanoic acid, 2-amino-3-mercapto-3,3-dimethylpropanoic acid, 2-amino-3-mercapto-3-methylpentanoic acid, 2-amino-3-mercaptopentanoic acid, 2-amino-3-mercapto-4-methylpentanoic acid, 2-amino-3-methyl-4-mercaptopentanoic acid, 2-amino-5-mercapto-5-methylhexanoic acid, 2-amino-2-(1-mercaptocyclobutyl) acetic acid, 2-amino-2-(1-mercaptocyclopentyl)acetic acid, 2-amino-2-(1-mercaptocyclohexyl)acetic acid, 2-amino-5-(methylthio)pentanoic acid, 2-amino-6-(methylthio) hexanoic acid, 2-amino-4-methylthio-3-phenylbutanoic acid, 2-amino-5-ethylthio-5-methylpentanoic acid, 2-amino-5-ethylthio-3,5,5-trimethylpentanoic acid, 2-amino-5-ethylthio-5-phenylpentanoic acid, 2-amino-5-ethylthio-5-pentanoic acid, 2-amino-5-butylthio-5-methylpentanoic acid, 2-amino-5-butylthio-3,5,5-trimethylpentanoic acid, 2-amino-5-butylthio-5-phenylpentanoic acid, 2-amino-5-(butylthio)pentanoic acid, 2-amino-3-methyl4-hydroselenopentanoic acid, 2-amino-4-methylselenobutanoic acid, 2-amino-4-ethylselenobutanoic acid, 2-amino-4-benzylselenobutanoic acid, 2-amino-3-methyl-4-(methylseleno)butanoic acid, 2-amino-3-(aminomethylseleno)propanoic acid, 2-amino-3-(3-aminopropylseleno)propanoic acid, 2-amino-4-methyltellurobutanoic acid, 2-amino-4-hydroxybutanoic acid, 2-amino-4-hydroxyhexanoic acid, 2-amino-3-hydroxypentanoic acid, 2-amino-3-hydroxyhexanoic acid, 2-amino-3methyl-4-hydroxybutanoic acid, 2-amino-3-hydroxy-3-methylbutanoic acid, 2-amino-6-hydroxyhexanoic acid, 2-amino-4-hydroxyhexanoic acid, 2-amino-3-hydroxy-4-methylpentanoic acid, 2-amino-3-hydroxy-3-methylpentanoic acid, 2-amino4-hydroxy-3,3-dimethylbutanoic acid, 2-amino-3-hydroxy4-methylpentanoic acid, 2-amino-3-hydroybutanedioic acid, 2-amino-3-hydroxy-3-phenyl-propanoic acid, 2-amino-3-hydroxy-3-(4-nitrophenyl)propanoic acid, 2-amino-3-hydroxy-3-(3-pyridyl)propanoic acid, 2-amino-2-(1-hydroxycyclopropyl)acetic acid, 2-amino-3-(1-hydroxycyclohexyl)propanoic acid, 2-amino-3-hydroxy-3-phenylpropanoic acid, 2-amino-3-hydroxy-3-[3-bis(2-chloroethyl)aminophenyl]propanoic acid, 2-amino-3-hydroxy-3-(3,4-dihydroxyphenyl)propanoic acid, 2-amino-3-hydroxy-3-(3,4-methylenedioxyphenyl)propanoic acid, 2-amino-4-fluoro-3-hydroxybutanoic acid, 2-amino-4,4,4-trichloro-3-hydroxybutanoic acid, 2-amino-3-hydroxy-4-hexynoic acid, 2-amino-3,4-dihydroxybutanoic acid, 2-amino-3,4,5,6-tetrahydroxyhexanoic acid, 2-amino-4,5-dihydroxy-3-methylpentanoic acid, 2-amino-5,6-dihydroxyhexanoic acid, 2-amino-5-hydroxy-4-(hydroxymethyl)pentanoic acid, 2-amino-4,5-dihydroxy-4-(hydroxymethyl)pentanoic acid, 2-amino-3-hydroxy-5-benzyloxypentanoic acid, 2-amino-3-(2-aminoethoxy)propanoic acid, 2-amino-4-(2-aminoethoxy)butanoic acid, 2-amino-4-oxobutanoic acid, 2-amino-3-oxobutanoic acid, 2-amino-4-methyl-3-oxopentanoic acid, 2-amino-3-phenyl-3-oxopropanoic acid, 2-amino-4-phenyl-3-oxobutanoic acid, 2-amino-3-methyl-4-oxopentanoic acid, 2-amino-4-oxo-4-(4-hydroxyphenyl)butanoic acid, 2-amino-4-oxo-4-(2-furyl)butanoic acid, 2-amino-4-oxo-4-(2-nitrophenyl)butanoic acid, 2-amino-4-oxo-4-(2-amino-4-chlorophenyl)butanoic acid, 2-amino-3-(4-oxo-1-cyclohexenyl)propanoic acid, 2-amino-3-(4-oxocyclohexanyl)propanoic acid, 2-amino-3-(2,5-dimethyl-3,6-dioxo-1,4-cydohexadienyl)propanoic acid, 2-amino-3-(1-hydroxy-5-methyl-7-oxo-cyclohepta-1,3,5-trien-2-yl)propanoic acid, 2-amino-3-(1-hydroxy-7-oxo-cyclohepta-1,3,5-trien-3-yl)propanoic acid, 2-amino-3-(1-hydroxy-7-oxo-cyclohepta-1,3,5-trien-4-yl)propanoic acid, 2-amino-4-methoxy-3-butenoic acid, 2-amino-4-(2-aminoethoxy)-3-butenoic acid, 2-amino-4-(2-amino-3-hydroxypropyl)-3-butenoic acid, 2-amino-2-(4-methoxy-1,4-cyclohexadienyl)acetic acid, 2-amino-3,3-diethoxypropanoic acid, 2-amino-4,4-dimethylbutanoic acid, 2-amino-2-(2,3-epoxycyclohexyl)acetic acid, 2-amino-3-(2,3-epoxycyclohexy)propanoic acid, 2-amino-8-oxo-9,10-epoxydecanoic acid, 2-amino-propanedioic acid, 2-amino-3-methylbutanedioic acid, 2-amino-3,3-dimethylbutanedioic acid, 2-amino4-methylpentanedioic acid, 2-amino-3-methylpentanedioic acid, 2-amino-3-phenylpentanedioic acid, 2-amino-3-hydroxypentanedioic acid, 2-amino-3-carboxypentanedioic acid, 2-amino-4-ethylpentanedioic acid, 2-amino-4-propylpentanedioic acid, 2-amino-4-isoamylpentanedioic acid, 2-amino-4-phenylpentanedioic acid, 2-amino-hexanedioic acid, 2-amino-heptanedioic acid, 2-amino-decanedioic acid, 2-amino-octanedioic acid, 2-amino-dodecanedioic acid, 2-amino-3-methylenebutanedioic acid, 2-amino-3-methylenepentanedioic acid, 2-amino-3-fluorobutanedioic acid, 2-amino-4-fluoropentanedioic acid, 2-amino-3,3-difluorobutanedioic acid, 2-amino-3-chloropentanedioic acid, 2-amino-3-hydroxybutanedioic acid, 2-amino-4-hydroxypentanedioic acid, 2-amino-4-hydroxyhexanedioic acid, 2-amino-3,4-dihydroxypentanedioic acid, 2-amino-3-(3-hydroxypropyl)butanedioic acid, 2-amino-3-(1-carboxy-4-hydroxy-2-cyclodienyl)propanoic acid, 2-amino-3-(aceto)butanedioic acid, 2-amino-3-cyanobutanedioic acid, 2-amino-3-(2-carboxy-6-oxo-6H-pyranyl)propanoic acid, 2-amino-3-carboxybutanedioic acid, 2-amino-4-carboxypentanedioic acid, 3-amido-2-amino-3-hydroxypropanoic acid, 3-arnido-2-amino-3-methylpropanoic acid, 3-amido-2-amino-3-phenylpropanoic acid, 3-amido-2,3-diaminopropanoic acid, 3-amido-2-amino-3-[N-(4-hydroxyphenyl)amino]propanoic acid, 2,3-diaminopropanoic acid, 2,3-diaminobutanoic acid, 2,4-diaminobutanoic acid, 2,4-diamino-3-methylbutanoic acid, 2,4-diamino-3-phenylbutanoic acid, 2,4-diamino-3-(methylamino)butanoic acid, 2,5-diamino-3-methylpentanoic acid, 2,7-diaminoheptanoic acid, 2,4-diaminoheptanoic acid, 2-amino-2-(2-piperidyl)acetic acid, 2-amino-2-(1-aminocyclohexyl)acetic acid, 2,3-diamino-3-phenylpropanoic acid, 2,3-diamino-3-(4-hydroxyphenyl)propanoic acid, 2,3-diamino-3-(4-methoxyphenyl)propanoic acid, 2,3-diamino-3-[4-(N,N'-dimethyamino)phenyl]propanoic acid, 2,3-diamino-3-(3,4-dimethoxyphenyl)propanoic acid, 2,3-diamino-3-(3,4-methylenedioxyphenyl)propanoic acid, 2,3-diamino-3-(4-hydroxy-3-methoxyphenyl)propanoic acid, 2,3-diamino-3-(2-phenylethyl)propanoic acid, 2,3-diamino-3-propylpropanoic acid, 2,6-diamino-4-hexenoic acid, 2,5-diamino-4-fluoropentanoic acid, 2,6-diamino-5-fluorohexanoic acid, 2,6-diamino-4-hexynoic acid, 2,6-diamino-5,5-difluorohexanoic acid, 2,6-diamino-5,5-dimethylhexanoic acid, 2,5-diamino-3-hydroxypentanoic acid, 2,6-diamino-3-hydroxyhexanoic acid, 2,5-diamino-4-hydroxypentanoic acid, 2,6-diamino-4-hydroxyhexanoic acid, 2,6-diamino-4-oxohexanoic acid, 2,7-diaminooctanedioic acid, 2,6-diamino-3-carboxyhexanoic acid, 2,5-diamino-4-carboxypentanoic acid, 2-amino-4-(2-(N,N'-diethylamino)ethyl)pentandioic acid, 2-amino-4-(N,N'-diethylamino)pentandioic acid, 2-amino-4-(N-morpholino)pentandioic acid, 2-amino-4-(N,N'-bis(2-chloroethyl)amino)pentandioic acid, 2-amino-4-(N,N'-bis(2-hydroxyethyl)amino)pentandioic acid, 2,3,5-triaminopentanoic acid, 2-amino-3-(N-(2-aminethyl)amino)propanoic acid, 2-amino-3-((2-aminoethyl)seleno)propanoic acid, 2-amino-3-[(2-aminoethyl)thio]propanoic acid, 2-amino4-aminooxybutanoic acid, 2-amino-5-hydroxyaminopentanoic acid, 2-amino-5-[N-(5-nitro-2-pyrimidinyl)amino]pentanoic acid, 2-amino-4-[(7-nitro-2,1,3-benzoxadiazol-4-yl)amino]butanoic acid, 2-amino-3-guanidinopropanoic acid, 2-amino-3-guanidinobutanoic acid, 2-amino-4-guanidobutanoic acid, 2-amino-6-guanidohexanoic acid, 2-amino-6-ureidohexanoic acid, 2-amino-3-(2-iminoimidazolin-4-yl)propanoic acid, 2-amino-2-(2-iminohexahydropyrimidin-4-yl)acetic acid, 2-amino-3-(2-iminohexahydropyrimidiny-4-yl)propanoic acid, 2-amino4-fluoro-5-guanidopentanoic acid, 2-amino-4-hydroxy-5-guanidopentanoic acid, 2-amino-4-guanidooxybutanoic acid, 2-amino-6-amidinohexanoic acid, 2-amino-5-(N-acetimidoylamino) pentanoic acid, 1-aminocyclopropanecarboxylic acid, 1-amino-4-ethylcyclpropanecarboxylic acid, 1-aminocyclopentanecarboxylic acid, 1-aminocyclopentanecarboxylic acid, 1-amino-2,2,5,5-tetramethyl-cyclohexanecarboxylic acid, 1-aminocydoheptanecarboxylic acid, 1-aminocyclononanecarboxylic acid, 2-aminoindan-2-carboxylic acid, 2-aminonorbornane-2-carboxylic acid, 2-amino-3-phenylnorbornane-2-carboxylic acid, 3-aminotetrahydrothiophene-3-carboxylic acid, 1-amino-i,3-cyclohexanedicarboxylic acid, 3-aminopyrrolidine-3-carboxylic acid, 1,4-diaminocyclohexanecarboxylic acid, 6-alkoxy-3-amino-1,2,3,4-tetrahydrocarbazole-3-carboxylic acid, 2-aminobenzobicyclo[2,2,2]octane-2-carboxylic acid, 2-aminoindan-2-carboxylic acid, 1-amino-2-(3,4-dhydroxyphenyl) cyclopropanecarboxylic acid, 5,6-dialkoxy-2-aminoindane-2-carboxylic acid, 4,5-dihydroxy-2-aminoindan-2-caroxylic acid, 5,6-dihydroxy-2-aminotetralin-2-carboxylic acid, 2-amino-2-cyanoacetic acid, 2-amino-3-cyanopropanoic acid, 2-amino-4-cyanobutanoic acid, 2-amino-5-nitropentanoic acid, 2-amino-6-nitrohexanoic acid, 2-amino-4-aminooxybutanoic acid, 2-amino-3-(N-nitrosohydroxyamino) propanoic acid, 2-amino-3-ureidopropanoic acid, 2-amino-4-ureidobutanoic acid, 2-amino-3-phosphopropanoic acid, 2-amino-3-thiophosphopropanoic acid, 2-amino-4-methanephosphonylbutanoic acid, 2-amino-3-

(trimethylsilyl)propanoic acid, 2-amino-3-(dimethyl (trimethylsilylmethylsilyl)propanoic acid, 2-amino-2-phenylacetic acid, 2-amino-2-(3-chlorophenyl) acetic acid, 2-amino-2-(4-chlorophenyl)acetic acid, 2-amino-2-(3-fluorophenyl)acetic acid, 2-amino-2-(3-methylphenyl) acetic acid, 2-amino-2-(4of luorophenyl)acetic acid, 2-amino-2-(4-methylphenyl)acetic acid, 2-amino-2-(4-nethoxyphenyl) acetic acid, 2-amino-2-(2-fluorophenyl) acetic acid, 2-amino-2-(2-methylphenyl)acetic acid, 2-amino-2-(4-chloromethylphenyl)acetic acid, 2-amino-2-(4-hydroxymethylphenyl)acetic acid, 2-amino-2-[4-(methylthiomethyl)phenyl]acetic acid, 2-amino-2-(4-bromomethylphenyl)acetic acid, 2-amino-2-(4-(methoxymethy)phenyl)acetic acid, 2-amino-2-(4-((N-benzylamino)methyl)phenyl)acetic acid, 2-amino-2-(4-hydroxylphenyl)acetic acid, 2-amino-2-(3-hydroxylphenyl) acetic acid, 2-amino-2-(3-carboxyphenyl)acetic acid, 2-amino-2-(4-aminophenyl)acetic acid, 2-amino-2-(4-azidophenyl)acetic acid, 2-amino-2-(3-t-butyl-4-hydroxyphenyl)acetic acid, 2-amino-2-(3,5-difluoro-4-hydroxyphenyl)acetic acid, 2-amino-2-(3,5-dihydroxyphenyl)acetic acid, 2-amino-2-(3-carboxy-4-hydroxyphenyl)acetic acid, 2-amino-2-(3,5-di-t-butyl-4-hydroxyphenyl)acetic acid, 2-amino-3-(2-methylphenyl) propanoic acid, 2-amino-3-(4-ethylphenyl)propanoic acid, 2-amino-3-(4-phenylphenyl)propanoic acid, 2-amino-3-(4-benzylphenyl)propanoic acid, 2-amino-3-(3-fluorophenyl) propanoic acid, 2-amino-3-(4-methylphenyl)propanoic acid, 2-amino-3-(4-fluorophenyl)propanoic acid, 2-amino-3-(4-chlorophenyl)propanoic acid, 2-amino-3-(2-chlorophenyl) propanoic acid, 2-amino-3-(4-bromophenyl)propanoic acid, 2-amino-3-(2-b3bromophenyl)propanoic acid, 2-amino-3-(3-hydroxyphenyl)propanoic acid, 2-amino-3-(2-hydroxyphenyl)propanoic acid, 2-amino-3-(4-mercaptophenyl)propanoic acid, 2-amino-3-(3-trifluoromethylphenyl)propanoic acid, 2-amino-3-(3-hydroxyphenyl)propanoic acid, 2-amino-3-(4-hydroxyphenyl)propanoic acid, 2-amino-3-[4-(hydroxymethyl)phenyl]propanoic acid, 2-amino -3-[3-(hydroxymethyl)phenyl]propanoic acid, 2-amino-3-[3-(aminomethyl)phenyl]propanoic acid, 2-amino-3-(3-carboxyphenyl)propanoic acid, 2-amino-3-(4-nitrophenyl) propanoic acid, 2-amino-3-(4-aminophenyl)propanoic acid, 2-amino-3-(4-azidophenyl)propanoic acid, 2-amino-3-(4-cyanophenyl)propanoic acid, 2-amino-3-(4-acetophenyl) propanoic acid, 2-amino-3-(4-guanidinophenyl)propanoic acid, 2-amino-3-[4-(phenylazo)phenyl]propanoic acid, 2-amino-3-[4-(2-phenylethylenyl)phenyl]propanoic acid, 2-amino-3-(4-trialkylsilylphenyl)propanoic acid, 2-amino-3-(2,4-dimethylphenyl)propanoic acid, 2-amino-3-(2,3-dimethylphenyl)propanoic acid, 2-amino-3-(2,5-dimethylphenyl)propanoic acid, 2-amino-3-(3,5-dimethylphenyl)propanoic acid, 2-amino-3-(2,4,6-trimethylphenyl)propanoic acid, 2-amino-3-(3,4,5-trimethylphenyl)propanoic acid, 2-amino-3-(2,3,4,5,6-pentamethylphenyl)propanoic acid, 2-amino-3-(2,4,-difluorophenyl)propanoic acid, 2-amino-3-(3,4,-difluorophenyl)propanoic acid, 2-amino-3-(2,5,-difluorophenyl)propanoic acid, 2-amino-3-(2,6,-difluorophenyl)propanoic acid, 2-amino-3-(2,3,5,6-tetrafluorophenyl)propanoic acid, 2-amino-3-(3,5-dichloro-2,4,6-trifluorophenyl)propanoic acid, 2-amino-3-(2,3-difluorophenyl)propanoic acid, 2-amino-3-(2,3-bistrifluoromethylphenyl)propanoic acid, 2-amino-3-(2,4-bistrifluoromethylphenyl)propanoic acid, 2-amino-3-(2-chloro-5-trifluoromethylphenyl)propanoic acid, 2-amino-3-(2,5-difluorophenyl)propanoic acid, 2-amino-3-(2,3,4,5,6-pentafluorophenyl)propanoic acid, 2-amino-3-(2,3-dibromophenyl)propanoic acid, 2-amino-3-(2,5-dibromophenyl)propanoic acid, 2-amino-3-(3,4-dibromophenyl)propanoic acid, 2-amino-3-(3,4,5-triiodophenyl)propanoic acid, 2-amino-3-(2,3-dihydroxyphenyl)propanoic acid, 2-amino-3-(2,5-dihydroxyphenyl)propanoic acid, 2-amino-3-(2,6-dihydroxyphenyl)propanoic acid, 2-amino-3-(3-bromo-5-methoxyphenyl)propanoic acid, 2-amino-3-(2,5-dimethoxyphenyl)propanoic acid, 2-amino-3-(2,5-dimethoxy-4-methylphenyl)propanoic acid, 2-amino-3-(4-bromo-2,5-dimethoxyphenyl)propanoic acid, 2-amino-3-(3-carboxy-4-hydroxyphenyl)propanoic acid, 2-amino-3-(3-carboxy-4-aminophenyl)propanoic acid, 2-amino-3-(2-hydroxy-5-nitrophenyl)propanoic acid, 2-amino-3-(2-ethoxy-5-nitrophenyl)propanoic acid, 2-amino-3-(3,4,5-trimethoxyphenyl)propanoic acid, 2-amino-3-(4-azido-2-nitrophenyl)propanoic acid, 2-amino-3-(2-hydroxy-5-nitrophenyl)propanoic acid, 2-amino-3-(2,4-bis-trimethylsilylphenyl)propanoic acid, 2-amino-3-(4-hydroxy-3,5-di-t-butylphenyl)propanoic acid, 2-amino-3-(4-hydroxy-3-benzylphenyl)propanoic acid, 2-amino-3-(4-hydroxy-3-fluorophenyl)propanoic acid, 2-amino-3-(4-hydroxy-2,3,5,6-tetrafluorophenyl)propanoic acid, 2-amino-3-(4-hydroxy-3,5-dichlorophenyl)propanoic acid, 2-amino-3-(4-hydroxy-3-iodophenyl)propanoic acid, 2-amino-3-(4-hydroxy-3,5-diiodophenyl)propanoic acid, 2-amino-3-(4-hydroxy-2-hydroxyphenyl)propanoic acid, 2-amino-3-(4-hydroxy thyronines, 2-amino-3-(3,4-dihydroxy-2-chlorophenyl)propanoic acid, 2-amino-3-(3,4-dihydroxy-2-bromophenyl)propanoic acid, 2-amino-3-(3,4-dihydroxy-2-fluorophenyl)propanoic acid, 2-amino-3-(3,4-dihydroxy-2-nitrophenyl)propanoic acid, 2-amino-3-(3,4-dihydroxy-2-methylphenyl)propanoic acid, 2-amino-3-(3,4-dihydroxy-2-ethylphenyl)propanoic acid, 2-amino-3-(3,4-dihydroxy-2-isopropylphenyl)propanoic acid, 2-amino-3-(2-t-butyl-4,5-dihydroxyphenyl)propanoic acid, 2-amino-3-(3-fluoro-4,5-dihydroxyphenyl)propanoic acid, 2-amino-3-(2-fluoro-4,5-dihydroxyphenyl)propanoic acid, 2-amino-3-(2,5,6-trifluoro-3,4-dihydroxyphenyl)propanoic acid, 2-amino-3-(2,6-dibromo-3,4-dihydroxyphenyl)propanoic acid, 2-amino-3-(5,6-dibromo-3,4-dihydroxyphenyl)propanoic acid, 2-amino-3-(2,4,5-trihydroxyphenyl)propanoic acid, 2-amino-3-(2,3,4-trihydroxyphenyl)propanoic acid, 2-amino-3-(3,4-dihydroxy-5-methoxyphenyl)propanoic acid, 2-amino-3-methyl-3-phenylpropanoic acid, 2-amino-3-ethyl-3-phenylpropanoic acid, 2-amino-3-isopropyl-3-phenylpropanoic acid, 2-amino-3-butyl-3-phenylpropanoic acid, 2-amino-3-benzyl-3-phenylpropanoic acid, 2-amino-3-phenylethyl-3-phenylpropanoic acid, 2-amino-3-(4-chlorophenyl)-3-phenylpropanoic acid, 2-amino-3-(4-methoxyphenyl)-3-phenylpropanoic acid, 2-amino-3,3-diphenylpropanoic acid, 2-amino-3-[4-(N,N-diethylamino)phenyl]heptanoic acid, 2-amino-3-[4-(N,N-diethylamino)phenyl]pentanoic acid, 2-amino-3-(3,4-dimethoxyphenyl) pentanoic acid, 2-amino-3-(3,4-dihydroxyphenyl)pentanoic acid, 2-amino-3-methyl-3-phenylbutanoic acid, 2-amino-3-ethyl-3-phenylpentanoic acid, 2-amino-3-methyl-3-phenylpentanoic acid, 2-amino-3,3-diphenylbutanoic acid, 2-amino-3-fluoro-3-phenylpropanoic acid, 2-amino-3-methylene-3-phenylpropanoic acid, 2-amino-3-methylmercapto-3-phenylpropanoic acid, 2-amino-4-methylmercapto-4-phenylbutanoic acid, 2-amino-4-(3,4-dihydroxyphenyl)butanoic acid, 2-amino-4-((4-methoxyphenyl)pentanoic acid, 2-amino-4-phenylbutanoic acid, 2-amino-5-phenylpentanoic acid, 2-amino-3,3-dimethyl-5-phenylpentanoic acid, 2-amino-4-phenyl-3- butenoic acid, 2-amino-4-phenoxybutanoic acid, 2-amino-5-phenoxypentanoic acid, 2-amino-2-(indanyl)acetic acid, 2-amino-2-(1-tetralyl)acetic acid, 2-amino-4,4-diphenylbutanoic acid, 2-amino-2-(2-naphthyl)acetic acid, 2-amino-3-(2-naphthyl)propanoic acid, 2-amino-3-(1-naphthyl)pentanoic acid, 2-amino-3-(2-naphthyl)propanoic acid, 2-amino-3-(1-chloro-2-naphthyl)propanoic acid, 2-amino-3-(1-bromo-2-naphthyl)propanoic acid, 2-amino-3-(4-hydroxy-1-naphthyl)propanoic acid, 2-amino-3-(4-methoxy-1-naphthyl)propanoic acid, 2-amino-3-(4-hydroxy-2-chloro-1-naphthyl)propanoic acid, 2-amino-3-(2-chloro-4-methoxy-1-naphthyl)propanoic acid, 2-amino-2-(2-anthryl)acetic acid, 2-amino-3-(9-anthryl)propanoic acid, 2-amino-3-(2-fluorenyl)propanoic acid, 2-amino-3-(4-fluorenyl)propanoic acid, 2-amino-3-(carboranyl)propanoic acid, 3-methylproline, 4-methylproline, 5-methylproline, 4,4-dimethylproline, 4-fluoroproline, 4,4-difluoroproline, 4-bromoproline, 4-chloroproline, 3,4-dehydroproline, 4-methylproline, 4-methyleneproline, 4-mercaptoproline, 4-(4-methoxybenzylmercapto)proline, 4-hydroxymethylproline, 3-hydroxyproline, 3-hydroxy-5-methylproline, 3,4-dihydroxyproline, 3-phenoxyproline, 3-carbamylalkylproline, 4-cyano-5-methyl-5-carboxyproline, 4,5-dicarboxy-5-methylproline, 2-aziridinecarboxylic acid, 2-azetidinecarboxylic acid, 4-methyl-2-azetidinecarboxylic acid, pipecolic acid, 1,2,3,6-tetrahydropicolinic acid, 3,4-methyleneproline, 2.4-methyleneproline, 4-aminopipecolic acid, 5-hydroxypipecolic acid, 4,5-dihydroxypipecolic acid, 5,6-dihydroxy-2,3-dihydroindole-2-carboxylic acid, 1,2,3,4-tetrahydroquinoline-2-carboxylic acid, 6,7-dihydroxy-1,2,3,4-tetrahydroisoquinoline-3-carboxylic acid, 6-hydroxy-1-methyl-1,2,3,4-tetrahydroisoquinoline-3-carboxylic acid, 6,7-dihydroxy-1-methyl-1,2,3,4-tetrahydroisoquinoline-3-carboxylic acid, 1,3-oxazolidine-4-carboxylic acid, 1,2-oxazolidine-3-carboxylic acid, perhydro-1,4-thiazine-3-carboxylic acid, 2,2-dimethylthiazolidine-4-carboxylic acid, perhydro-1,3-thlazine-2-carboxylic acid, selenazolidine4-carboxylic acid, 2-phenylthiazolidine4-carboxylic acid, 2-(4-carboxylicyl)thiazolidine-4-carboxylic acid, 1,2,3,4,4a,9a-hexahydro-beta-carboline-3-carboxylic acid, 2,3,3a,8a-tetrahydropyrrolo(2,3b)indole-2-carboxylic acid, 2-amino-3-(2-pyridyl)propanoic acid, 2-amino-3-(3-pyridyl)propanoic acid, 2-amino-3-(4-pyridyl)propanoic acid, 2-amino-3-(2-bromo-3-pyridyl)propanoic acid, 2-amino-3-(2-bromo-4-pyridyl)propanoic acid, 2-amino-3-(2-bromo-5-pyridyl)propanoic acid, 2-amino-3-(2-bromo-6-pyridyl)propanoic acid, 2-amino-3-(2-chloro-3-pyridyl)propanoic acid, 2-amino-3-(2-chloro-4-pyridyl)propanoic acid, 2-amino-3-(2-chloro-5-pyridyl)propanoic acid, 2-amino-3-(2-chloro-6-pyridyl)propanoic acid, 2-amino-3-(2-fluoro-3-pyridyl)propanoic acid, 2-amino-3-(2-fluoro-4-pyridyl)propanoic acid, 2-amino-3-(2-fluoro-5-pyridyl)propanoic acid, 2-amino-3-(2-fluoro-6-pyridyl)propanoic acid, 2-amino-3-(1,2-dihydro-2-oxo-3-pyridyl)propanoic acid, 2-amino-3-(1,2-dihydro-2-oxo4-pyridyl)propanoic acid, 2-amino-3-(1,2-dihydro-2-oxo-5-pyridyl)propanoic acid, 2-amino-3-(1,2-dihydro-2-oxo-6-pyridyl)propanoic acid, 2-amino-3-(5-hydroxy-2-pyridyl)propanoic acid, 2-amino-3-(5-hydroxy-6-iodo-2-pyridyl)propanoic acid, 2-amino-3-(3-hydroxy-4-oxo-1,4dihydro-1-pyridyl)propanoic acid, N-(5-caroxyl-5-aminopentyl)pyridinium chloride, 1,2,5-trimethyl-4-(2-amino-2-carboxy-1-hydroxyethyl)pyridinium chloride, 2-amino-2-(5-chloro-2-pyridyl)acetic acid, N-(3-amino-3-carboxypropyl)pyridinium chloride, 2-amino-3-(2-pyrryl)propanoic acid, 2-amino-3-(1-pyrryl)propanoic acid, 2-amino-4-(1-pyrryl)butanoic acid, 2-amino-5-(1-pyrryl)pentanoic acid, 2-amino-3-(5-imidazolyl)-3-methylpropanoic acid, 2-amino-3-(5-imidazolyl)-3-ethylpropanoic acid, 2-amino-3-hexyl-3-(5-imidazolyl)propanoic acid, 2-amino-3-hydroxy-3-(5-imidazolyl)propanoic acid, 2-amino-3-(4-nitro-5-imidazolyl)proloanoic acid, 2-amino-3-(4-methyl-5-imidazolyl)propanoic acid, 2-amino-3-(2-methyl-5-imidazolyl)propanoic acid, 2-amino-3-(4-fluoro-5-imidazolyl)propanoic acid, 2-amino-3-(2-fluoro-5-imidazolyl)propanoic acid, 2-amino-3-(2-amino-5-imidazolyl)propanoic acid, 2-amino-3-(2-phenylaza-5-imidazolyl)propanoic acid, 2-amino-3-(1-methyl-2-nitro-5-imidazolyl)propanoic acid, 2-amino-3-(1-methyl4-nitro-5-imidazolyl)propanoic acid, 2-amino-3-(1-methyl-4-nitro-5-imidazolyl)propanoic acid, 2-amino-3-(2-mercapto-5-imidazolyl)propanoic acid, 2-amino-4-(5-imidazolyl)butanoic acid, 2-amino-3-(1-imidazolyl)propanoic acid, 2-amino-3-(2-imidazolyl)propanoic acid, 2-amino-(1-pyrazolyl)propanoic acid, 2-amino-(3-pyrazolyl)propanoic acid, 2-amino-(3,5-dialkyl-4-pyrazolyl)propanoic acid, 2-amino-3-(3-amino-1,2,4-triazol-1-yl)propanoic acid, 2-amino-3-(tetrazol-5-yl)propanoic acid, 2-amino-4-(5-tetrazolyl)butanoic acid, 2-amino-3-(6-methyl-3-indolyl)propanoic acid, 2-amino-3-(4-fluoro-3-indolyl)propanoic acid, 2-amino-3-(5-fluoro-3-indolyl)propanoic acid, 2-amino-3-(6-fluoro-3-indolyl)propanoic acid, 2-amino-3-(4,5,6,7-tetrafluoro-3-indolyl)propanoic acid, 2-amino-3-(5-chloro-3-indolyl)propanoic acid, 2-amino-3-(6-chloro-3-indolyl)propanoic acid, 2-amino-3-(7-chloro-3-indolyl)propanoic acid, 2-amino-3-(5-bromo-3-indolyl)propanoic acid, 2-amino-3-(7-bromo-3-indolyl)propanoic acid, 2-amino-3-(2-hydroxy-3-indolyl)propanoic acid, 2-amino-3-(5-hydroxy-3-indolyl)propanoic acid, 2-amino-3-(7-hydroxy-3-indolyl)propanoic acid, 2-amino-3-(2-alkylmercapto-3-indolyl)propanoic acid, 2-amino-3-(7-amino-3-indolyl)propanoic acid, 2-amino-3-(4-nitro-3-indolyl)propanoic acid, 2-amino-3-(7-nitro-3-indolyl)propanoic acid, 2-amino-3-(4-carboxy-3-indolyl)propanoic acid, 2-amino-3-(3-indolyl)butanoic acid, 2-amino-3-(2,3-dihydro-3-indolyl)propanoic acid, 2-amino-3-(2,3-dihydro-2-oxo-3-indolyl)propanoic acid, 2-amino-3-alkylmercapto-3-(3-indolyl)propanoic acid, 2-amino-3-(4-aza-3-indolyl)propanoic acid, 2-amino-3-(7-aza-3-indolyl)propanoic acid, 2-amino-3-(7-aza-6-chloro-4-methyl-3-indolyl)propanoic acid, 2-amino-3-(2,3-dihydrobenzofuran-3-yl)propanoic acid, 2-amino-3-(3-methyl-5–7-dialkylbenzofuran-2-yl)propanoic acid, 2-amino-3-(benzothiophen-3-yl)propanoic acid, 2-amino-3-(5-hydroxybenzothiophen-3-yl)propanoic acid, 2-amino-3-eoenzoselenol-3yl)propanoic acid, 2-amino-3-quinolylpropanoic acid, 2-amino-3-(8-hydroxy-5-quinolyl)propanoic acid, 2-amino-2-(5,6,7,8-tetrahydroquinol-5-yl)acetic acid, 2-amino-3-(3-coumarinyl)propanoic acid, 2-amino-2-(benzisoxazol-3-yl)acetic acid, 2-amino-2-(5-methylbenzisoxazol-3-yl)acetic acid, 2-amino-2-(6-methylbenzisoxazol-3-yl)acetic acid, 2-amino-2-(7-methylbenzisoxazol-3-yl)acetic acid, 2-amino-2-(5-bromobenzisoxazol-3-yl)acetic acid, 2-amino-3-(benzimidazol-2-yl)propanoic acid, 2-amino-3-(5,6-dichlorobenzimidazol-2-yl)propanoic acid, 2-amino-3-(5,6-dimethylbenzimidazol-2-yl)propanoic acid, 2-amino-3-(4,5,6,7-hydrobenzimidazol-2-yl)propanoic acid, 2-amino-2-(benzimidazol-5-yl)acetic acid, 2-amino-2-(1,3-dihydro-2,2-dioxoisobenzothiophen-5-yl)acetic acid, 2-amino-2-(1, 3-dihydro-2,2-dioxo-2,1,3-benzothiadiazol-5-yl)acetic acid, 2-amino-2-(2-oxobenzimidazol-5-yl)acetic acid, 2-amino-3-(4-hydroxybenzothiazol-6-yl)propanoic acid, 2-amino-3-(benzoxazol-2-yl)propanoic acid, 2-amino-3-(benzothiazol-2-yl)propanoic acid, 2-amino-3-(9-adeninyl)propanoic acid, 2-amino-2-(6-chloro-9-purinyl)acetic acid, 2-amino-2-(6-amino-9-purinyl)acetic acid, 2-amino-3-(6-purinyl)propanoic acid, 2-amino-3-(8-theobrominyl)propanoic acid, 2-amino-2-(1-uracilyl)acetic acid, 2-amino-2-(1-cytosinyl) acetic acid, 2-amino-3-(1-uracilyl)propanoic acid, 2-amino-3-(1-cytosinyl)propanoic acid, 2-amino-4-(1-pyrimidinyl) butanoic acid, 2-amino-4-(4-amino-1-pyrimidinyl)butanoic acid, 2-amino-4-(4-hydroxy-1-pyrimidinyl)butanoic acid, 2-amino-5-(1-pyrimidinyl)pentanoic acid, 2-amino-5-(4-amino-1-pyrimidinyl)pentanoic acid, 2-amino-5-(4-hydroxy-1-pyrimidinyl)pentanoic acid, 2-amino-3-(5-pyrimidinyl)propanoic acid, 2-amino-3-(6-uracilyl) propanoic acid, 2-amino-3-(2-pyrimidinyl)propanoic acid, 2-amino-3-(6-amino-4-chloro-2-pyrimidinyl)propanoic acid, 2-amino-3-(4-hydroxy-2-pyrimidinyl)propanoic acid, 2-amino-3-(2-amino-4-pyrimidinyl)propanoic acid, 2-amino-3-(4,5-dihydroxypyrimidin-2-yl)propanoic acid, 2-amino-3-(2-thiouracil-6-yl)propanoic acid, 2-amino-2-(5-alkyl-2-tetrahydrofuryl)acetic acid, 2-amino-2-(5-methyl-2, 5-dihydro-2-furyl)acetic acid, 2-amino-2-(5-alkyl-2-furyl) acetic acid, 2-amino-2-(2-furyl)acetic acid, 2-amino-2-(3-hydroxy-5-methyl-4-isoxazolyl)acetic acid, 2-amino-3-(4-bromo-3-hydroxy-5-isoxazolyl)propanoic acid, 2-amino-3-(4-methyl-3-hydroxy-5-isoxazolyl)propanoic acid, 2-amino-3-(3-hydroxy-5-isoxazolyl)propanoic acid, 2-amino-2-(3-chloro-D2-isoxazolin-5-yl)acetic acid, 2-amino-2-(3-oxo-5-isoxazolidinyl)acetic acid, 2-amino-3-(3,5-dioxo-1,2,4-oxadiazolin-2-yl)propanoic acid, 2-amino-3-(3-phenyl-5-isoxazolyl)propanoic acid, 2-amino-3-[3-(4-hydroxyphenyl)-1,2,4-oxadiazol-5-yl]propanoic acid, 2-amino-3-(2-thienyl)propanoic acid, 2-amino-2-(2-furyl) acetic acid, 2-amino-2-(2-thienyl)acetic acid, 2-amino-2-(2-thiazolyl)acetic acid, 2-amino-3-(2-thiazolyl)propanoic acid, 2-amino-4-(4-carboxy-2-thiazolyl)butanoic acid, 2-amino-3-(4-thiazolyl)propanoic acid, 2-amino-3-(2-selenolyl)propanoic acid, 2-amino-3-(2-amino-4-selenolyl) propanoic acid, and 2-amino-3-(beta-ribofuranosyl) propanoic acid.

"Amino acid residue" also refers to various amino acids where sidechain functional groups are modified with appropriate protecting groups known to those skilled in the art. "The Peptides", Vol 3, 3–88 (1981) discloses numerous suitable protecting groups and is incorporated herein by reference for that purpose. Examples of amino acids where sidechain functional groups are modified with appropriate protecting groups include, but are not limited to, Asp(OMe), Glu(OMe), Hyp(OMe), Asp(O$^t$Bu), Glu(O$^t$Bu), Hyp(O$^t$Bu), Thr(O$^t$Bu), Asp(OBzl), Glu(OBzl), Hyp(OBzl), and Thr (OBzl); wherein OMe is methoxy, O$^t$Bu is tert-butoxy, and OBzl is benzyloxy.

A preferred list of "amino acid residue" in the present invention includes, but is not limited to, Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O$^t$Bu), Glu(O$^t$Bu), Hyp(O$^t$Bu), Thr(O$^t$Bu), Asp(OBzl), Glu(OBzl), Hyp(OBzl), Thr(OBzl), cyclohexylglycine, cyclohexylalanine, cyclopropylglycine, t-butylglycine, phenylglycine, 3,3-diphenylalanine and

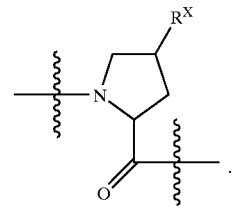

A preferred scope of substituent A is $A^2$-$A^3$, $A^2$-$A^3$-$A^4$, $A^2$-$A^3$-$A^4$-$A^5$, $A^2$-$A^3$-$A^4$-$A^5$-$A^6$.

A preferred scope of substituent $A^2$ is Pro, Leu, Asp, Abu, Val, cyclohexylalanine and

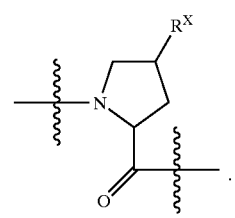

A preferred scope of substituent $A^3$ is Val, Glu, Ile, Thr, cyclohexylglycine, and cyclohexylalanine.

A preferred scope of substituent $A^4$ is Val, Ile, Leu, cyclohexylglycine, cyclopropylglycine, t-butylglycine, phenylglycine, and 3,3-diphenylalanine.

A preferred scope of substituent $A^5$ is (D or L stereochemistry) Asp, Glu, Val, Ile, t-butylglycine, and Gla.

A preferred scope of substituent $A^6$ is Asp and Glu.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

As used herein, "carbocycle", "carbocyclic ring", "carbocyclic group", or "carbocyclic ring system" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle", "heterocyclic group", "heterocyclic ring" "heterocyclic ring system" or "Het" is intended to mean a stable 5- to 7-membered monocyclic or bicyclic or 7- to 14-membered bicyclic heterocyclic ring which is saturated, partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, benzo[1,3]dioxol-yl, 2,3-dihydro-benzo[1,4]dioxin-yl, carbazolyl, 4aH-carbazolyl, b-carbolinyl, chromanyl, chromenyl, cinnolinyl, decahydroquinolinyl, 2H, 6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyrimidopyrimidin-yl, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5–10 membered heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

The term "Het-(lower alkyl)-" as used herein, means a heterocyclic ring as defined above linked through a chain or branched $C_1$–$C_6$ alkyl group.

As used herein, the term "aryl", or aromatic residue, is intended to mean an aromatic moiety containing the specified number of carbon atoms, such as phenyl and naphthyl.

"$NH_2$-blocking group" as used herein, refers to various acyl, thioacyl, alkyl, sulfonyl, phosphoryl, and phosphinyl groups comprised of 1 to 20 carbon atoms. Substitutes on these groups maybe either alkyl, aryl, alkylaryl which may contain the heteroatoms, O, S, and N as a substituent or in-chain component. A number of $NH_2$-blocking groups are recognized by those skilled in the art of organic synthesis. By definition, an $NH_2$-blocking group may be removable or may remain permanently bound to the $NH_2$. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meinhoffer, eds., The Peptides, Vol 3; 3–88 (1981), Academic Press, New York, and Greene and Wuts Protective Groups in Organic Synthesis, 315–405 (1991), J. Wiley and Sons, Inc., New York disclose numerous suitable amine protecting groups and they are incorporated herein by reference for that purpose. Amine protecting groups may include, but are not limited to the following: 2,7-di-t-butyl-[9-(10,10-dioxo-10, 10,10,10-tetrahydrothio-xanthyl)]methylo xycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-( p-toluenesulfonyl) ethyloxycarbonyl; m-chloro-p-acyloxybenzyloxycarbonyl; 5-benzyisoxazolylmethyloxycarbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, "cyclic boronic ester" is intended to mean a stable cyclic boronic moiety of general formula —B(OR)(OR) wherein the two R substituents taken together contain from 2 to 20 carbon atoms, and optionally, 1, 2, or 3 heteroatoms which can be N, S, or O. Cyclic boronic esters are well known in the art. Examples of cyclic boronic ester include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 1,2-diisopropylethanediol boronic ester, 5,6-decanediol boronic ester, 1,2-dicyclohexylethanediol boronic ester, diethanolamine boronic ester, and 1,2-diphenyl-1,2-ethanediol boronic ester.

As used herein, "cyclic boronic amide" is intended to mean a stable cyclic boronic amide moiety of general formula —B(NR)(NR) wherein the two R substituents taken together contain from 2 to 20 carbon atoms, and optionally, 1, 2, or 3 heteroatoms which can be N, S, or O. Examples of cyclic boronic amide include, but are not limited to, 1,3-diaminopropane boronic amide and ethylenediamine boronic amide.

As used herein, "cyclic boronic amide-ester" is intended to mean a stable cyclic boronic amide-ester moiety of general formula —B(OR)(NR) wherein the two R substituents taken together contain from 2 to 20 carbon atoms, and optionally, 1, 2, or 3 heteroatoms which can be N, S, or O. Examples of cyclic boronic amide include, but are not limited to, 3-amino-1-propanol boronic amide-ester and ethanolamine boronic amide-ester.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p.1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

The term "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

Synthesis

The compounds of the present invention can be prepared in a number of ways well known to one skilled in the art of organic synthesis. The compounds of the present invention can be synthesized using the methods described below, together with methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Synthesis of $A^6$-$A^5$-$A^4$-$A^3$-$A^2$ Peptide Fragments

The $A^6$-$A^5$-$A^4$-$A^3$-$A^2$ fragments of the compounds of the present invention were synthesized according to the process as illustrated in Scheme 1 (wherein PG1 is an amino protecting group and PG2 is a carboxyl protecting group):

Scheme 1

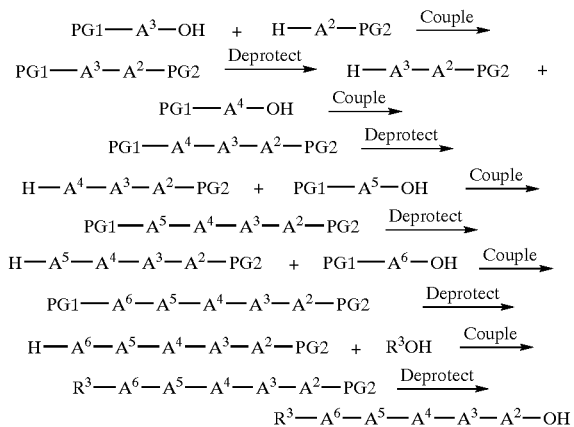

Briefly, the $A^2$, $A^3$, and optionally $A^4$, $A^5$, and $A^6$ amino acids can be linked by well known peptide coupling techniques. The $A^2$, $A^3$, $A^4$, $A^5$ and $A^6$ moieties may be linked together in any order as long as the final compound corresponds to peptides of Formula (I). For example, $A^6$ can be linked to $A^5$ to give $A^6$-$A^5$ that is linked to $A^4$-$A^3$-$A^2$; or $A^6$ linked to $A^5$-$A^4$-$A^3$ then linked to an appropriately C-terminal protected $A^2$. Consequently, Scheme 1 enables one skilled in the art to make peptides wherein A is $A^3$-$A^2$, $A^4$-$A^3$-$A^2$, $A^5$-$A^4$-$A^3$-$A^2$, or $A^6$-$A^5$-$A^4$-$A^3$-$A^2$.

Generally, peptides are elongated by deprotecting the α-amino group of the N-terminal residue and coupling to the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme 1, or by condensation of fragments (two or several amino acids), or combination of both processes, or by solid phase peptide synthesis according to the method originally described in Merrifield, J. Am. Chem. Soc., (1963), 85, 2149–2154, the disclosure of which is hereby incorporated by reference. Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (1,3-dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole (HOBt) or 1-hydroxy-7-azabenzotriazole (HOAt). These coupling reactions can be performed in either solution (liquid phase) or on solid phase. More explicitly, the coupling step involves the dehydrative coupling of a free carboxyl of one reactant with the free amino group of the other reactant in the presence of a coupling agent to form a linking amide bond. Description of such coupling agents are found in general textbooks on peptide chemistry, for example, M. Bodanszky, "Peptide Chemistry", 2nd rev ed., Springer-Verlag, Berlin, Germany, (1993). Examples of suitable coupling agents are N,N'-1,3-dicyclohexylcarbodiimide, 1-hydroxybenzotriazole in the presence of N,N'1,3-dicyclohexylcarbodiimide or N-ethyl-N'-[(3 dimethylamino)propyl]carbodiimide. A very practical and useful coupling agent is the commercially available (benzotriazol-1-yloxy)tris (dimethylamino)phosphonium hexafluorophosphate, either by itself or in the presence of 1-hydroxybenzotriazole. Another very practical and useful coupling agent is commercially available 2-(1H-benzotriazol-1-yl)-N, N, N', N'-tetramethyluronium tetrafluoroborate. Still another very practical and useful coupling agent is commercially available 2-(7-azabenzotriazol-1-yl) N,N,N', N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine,or sodium bicarbonate is added to maintain the reaction mixture at a pH of about 8. The reaction temperature usually ranges between 0° C. and 50° C. and the reaction time usually ranges between 15 min and 24 h. When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated. In addition to the foregoing, other methods of peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980–1987); Bodansky et al., "The Practice of Peptide Synthesis" Springer-Verlag, New-York (1984), the disclosures of which are hereby incorporated by reference. The functional groups of the constituent amino acids generally must be protected during the coupling reactions to avoid formation of undesired bonds. The is protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference. The α-carboxyl group of the C-terminal residue is usually protected as an ester (PG2) that can be cleaved to give the carboxylic acid. Protecting groups that can be used include: 1) alkyl esters such as methyl, ethyl, trimethylsilylethyl and t-butyl, 2) aralkyl esters such as benzyl and substituted benzyl, or 3) esters that can be cleaved by mild base treatment or mild reductive means such as trichloroethyl and phenacyl esters. The α-amino group of each amino acid to be coupled to the growing peptide chain must be protected (PG1). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT). Any of the amino acids having side chain functionalities must be protected during the preparation of the peptide using any of the above described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the a-amino group. For example, when Boc is used as the α-amino protecting group, p-toluenesulfonyl (tosyl) is suitable to protect the amino side chain of amino acids such as Lys and Arg; acetamidomethyl, benzyl (Bn), or t-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid. When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine. Once the elongation of the peptide is completed, all of the protecting groups are removed. When a liquid phase synthesis is used, the protecting groups are removed in whatever manner is dictated by the choice of protecting groups. These procedures are well known to those skilled in the art. When a solid phase synthesis is used, the peptide is cleaved from the resin simultaneously with the removal of the protecting groups. When the Boc protection method is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection method is used, the N-terminal Fmoc group is cleaved with reagents described earlier. The other protecting groups and the peptide are cleaved from the resin using solution of trifluoroacetic acid and various additives such as anisole, etc.

Synthesis of Capping Group $R^3$ and $A^6$, $A^5$, $A^4$, $A^3$ and $A^2$ Moieties Different capping groups $R^3$ are introduced to a protected peptide segment containing a free amino terminus with an appropriate acyl chloride, sulphonyl chloride, or isocyanate that is either available commercially or can be synthesized from methods known in the art. Different $A^2$ to $A^6$ amino acids are available commercially or their synthesis is well known in the art. For instance, amino acids may be synthesized in racemic form using the Strecker synthesis or amidomalonate synthesis. In addition, the Myers pseudoephedrine glycinamide alkylation method (Myers, A. G.; Gleason, J. L.; Yoon, T; Kung, D. W. *J. Am. Chem. Soc.* 1997, 119, 656–673) and the Evans electrophilic azidation (Evans, D. A.; Britton, T. C.; Ellman, J. A.; Dorow, R. L. *J. Am. Chem. Soc.* 1990, 112, 4011) may be used to prepare unnatural amino acids in enantiomerically pure form. Introduction and manipulation of appropriate protecting groups is well known in the art. Synthesis of substituted prolines are well known in the art. Extensive disclosure of substituted prolines can be found in WO 00/09543 and WO 00/09558 (Llinas-Brunet et al.).

Synthesis of P1 (—NR$^2$—CHR$^1$—W) Moiety and Coupling to Peptidyl Fragments

The P1 residue in the claimed compounds may contain a boronic ester or acid (W=BY$^1$Y$^2$, an α-ketoamide (W=COCONHQ), or other electrophilic carbonyl derivative known

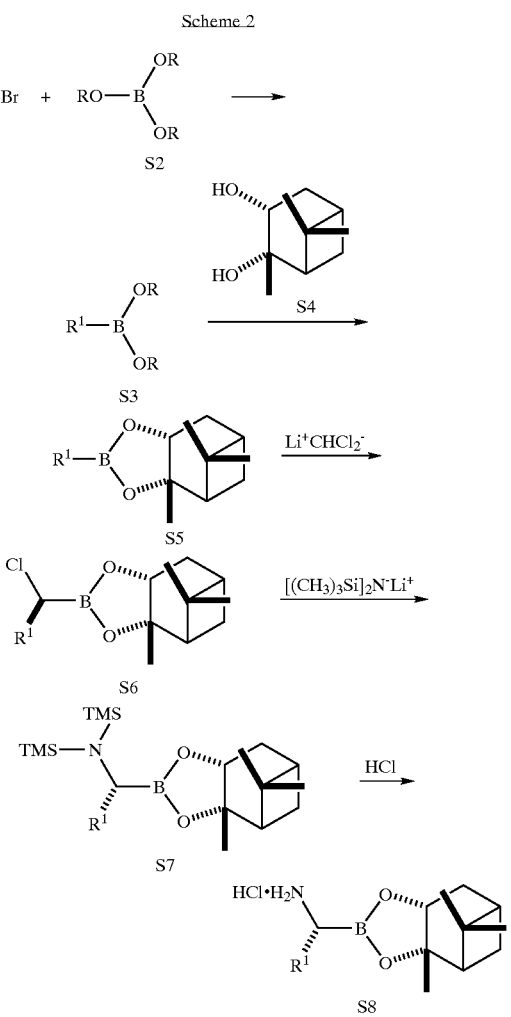

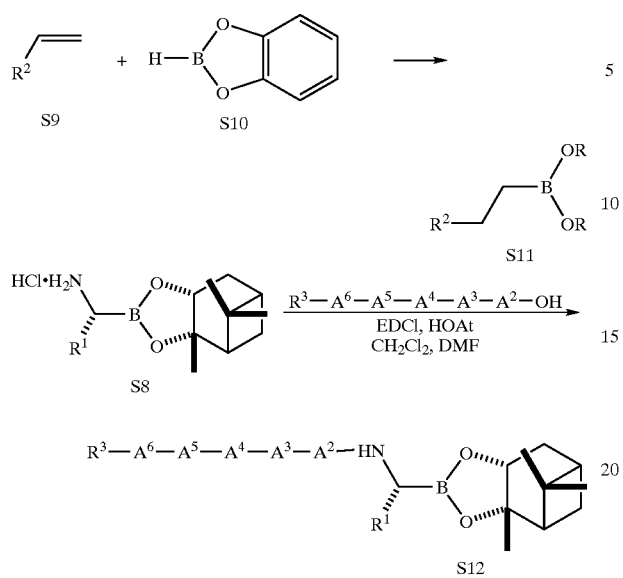

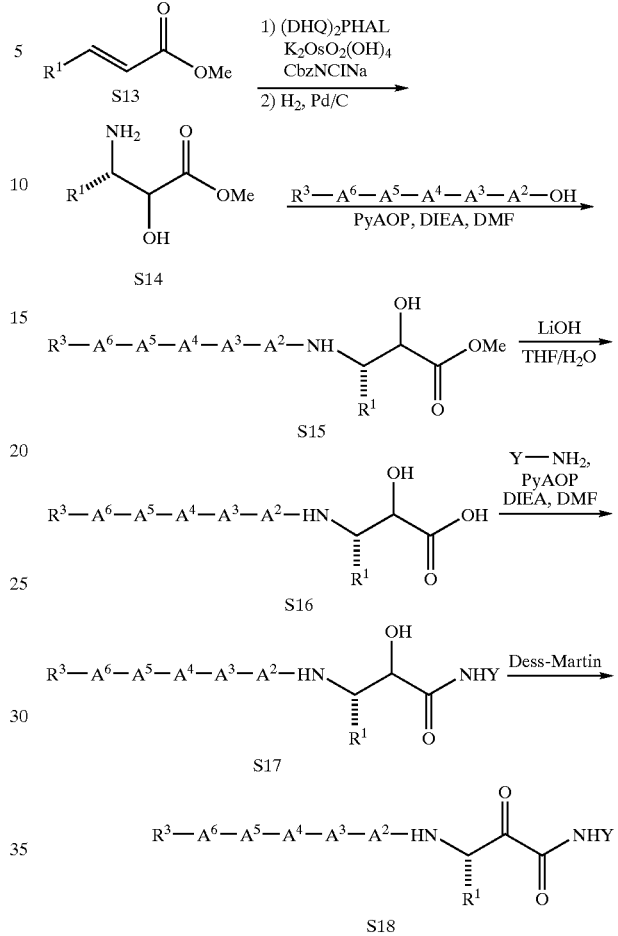

to one skilled in the art (Edwards, P. D.; Bernstein, P. R. *Medicinal Res. Reviews* 1994, 14, 127–194, and references cited therein). Scheme 2 shows the synthetic route to α-amino boronic esters S8 and their peptidyl derivatives. Grignard reagent S1 is reacted with a trialkyl borate ester S2, providing boronate S3. Transesterification with (+)-pinanediol S4 affords the cyclic ester S5. This ester ultimately yields enantiomerically pure S8 with L-configuration. Substitution of pinacol for pinanediol yields racemic product. Homologation of S5 with the anion of dichloromethane gives the α-chloro boronic ester S6 (Matteson, D. S.; Majumdar, D. *Organometallics* 1983, 2, 1529–1535). Displacement of chloride by lithium bis(trimethylsilyl)amide gives silyl amine S7, which is converted to the amine hydrochloride S8 with anhydrous HCl (Matteson, D. S., Sadhu, K. M. *Organometallics* 1984, 3, 1284–1288). An alternative route to boronate S3 involves hydroboration of an olefin S9 with catecholborane S10 (Brown, H. C.; Gupta, S. K. *J. Am. Chem. Soc.* 1975, 97, 5249–5255), providing boronate S11, which may be converted to S8 by the same synthetic sequence as described above for S3. Compound S8 is coupled to a peptide fragment using, for instance, EDCI/HOAt to generate peptide boronic ester S12. In some cases, a final step may be required to remove side chain protecting groups on the peptide. (For a general reference to synthesis of peptide boronic esters, see: Kettner, C.; Forsyth, T. *Houben-Weyl Methods of Organic Chemistry* 2000, in press.)

α-Ketoamides and other electrophilic ketone derivatives are generally introduced in the hydroxy form and oxidized to the active ketone form in the final synthetic step. Scheme 3 illustrates the synthesis of peptidyl α-ketoamides. Other electrophilic ketone derivatives may be prepared analogously (Edwards, P. D.; Bernstein, P. R. *Medicinal Res. Reviews* 1994, 14, 127–194, and references cited therein). $R^1$ substituted acrylate ester S13 is aminohydroxylated and subsequently deprotected to give amino alcohol S14. The amino alcohol is coupled to a peptide fragment to give S15. Saponification with LiOH affords acid S16, which is coupled to an amine Y—$NH_2$, to give hydroxy amide S17. Oxidation with Dess-Martin periodinane affords the peptidyl α-keto amide S18.

EXAMPLES

Abbreviations used in the examples are defined as follows: "1×" for once, "2×" for twice, "3×" for thrice, "° C." for degrees Celsius, "rt" for room temperature, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "MS" for mass spectrometry, "NMR" for nuclear magnetic resonance spectroscopy, "$^1$H" for proton, "HPLC" for high pressure liquid chromatography, "tlc" for thin layer chromatography, "v/v" for volume to volume ratio, "atm" for atmosphere, "α", "β", "R" and "S" are stereochemical designations familiar to one skilled in the art.

Example 1

Boc-Asp(O-tBu)-Glu(O-tBu)-Val-Val-Pro-OH (1a) N-methylmorpholine (5.5 mL, 50 mmol) and 1,3-dicyclohexylcarbodiimide (10 g, 48 mmol) were added portionwise to a solution of L-proline benzyl ester hydrochloride (12.5 g, 52 mmol), Boc-L-valine (10.9 g, 50 mmol) and 1-hydroxybenzotriazole (7.01 g, 52 mmol) in chloroform (100 mL) at 0° C. The reaction mixture was allowed to slowly warm to room temperature overnight. The crude mixture was filtered, extracted with 5% sodium bicarbonate (2×), 0.2 M hydrochloric acid (2×) and brine, :dried (MgSO$_4$) and concentrated under reduced pressure. The residual oil was purified by chromatography on silica gel (10 to 30% ethyl acetate in hexane) to afford 1a as a white solid (16.4 g, 84%). MS found: (M+H)$^+$=405.

(1b) The Boc protected dipeptide 1a (10.5 g, 26 mmol) was added to a solution of hydrogen chloride in 1,4-dioxane (50 mL, 4 M solution) at 0° C. After 30 min, additional hydrogen chloride in 1,4-dioxane (20 mL) was added and the reaction mixture was stirred for 1 h at rt. The resulting solution was concentrated and the residue was washed with ether to afford 1b as a white solid (9.16 g, 100%). MS found: (M+H)$^+$=305.

(1c) 1,3-Dicyclohexylcarbodiimide (6.22 g, 30 mmol) was added to a solution of dipeptide 1b (9.16 g, 26 mmol), Boc-L-valine (6.54 g, 30 mmol), 1-hydroxybenzotriazole (8.14 g, 60 mmol) and N-methylmorpholine (3.3 mL, 30 mmol) in dichloromethane (150 mL). After 5 h, additional N-methylmorpholine (5 mL, 45 mmol) was added and the reaction mixture was stirred overnight at rt. The mixture was filtered, concentrated under reduced pressure, suspended in ethyl acetate, and filtered again. The filtrate was extracted with 5% sodium bicarbonate (2×), 0.2 M hydrochloric acid and brine, dried (MgSO$_4$) and concentrated under reduced pressure to afford 1c as a white foam (11.1 g, 85%). MS found: (M+H)$^+$=504.

(1d) Boc protected tripeptide 1c (6.22 g, 12.4 mmol) was added to a solution of hydrogen chloride in 1,4-dioxane (75 mL, 4 M solution) at 0° C. After 2 h, the reaction mixture was concentrated under reduced pressure to give hydrochloride salt 1d as a white solid (5.39 g, 100%). MS found: (M+H)$^+$=404.

(1e) 1,3-Dicyclohexylcarbodiimide (2.58 g, 12.5 mmol) was added to a suspension of tripeptide 1d (5.26 g, 12.0 mmol), Cbz-L-glutamic acid-γ-t-butyl ester (4.07 g, 11.7 mmol), 1-hydroxybenzotriazole (3.16 g, 23.4 mmol) and N-methylmorpholine (3 mL, 27 mmol) in dichloromethane (100 mL) and N,N-dimethylformamide (10 mL). The reaction mixture was stirred overnight at rt. The mixture was filtered, concentrated under reduced pressure, suspended in ethyl acetate, and filtered again. The filtrate was extracted with 5% sodium bicarbonate (2×), 0.2 M hydrochloric acid and brine, dried (MgSO$_4$) and concentrated under reduced pressure. The residual foam was purified by chromatography on silica gel (methanol/chloroform 1:10) to provide tetrapeptide 1e as a white foam (8.46 g, 98%). MS found: (M+H)$^+$=723.

(1f) Tetrapeptide 1e (3.00 g, 4.1 mmol) was dissolved in methanol (200 mL) and acetic acid (2 mL). Palladium hydroxide (211 mg, 20 wt. % palladium on carbon) was added and the mixture was treated with hydrogen gas (45 psi) for 4 h. The reaction mixture was concentrated under reduced pressure to afford 1f as a pink solid (2.26 g, 100%). MS found: (M+H)$^+$=499.

(1g) 1,3-Dicyclohexylcarbodiimide (758 mg, 3.7 mmol) was added to a solution of Boc-L-aspartic acid-β-t-butyl ester (1.00 g, 3.5 mmol) and N-hydroxysuccinimide (413 mg, 3.6 mmol) in 1,2-dimethoxyethane (5 mL). The reaction mixture was stirred overnight at rt. The resulting suspension was filtered and concentrated under reduced pressure to give 1g as a white solid (1.48 g, 100%). MS found: (M+H)$^+$=387.

(1h) A solution of N-hydroxysuccinimide ester 1g (1.48 g, 3.5 mmol) was added dropwise to a suspension of tetrapeptide 1f (2.10 g, 4.2 mmol), sodium bicarbonate (526 mg, 6.3 mmol) and triethylamine (0.880 mL, 6.3 mmol) in a mixture of water (10 mL) and 1,4-dioxane (10 mL). The reaction mixture was stirred overnight at rt. The dioxane was removed under reduced pressure and the solution was acidifed to pH 1 with hydrochloric acid. The solution was extracted with ethyl acetate (2×) and the combined organic phases washed with hydrochloric acid (0.2 M, 2×) and brine. The solution was dried over (MgSO$_4$) and concentrated under reduced pressure. The residue was purified by high performace liquid chromatography (Rainin Dynamax C18 column, gradient from 50 to 80% acetonitrile in water containing 0.1% trifluoroacetic acid over 30 min, 250 mg injections) to afford pentapeptide 1h as a white solid (2.2 g, 82%). MS found: (M−H)$^−$=769.

Example 2

H-Asp-Glu-Val-Val-Pro-(R)-amino(phenyl) methylboronic acid (+)-pinanediol ester (2a) (1S, 2S, 3R, 5S)-(+)-Pinanediol (referred to hereafter as (+)-Pinanediol) (1.70 g, 10 mmol) was added to a solution of phenylboric acid (1.22 g, 10 mmol) in diethyl ether (20 mL). Magnesium sulfate was subsequently added. After 14 h, the solution was concentrated under reduced pressure to afford 1a as a colorless solid (2.16 g, 84%) MS found: (M+H)$^+$=257.

(2b) General procedure A for the homologation of boronate esters (Reference: Matteson, D. S.; Majumdar, D. *Organometallics* 1983, 2, 1529–1535). n-Butyllithium (5.2 mL, 8.3 mmol, 1.6 M solution in hexane) was added dropwise to a solution of dry dichloromethane (0.640 mL, 10.0 mmol) in tetrahydrofuran (4 mL) at −100° C. After 30 min, a solution of boronate ester 2a (2.15 g, 8.4 mmol) in tetrahydrofuran (4 mL) was added slowly dropwise, taking care to drip the solution down the side of the flask to precool it. The reaction mixture was allowed to slowly warm to rt and then concentrated under reduced pressure. The residue was suspended in a mixture of hexane and ethyl acetate and filtered. The filtrate was concentrated under reduced pressure and the residue was purified by chromatography on silica gel (19:1 hexane/ethyl acetate) to afford 2b as a colorless solid (1.62 g, 63%). $^1$H NMR (CDCl$_3$, 300 MHz) δ 7.48–7.24 (m, 5H), 4.54 (s, 1H), 4.38 (dd, J=9,2 Hz), 2.38–2.29 (m, 1H), 2.26–2.18 (m, 1H), 2.11 (t, J=5 Hz), 1.93–1.84 (m, 2H), 1.41 (S, 3H), 1.29 (s, 3H), 1.14 (d, J=11 Hz), 0.83 (S, 3H).

(2c) General procedure B for conversion of α-chloroboronic ester to α-aminoboronic ester. Lithium bis(trimethylsilyl) amide (2.6 mL, 2.6 mmol, 1.0 M solution in tetrahydrofuran) was added dropwise to a solution of 2b (0.791 g, 2.6 mmol) in tetrahydrofuran at −78° C. The reaction mixture was allowed to slowly warm to rt and stir overnight. The solution was concentrated under reduced pressure. The residue was suspended in hexane, filtered through Celite and concentrated under reduced pressure. The residue was dissolved in hexane (10 mL) and treated with hydrogen chloride (2.0 mL, 8.0 mmol, 4 M solution in 1,4-dioxane) at −78° C. The reaction mixture was allowed to warm to rt and then was concentrated under reduced pressure. The residue was dissolved in chloroform (2 mL) and precipitated by the addition of hexane to afford 2c (0.42 g, 50%) as a slightly yellow solid) MS found: (M+H)$^+$=286.

(2d) General procedure C for coupling α-aminoboronic ester to peptide: N,N-Diisopropylethylamine (DIEA) (0.032 mL, 0.19 mmol) was added dropwise to a solution of pentapeptide 1h (28 mg, 0.036 mmol) and PyAOP (Carpino, L. A.; El-Faham, A.; Minor, C. A.; Albericio, F. *J. Chem. Soc., Chem. Commun.* 1994, 201–203) (21 mg, 0.040) in N,N-dimethylformamide. After 5 min, aminoboronic ester 2c (19 mg, 0.059 mmol) was added. The reaction mixture was stirred at rt for 3 h and then was concentrated under reduced pressure. The residue was purified by high performance liquid chromatography (HPLC) (Rainin Dynamax C18 column, gradient from 40 to 100% acetonitrile in water containing 0.1% trifluoroacetic acid over 30 min) to afford 2d (22.6 mg, 61%) as a white foam. MS found: (M−H)⁻=1036.

(2e) Peptide boronic ester 2d (12.4 mg, 0.012 mmol) was dissolved in a mixture of trifluoroacetic acid (TFA) (1 mL), triisopropylsilane (0.050 mL) and dichloromethane (0.050 mL). The reaction mixture was stirred at rt for 4 h and then was concentrated under reduced pressure. The residue was purified by high performance liquid chromatography (Rainin Dynamax C18 column, gradient from 20 to 70% acetonitrile in water containing 0.1% trifluoroacetic acid over 30 min) to afford 2e. MS found: (M+H)⁺=825.5.

Example 3

H-Asp-Glu-Val-Val-Pro-(1R)-1-amino-3-phenylpropylboronic acid (+)-pinanediol ester (3a) A solution of triisopropyl borate(5.75 mL, 25 mmol) in diethyl ether (15 mL) was added slowly dropwise to diethyl ether (10 mL) at −78° C. Phenethyl magnesium chloride (25 mL, 25 mmol, 1 M in tetrahydrofuran) was added slowly dropwise at the same time. The reaction mixture was allowed to warm slowly to rt and stirred overnight. The resulting suspension was cooled in an ice bath and neutralized by addition of sulfuric acid (2.65 mL) in water (4.5 mL). After stirring 2 h, the reaction mixture was diluted with water (15 mL) and extracted with diethyl ether (2×). The organic layers were dried (Na₂SO₄) and (+)-pinanediol (4.25 g, 25 mmol) was added. The solution was stirred for several days and was then filtered and concentrated under reduced pressure. The residue was by chromatography on silica gel (hexane/ethyl acetate 9:1) to provide phenethyl boronate 3a as a colorless oil (3.6 g, 51%).

(3b) Following a procedure analogous to (2b), Phenethyl-boronate 3a (3.6 g, 12.7 mmol) was treated with n-butyllithium and dichloromethane in tetrahydrofuran to provide the desired α-chloroboronic ester 3b as an orange oil which was a 2:1 mixture of starting material and product(3.5 g, 55%) after chromatography on silica gel.

(3c) Following a procedure analogous to (2c), α-chloroboronic ester 3b (3.5 g, 2:1 mixture of 3b and 3a, 6.9 mmol) was converted to the aminoboronic ester hydrochloride 3c by treatment with lithium bis(trimethylsilyl)amide followed by hydrogen chloride. The desired product 3c was obtained as a white solid (1.44 g, 59%). MS found: (M+H)⁺=314.

(3d) Following a procedure analogous to (2d), α-aminoboronic ester 3c (20 mg, 0.057 mmol) was coupled to pentapeptide 1h (25 mg, 0.032 mmol) with PyAOP and DIEA. The desired hexapeptide 3d (8 mg, 23%) was obtained after purification by HPLC. MS found: (M−H)⁻=1064.

(3e) Following a procedure analogous to (2e), the hexapeptide 3d (5 mg, 0.005 mmol) was deprotected with TFA and triisopropylsilane to afford the desired hexapeptide 3e (4 mg, 100%) as a white solid after purification by HPLC. HRMS found: (M+H)⁺=853.4856.

Example 4

H-Asp-Glu-Val-Val-Pro-(1R)-1-amino-4-phenylbutylboronic acid (+)-pinanediol ester (4a) Magnesium (540 mg, 22.2 mmol) was suspended in tetrahydrofuran (20 mL) and treated with ethylene bromide (5 drops) to initiate Grignard reaction. After a cloudy, grey precipitate formed, 1-bromo-3-phenylpropane (3.0 mL, 20 mmol) in tetrahydrofuran (20 mL) was added slowly dropwise. The solution was refluxed 30 min to give a clear, brown solution of grignard reagent 4a. This material was used without further characterization.

(4b) Using a procedure analogous to (3a), Grignard reagent 4a (20 mmol) was reacted with triisopropyl borate and (+)-pinanediol. Silica gel chromatography (9:1 hexane/ethyl acetate) afforded the desired boronic ester 4b as a pale yellow oil (1.28 g, 21%).

(4c) Using a procedure analogous to (2b), boronic ester 4b (1.28 g, 4.29 mmol) was treated with n-butyllithium and dichloromethane in tetrahydrofuran to provide the desired α-chloroboronic ester 4c as a clear oil (0.31 g, 21%) after chromatography on silica gel.

(4d) Following a procedure analogous to (2c), α-chloroboronic ester 4c (0.31 g, 0.90 mmol) was converted to the aminoboronic ester hydrochloride 4d by treatment with lithium bis(trimethylsilyl)amide followed by hydrogen chloride. The desired product 4d was obtained as a white solid. MS found: (M+H)⁺=328.2.

(4e) Following a procedure analogous to (2d), α-aminoboronic ester (4d) (28 mg, 0.077 mmol) was coupled to pentapeptide 1h (30 mg, 0.038 mmol) with PyAOP and DIEA and purified by HPLC to afford the desired hexapeptide 4e.

(4f) Following a procedure analogous to (2e), the hexapeptide 4e (5 mg, 0.005 mmol) was deprotected with TFA and triisopropylsilane and purified by HPLC to afford the desired hexapeptide 4f (1 mg) as a white solid. HRMS found: (M+H)⁺=867.5055.

Example 5

H-Asp-Glu-Val-Val-Pro-(1R)-1-amino-5-phenylpentylboronic acid (+)-pinanediol ester (5a) Using a procedure analagous to (4a), 1-chloro-4-phenylbutane was reacted with magnesium to prepare Grignard reagent 5a. This material was used without further characterization.

(5b) Using a procedure analogous to (3a), Grignard reagent 5a (20 mmol) was reacted with triisopropyl borate and (+)-pinanediol. Silica gel chromatography (19:1 hexane/ethyl acetate) afforded the desired boronic ester 5b as a colorless oil (3.15 g, 50%).

(5c) Using a procedure analogous to (2b), boronic ester 5b (3.15 g, 10 mmol) was treated with n-butyllithium and dichloromethane in tetrahydrofuran to provide a 2:1 mixture of the desired α-chloroboronic ester 5c and starting material 5b as a clear oil (3.2 g, 59%).

(5d) Following a procedure analogous to (2c), α-chloroboronic ester 5c (3.2 g, 5.90 mmol) was converted to the aminoboronic ester hydrochloride 5d by treatment with lithium bis(trimethylsilyl)amide followed by hydrogen chloride. The desired product (5d) was obtained as a white solid. MS found: (M+H)⁺=342.3.

(5e) Following a procedure analogous to (2d), α-aminoboronic ester (5d) (40 mg, 0.11 mmol) was coupled to pentapeptide 1h (32 mg, 0.040 mmol) with PyAOP and DIEA and purified by HPLC to afford the desired hexapeptide 5e. HRMS found: (M+H)⁺=1093.695.

(5f) Following a procedure analogous to (2e), the hexapeptide 5e was deprotected with TFA and triisopropylsilane and purified by HPLC to afford the desired hexapeptide 5f. HRMS found: (M+H)⁺=881.5224.

Example 7

H-Asp-Glu-Val-Val-Pro-(1R)-1-amino-3-(2-naphthyl)propylboronic acid (+)-pinanediol ester (7a) Using a procedure analagous to (4a), 1-(2-bromoethyl)naphthalene (4.70 g, 20 mmol) was reacted with magnesium to prepare Grignard reagent 7a. This material was used without further characterization.

(7b) Using a procedure analogous to (3a), Grignard reagent 7a (20 mmol) was reacted with triisopropyl borate and (+)-pinanediol. Silica gel chromatography (99:1 hexane/ethyl acetate) afforded the desired boronic ester 7b as a colorless oil (1.34 g, 20%).

(7c) Using a procedure analogous to (2b), boronic ester 7b (1.34 g, 4.01 mmol) was treated with n-butyllithium and dichloromethane in tetrahydrofuran to provide a 4:1 mixture of the desired α-chloroboronic ester 7c and starting material 7b as a clear oil (0.18 g, 12%).

(7d) Following a procedure analogous to (2c), α-chloroboronic ester 7c (0.18 g, 0.47 mmol) was converted to the aminoboronic ester hydrochloride 7d by treatment with lithium bis(trimethylsilyl)amide followed by hydrogen chloride. The desired product 7d was obtained as a pink solid (0.120 g, 64%). MS found: $(M+H)^+=364$.

(7e) Following a procedure analogous to (2d), α-aminoboronic ester (7d) (40 mg, 0.11 mmol) was coupled to pentapeptide 1 h (29 mg, 0.038 mmol) with PyAOP and DIEA and purified by HPLC to afford the desired hexapeptide 7e. MS found: $(M+H)^+=1116$ (7f) Following a procedure analogous to (2e), the hexapeptide 7e was deprotected with TFA and triisopropylsilane and purified by HPLC to afford the desired hexapeptide 7f. HRMS found: $(M+H)^+=903.5050$.

Example 8

H-Asp-Glu-Val-Val-Pro-(1R)-1-amino-3-(2-methyl)phenylpropylboronic acid (+)-pinanediol ester (8a) Catecholborane (3.59 mL, 34 mmol) was added dropwise to 2-methylstyrene (3.87 mL, 30 mmol). The reaction mixture was heated to 70° C. and allowed to stir overnight. A solution of (+)-pinanediol (5 g, 29 mmol) in diethyl ether (100 mL) was added dropwise to the catecholborane reaction mixture. The solution was allowed to stir at rt for several days, and then was concentrated under reduced pressure. The residue was purified by chromatography on silica gel (10:1 hexane/ethyl acetate) to provide the desired boronic ester 8a as a colorless oil (6.75 g, 75%).

(8b) n-Butyllithium (6.9 mL, 11 mmol, 1.6 M in hexane) was added slowly dropwise to a solution of dichloromethane (0.96 mL, 15 mmol) in tetrahydrofuran (20 mL) at –100° C. After 30 min, a solution of boronic ester 8a (2.98 g, 10 mmol) in tetrahydrofuran (5 mL) was added slowly dropwise. After 1 hr, a solution of $ZnCl_2$ (0.69 g, 5 mmol, dried at 150° C. for several hr under vacuum) in tetrahydrofuran (5 mL) was added and the reaction mixture was allowed to slowly warm to rt and stir overnight. The reaction mixture was concentrated under reduced pressure and the residue was dissolved in diethyl ether and washed with water (2×). The organic layer was dried ($MgSO_4$) and concentrated under reduced pressure. The residue was purified by HPLC (Rainin Dynamax 60 Å silica column) in 10:7 hexane/dichloromethane to afford the desired α-chloroboronic ester 8b as a colorless oil (0.48 g, 14%).

(8c) Following a procedure analogous to (2c), α-chloroboronic ester 8b (0.48 g, 1.4 mmol) was converted to the aminoboronic ester hydrochloride 8c by treatment with lithium bis(trimethylsilyl)amide followed by hydrogen chloride. The desired product (8c) was obtained as a white solid (0.243 g, 48%). MS found: $(M+H)^+=328$.

(8d) Following a procedure analogous to (2d), α-aminoboronic ester 8c (30 mg, 0.082 mmol) was coupled to pentapeptide 1h (34 mg, 0.044 mmol) with PyAOP and DIEA. The crude protected pentapeptide was deprotected following a procedure analogous to (2e) and purified by HPLC to afford the desired hexapeptide 8d. HRMS found: $(M+H)^+=867.5012$.

Example 9

H-Asp-Glu-Val-Val-Pro-(1R)-1-amino-3-(3-methyl)phenylpropylboronic acid (+)-pinanediol ester (9a) Following a procedure analogous to (8a), 3-methylstyrene (3.54 g, 30 mmol) was treated with catecholborane, followed by (+)-pinanediol to provide the desired boronic ester 9a as a yellow oil (2.93 g, 33%).

(9b) Following a procedure analogous to (8b), boronic ester 9a (2.93 g, 9.8 mmol) was treated with n-butyllithium, dichloromethane, and $ZnCl_2$. After HPLC purification (10:9 hexane/dichloromethane), the desired α-chloroboronic ester 9b was obtained as a colorless oil (0.38 g, 11%).

(9c) Following a procedure analogous to (2c), α-chloroboronic ester 9b (0.38 g, 4.5 mmol) was converted to the aminoboronic ester hydrochloride 9c by treatment with lithium bis(trimethylsilyl)amide followed by hydrogen chloride. The desired product 9c was obtained as a white solid. MS found: $(M+H)^+=328$.

(9d) Following a procedure analogous to (8d), α-aminoboronic ester 9c (34 mg, 0.093 mmol) was coupled to pentapeptide 1h (33 mg, 0.043 mmol) with PyAOP and DIEA. The crude hexapeptide was deprotected with TFA and purified by HPLC to afford the desired hexapeptide 9d. HRMS found: $(M+H)^+=867.5041$.

Example 10

H-Asp-Glu-Val-Val-Pro-(1R)-1-amino-3-(4-methyl)phenylpropylboronic acid (+)-pinanediol ester (10a) Following a procedure analogous to (8a), 4-methylstyrene (3.95 g, 30 mmol) was treated with catecholborane, followed by (+)-pinanediol to provide the desired boronic ester 10a as a white solid (1.55 g, 17%).

(10b) Following a procedure analogous to (8b), boronic ester 10a (0.420 g, 1.4 mmol) was treated with n-butyllithium butyllithium, dichloromethane, and $ZnCl_2$. After HPLC purification (10:8 hexane/dichloromethane), the desired α-chloroboronic ester 10b was obtained as a colorless oil (0.23 g, 47%).

(10c) Following a procedure analogous to (2c), α-chloroboronic ester 10b (0.23 g, 0.66 mmol) was converted to the aminoboronic ester hydrochloride 10c by treatment with lithium bis(trimethylsilyl)amide followed by hydrogen chloride. The desired product 10c was obtained as a sticky solid (143 mg, 59%). MS found: $(M+H)^+=328$.

(10d) Following a procedure analogous to (8d), α-aminoboronic ester 10c (37 mg, 0.10 mmol) was coupled to pentapeptide 1h (36 mg, 0.046 mmol) with PyAOP and DIEA. The crude hexapeptide was deprotected with TFA and purified by HPLC to afford the desired hexapeptide 10d. HRMS found: $(M+H)^+=867.5055$.

Example 11

H-Asp-Glu-Val-Val-Pro-(1R)-1-amino-3-(1,1'-biphenyl)-4-ylpropylboronic acid (+)-pinanediol ester (11a) Following a procedure analogous to (8a), 4-vinyl biphenyl (5.4 g, 30 mmol) was treated with catecholborane, followed by (+)-pinanediol to provide the desired boronic ester 11a as a pale yellow solid (7.53 g, 71%).

(11b) Following a procedure analogous to (8b), boronic ester 11a (2.28 g, 6.3 mmol) was treated with n-butyllithium, dichloromethane, and ZnCl$_2$. After HPLC purification (11:4 hexane/dichloromethane), the desired α-chloroboronic ester 11b was obtained as a colorless oil (0.85 g, 33%).
(11c) Following a procedure analogous to (2c), α-chloroboronic ester 11b (0.85 g, 2.1 mmol) was converted to the aminoboronic ester hydrochloride 11c by treatment with lithium bis(trimethylsilyl)amide followed by hydrogen chloride. The desired product 11c was obtained as a brown solid (0.54 g, 60%). MS found: (M+H)$^+$=390.
(11d) Following a procedure analogous to (8d), α-aminoboronic ester 11c (40 mg, 0.094 mmol) was coupled to pentapeptide 1h (33 mg, 0.043 mmol) with PYAOP and DIEA. The crude hexapeptide was deprotected with TFA and purified by HPLC to afford the desired hexapeptide 11d. HRMS found: (M+H)$^+$=929.5210.

Example 12

H-Asp-Glu-Val-Val-Pro-(1R)-1-amino-3-(2,5-dimethyl)phenylpropylboronic acid (+)-pinanediol ester (12a) Following a procedure analogous to (8a), 2,5-dimethylstyrene (3.97 g, 30 mmol) was treated with catecholborane, followed by (+)-pinanediol to provide the desired boronic ester 12a as a colorless oil (7.04 g, 75%).
(12b) Following a procedure analogous to (8b), boronic ester 12a (7.04 g, 22.5 mmol) was treated with n-butyllithium, dichloromethane, and ZnCl$_2$. After HPLC purification (11:6 hexane/dichloromethane), the desired α-chloroboronic ester 12b was obtained as a colorless oil (1.94 g, 24%).
(12c) Following a procedure analogous to (2c), α-chloroboronic ester 12b (1.94 g, 5.4 mmol) was converted to the aminoboronic ester hydrochloride 12c by treatment with lithium bis(trimethylsilyl)amide followed by hydrogen chloride. The desired product 12c was obtained as a white solid. MS found: (M+H)$^+$=342.
(12d) Following a procedure analogous to (8d), α-aminoboronic ester 12c (27 mg, 0.079 mmol) was coupled to pentapeptide 1h (33 mg, 0.043 mmol) with PYAOP and DIEA. The crude hexapeptide was deprotected with TFA and purified by HPLC to afford the desired hexapeptide 11d (3 mg, 8%). HRMS found: (M+H)$^+$=881.5185.

Example 13

H-Asp-Glu-Val-Val-Pro-(1R)-1-amino-3-(2,4-dimethyl)phenylpropylboronic acid (+)-pinanediol ester (13a) Following a procedure analogous to (8a), 2,4-dimethylstyrene (3.97 g, 30 mmol) was treated with catecholborane, followed by (+)-pinanediol to provide the desired boronic ester 13a as a colorless oil (7.77 g, 82%).
(13b) n-Butyllithium (7.6 mL, 12.2 mmol, 1.6 M in hexane) was added dropwise over 50 min to a solution of dichloromethane (1.1 mL, 17 mmol) in tetrahydrofuran (40 mL) at −100° C. After 20 min, a solution of boronic ester 13a (3.47 g, 11 mmol) in tetrahydrofuran (5 mL) was added dropwise over 20 min. The reaction mixture was allowed to slowly warm to rt and stir overnight. The reaction mixture was concentrated under reduced pressure and the residue was dissolved in diethyl ether and washed with 0.1 N sulfuric acid (2×). The organic layer was dried (MgSO$_4$) and concentrated under reduced pressure. The residue was purified by HPLC (Rainin Dynamax 60 Å silica column) in 11:5 hexane/dichloromethane to afford the desired α-chloroboronic ester 13b as a colorless oil (1.76 g, 44%).
(13c) Following a procedure analogous to (2c), α-chloroboronic ester 13b (1.76 g, 4.9 mmol) was converted to the aminoboronic ester hydrochloride 13c by treatment with lithium bis(trimethylsilyl)amide followed by hydrogen chloride. The desired product 13c was obtained as a tan solid. MS found: (M+H)$^+$=342.3.
(13d) Following a procedure analogous to (8d), α-aminoboronic ester 13c (34 mg, 0.099 mmol) was coupled to pentapeptide 1h (30 mg, 0.039 mmol) with PyAOP and DIEA. The crude hexapeptide was deprotected with TFA and purified by HPLC to afford the desired hexapeptide 13d (6 mg, 17%). HRMS found: (M+H)$^+$=881.5192.

Example 14

H-Asp-Glu-Val-Val-Pro-(1R)-1-amino-3-(4-trifluoromethyl)phenylpropylboronic acid (+)-pinanediol ester (14a) Following a procedure analogous to (8a), 4-trifluoromethylstyrene (3.0 g, 17 mmol) was treated with catecholborane, followed by (+)-pinanediol to provide the desired boronic ester 14a as a colorless oil (3.1 g, 51%).
(14b) Following a procedure analogous to (13b), boronic ester 14a (3.12 g, 22.5 mmol) was treated with n-butyllithium and dichloromethane. After HPLC purification, the desired α-chloroboronic ester 14b was obtained as a colorless oil (1.39 g, 39%).
(14c) Following a procedure analogous to (2c), α-chloroboronic ester 14b (1.39 g, 3.5 mmol) was converted to the aminoboronic ester hydrochloride 14c by treatment with lithium bis(trimethylsilyl)amide followed by hydrogen chloride. The desired product 14c was obtained as a yellow solid (0.65 g, 44%). MS found: (M+H)$^+$=382.
(14d) Following a procedure analogous to (8d), α-aminoboronic ester 14c (28 mg, 0.054 mmol) was coupled to pentapeptide 1h (32 mg, 0.042 mmol) with PyAOP and DIEA. The crude hexapeptide was deprotected with TFA and purified by HPLC to afford the desired hexapeptide 14d (6 mg, 16%). HRMS found: (M+H)$^+$=921.4785.

Example 15

H-Asp-Glu-Val-Val-Pro-(1R)-1-amino-3-(3-trifluoromethyl)phenylpropylboronic acid (+)-pinanediol ester (15a) Following a procedure analogous to (8a), 3-trifluoromethylstyrene (2.0 g, 11.6 mmol) was treated with catecholborane, followed by (+)-pinanediol to provide the desired boronic ester 15a as a colorless oil (2.24 g, 55%) after chromatography on silica gel (9:1 hexane ethyl acetate).
(15b) Following a procedure analogous to (13b), boronic ester 15a (2.24 g, 6.4 mmol) was treated with n-butyllithium and dichloromethane. After HPLC purification, the desired α-chloroboronic ester 15b was obtained as a colorless oil (0.70 g, 27%).
(15c) Following a procedure analogous to (2c), α-chloroboronic ester 15b (0.70 g, 1.75 mmol) was converted to the aminoboronic ester hydrochloride 15c by treatment with lithium bis(trimethylsilyl)amide followed by hydrogen chloride. The desired product 15c was obtained as a tan solid (0.41 g, 56%). MS found: (M+H)$^+$=382.
(15d) Following a procedure analogous to (8d), α-aminoboronic ester 15c (39 mg, 0.093 mmol) was coupled to pentapeptide 1h (40 mg, 0.052 mmol) with PyAOP and DIEA. The crude hexapeptide was deprotected with TFA and purified by HPLC to afford the desired hexapeptide 15d. HRMS found: (M+H)$^+$=921.4765.

Example 16

H-Asp-Glu-Val-Val-Pro-(1R)-1-amino-3-(4-fluoro)phenylpropylboronic acid (+)-pinanediol ester (16a) Following a procedure analogous to (8a), 4-fluorostyrene (2.44 g, 20.0 mmol) was treated with catecholborane, followed by (+)-pinanediol to provide the desired boronic ester 16a as a colorless oil (3.86 g, 64%).
(16b) Following a procedure analogous to (13b), boronic ester 16a (3.86 g, 12.8 mmol) was treated with n-butyllithium and dichloromethane. After HPLC purification, the desired α-chloroboronic ester 16b was obtained as a colorless oil (1.57 g, 35%).
(16c) Following a procedure analogous to (2c), α-chloroboronic ester 16b (1.57 g, 4.48 mmol) was converted to the aminoboronic ester hydrochloride 16c by treatment with lithium bis(trimethylsilyl)amide followed by hydrogen chloride. The desired product 16c was obtained as a tan solid (0.63 g, 38%). MS found: $(M+H)^+=332$.
(16d) Following a procedure analogous to (8d), α-aminoboronic ester 16c (36 mg, 0.097 mmol) was coupled to pentapeptide 1h (38 mg, 0.049 mmol) with PyAOP and DIEA. The crude hexapeptide was deprotected with TFA and purified by HPLC to afford the desired hexapeptide 15d. HRMS found: $(M+H)^+=871.4816$.

Example 17

H-Asp-Glu-Val-Val-Pro-(1R)-1-amino-3-(4-phenoxy)phenylpropylboronic acid (+)-pinanediol ester (17a) Following a procedure analogous to (8a), 4-phenoxystyrene (3.92 g, 20.0 mmol) was treated with catecholborane, followed by (+)-pinanediol to provide the desired boronic ester 17a as a colorless oil (2.42 g, 32%).
(17b) Following a procedure analogous to (13b), boronic ester 17a (2.42 g, 6.43 mmol) was treated with n-butyllithium and dichloromethane. After HPLC purification, the desired α-chloroboronic ester 17b was obtained as a colorless oil (0.81 g, 30%).
(17c) Following a procedure analogous to (2c), α-chloroboronic ester 17b (0.74 g, 1.73 mmol) was converted to the aminoboronic ester hydrochloride 17c by treatment with lithium bis(trimethylsilyl)amide followed by hydrogen chloride. The desired product 17c was obtained as a white solid. MS found: $(M+H)^+=406$.
(17d) 1-dimethylaminopropyl-3-ethylcarbodiimide hydrochloride (EDCI) (10 mg, 0.052 mmol) and sodium bicabonate (20 mg, 0.24 mmol) were added in one portion to a solution of α-aminoboronic ester 17c (26 mg, 0.059 mmol), pentapeptide 1h (30 mg, 0.039 mmol), and 1-hydroxy-7-azabenzotriazole (HOAt) (8 mg, 0.059) in dichloromethane (1 mL) and N,N-dimethylformamide (0.2 mL) at 0° C. The reaction mixture was stirred for 1 hr, warmed to rt, and allowed to stir an additional 1 hr. The solvent was removed under reduced pressure, and the residue was purified by chromatography on silica gel (9:1 chloroform/methanol) to afford protected hexapeptide 17d as a white solid (26 mg, 58%). MS found: $(M+Na)^+=1180$.
(17e) Peptide boronic ester 17d (21 mg, 0.018 mmol) was dissolved in a mixture of trifluoroacetic acid (TFA) (1 mL), triisopropylsilane (0.050 mL) and dichloromethane (0.050 mL). The reaction mixture was stirred at rt for 2 h and then was concentrated under reduced pressure. The residue was purified by high performance liquid chromatography (Rainin Dynamax C18 column, gradient from 20 to 70% acetonitrile in water containing 0.1% trifluoroacetic acid over 30 min) to afford hexapeptide 17e. HRMS found: $(M+H)^+=945.5138$.

Example 18

H-Asp-Glu-Val-Val-Pro-(1R)-1-amino-3-(4-isopropyl)phenylpropylboronic acid (+)-pinanediol ester (18a) Following a procedure analogous to (8a), 4-isopropylstyrene (2.00 g, 13.7 mmol) was treated with catecholborane, followed by (+)-pinanediol to provide the desired boronic ester 18a as a colorless solid (2.71 g, 61%).
(18b) Following a procedure analogous to (13b), boronic ester 18a (2.71 g, 8.31 mmol) was treated with n-butyllithium and dichloromethane. After HPLC purification, the desired α-chloroboronic ester 18b was obtained as a colorless oil (1.07 g, 34%).
(18c) Following a procedure analogous to (2c), α-chloroboronic ester 18b (1.07 g, 2.86 mmol) was converted to the aminoboronic ester hydrochloride 18c by treatment with lithium bis(trimethylsilyl)amide followed by hydrogen chloride. The desired product 18c was obtained as a white solid. MS found: $(M+H)^+=356$.
(18d) Following a procedure analogous to (17d), α-aminoboronic ester 18c (26 mg, 0.066 mmol) was coupled to pentapeptide 1h (30 mg, 0.039 mmol) with EDCI, HOAt, and sodium bicarbonate. The crude hexapeptide was deprotected with TFA, following a procedure analogous to (17e), and purified by HPLC to afford the desired hexapeptide 18d. HRMS found: $(M+H)^+=895.5381$.

Example 19

H-Asp-Glu-Val-Val-Pro-(1R)-1-amino-3-(4-cyclohexyl)phenylpropylboronic acid (+)-pinanediol ester (19a) Following a procedure analogous to (8a), 4-cyclohexylstyrene (2.45 g, 13.2 mmol) was treated with catecholborane, followed by (+)-pinanediol to provide the desired boronic ester 19a as a colorless solid (2.78 g, 58%).
(19b) Following a procedure analogous to (13b), boronic ester 19a (3.4 g, 9.3 mmol) was treated with n-butyllithium and dichloromethane. After HPLC purification, the desired α-chloroboronic ester 19b was obtained as a colorless oil (1.08 g, 28%).
(19c) Following a procedure analogous to (2c), α-chloroboronic ester 19b (1.0 g, 2.4 mmol) was converted to the aminoboronic ester hydrochloride 19c by treatment with lithium bis(trimethylsilyl)amide followed by hydrogen chloride. The desired product 19c was obtained as a white solid (290 mg, 26%). MS found: $(M+H)^+=396$.
(19d) Following a procedure analogous to (17d), α-aminoboronic ester 19c (25 mg, 0.058 mmol) was coupled to pentapeptide 1h (32 mg, 0.042 mmol) with EDCI, HOAt, and sodium bicarbonate. The crude hexapeptide was deprotected with TFA, following a procedure analogous to (17e), and purified by HPLC to afford the desired hexapeptide 19d. HRMS found: $(M+H)^+=935.5638$.

Example 20

H-Asp-Glu-Val-Val-Pro-(1R)-1-amino-3-(4-tert-butyl)phenylpropylboronic acid (+)-pinanediol ester (20a) Following a procedure analogous to (8a), 4-t-butylstyrene (3.21 g, 20 mmol) was treated with catecholborane, followed by (+)-pinanediol to provide the desired boronic ester 20a as a dark orange solid (3.57 g, 52%).
(20b) Following a procedure analogous to (13b), boronic ester 20a (3.57 g, 10.5 mmol) was treated with n-butyllithium and dichloromethane. After HPLC purification, the desired α-chloroboronic ester 20b was obtained as a colorless oil (0.68 g, 17%).
(20c) Following a procedure analogous to (2c), α-chloroboronic ester 20b (0.68 g, 1.8 mmol) was converted to the aminoboronic ester hydrochloride 20c by treatment with lithium bis(trimethylsilyl)amide followed by hydrogen chloride. The desired product 20c was obtained as a white solid (70 mg, 10%). MS found: $(M+H)^+=370$.

(20d) Following a procedure analogous to (17d), α-aminoboronic ester 20c (24 mg, 0.059 mmol) was coupled to pentapeptide 1h (30 mg, 0.039 mmol) with EDCI, HOAt, and sodium bicarbonate. The crude hexapeptide was deprotected with TFA, following a procedure analogous to (17e), and purified by HPLC to afford the desired hexapeptide 20d. HRMS found: $(M+H)^+=909.5504$.

Example 21

H-Asp-Glu-Val-Val-Pro-(1R)-1-amino-3-(4-methoxy)phenylpropylboronic acid (+)-pinanediol ester (21a) Following a procedure analogous to (8a), 4-methoxystyrene (2.68 g, 20 mmol) was treated with catecholborane, followed by (+)-pinanediol to provide the desired boronic ester 21a as a colorless oil (4.3 g, 68%).

(21b) Following a procedure analogous to (13b), boronic ester 21a (4.3 g, 13.7 mmol) was treated with n-butyllithium and dichloromethane. After HPLC purification, the desired α-chloroboronic ester 21b was obtained as a colorless oil (1.98 g, 40%).

(21c) Following a procedure analogous to (2c), α-chloroboronic ester 21b (1.98 g, 5.5 mmol) was converted to the aminoboronic ester hydrochloride 21c by treatment with lithium bis(trimethylsilyl)amide followed by hydrogen chloride. The desired product 21c was obtained as a white solid (400 mg, 19%). MS found: $(M+H)^+=344$.

(21d) Following a procedure analogous to (17d), α-aminoboronic ester 21c (22 mg, 0.058 mmol) was coupled to pentapeptide 1h (31 mg, 0.040 mmol) with EDCI, HOAt, and sodium bicarbonate. The crude hexapeptide was deprotected with TFA, following a procedure analogous to (17e), and purified by HPLC to afford the desired hexapeptide 21d. HRMS found: $(M+H)^+=883.4999$.

Example 22

H-Asp-Glu-Val-Val-Pro-(1R)-1-amino-3-(4-chloro)phenylpropylboronic acid (+)-pinanediol ester (22a) Following a procedure analogous to (8a), 4-chlorostyrene (2.77 g, 20 mmol) was treated with catecholborane, followed by (+)-pinanediol to provide the desired boronic ester 22a as a colorless solid (3.22 g, 50%).

(22b) Following a procedure analogous to (13b), boronic ester 22a (3.22 g, 10.1 mmol) was treated with n-butyllithium and dichloromethane. After HPLC purification, the desired α-chloroboronic ester 22b was obtained as a colorless oil (1.32 g, 36%).

(22c) Following a procedure analogous to (2c), α-chloroboronic ester 22b (1.32 g, 3.6 mmol) was converted to the aminoboronic ester hydrochloride 22c by treatment with lithium bis(trimethylsilyl)amide followed by hydrogen chloride. The desired product 22c was obtained as a white solid (700 mg, 51%). MS found: $(M+H)^+=348$.

(22d) Following a procedure analogous to (17d), α-aminoboronic ester 22c (23 mg, 0.060 mmol) was coupled to pentapeptide 1h (30 mg, 0.039 mmol) with EDCI, HOAt, and sodium bicarbonate. The crude hexapeptide was deprotected with TFA, following a procedure analogous to (17e), and purified by HPLC to afford the desired hexapeptide 22d. HRMS found: $(M+H)^+=887.4518$.

Example 23

H-Asp-Glu-Val-Val-Pro-(1R)-1-amino-3-(4-bromo)phenylpropylboronic acid (+)-pinanediol ester (23a) Following a procedure analogous to (8a), 4-bromostyrene (3.66 g, 20 mmol) was treated with catecholborane, followed by (+)-pinanediol to provide the desired boronic ester 23a as a white solid (3.01 g, 42%).

(23b) Following a procedure analogous to (13b), boronic ester 23a (2.67 g, 7.35 mmol) was treated with n-butyllithium and dichloromethane. After HPLC purification, the desired α-chloroboronic ester 23b was obtained as a colorless oil (0.64 g, 21%).

(23c) Following a procedure analogous to (2c), α-chloroboronic ester 23b (0.64 g, 1.56 mmol) was converted to the aminoboronic ester hydrochloride 23c by treatment with lithium bis(trimethylsilyl)amide followed by hydrogen chloride. The desired product 23c was obtained as a white solid (0.71 mg, 100%). MS found: $(M+H)^+=392$.

(23d) Following a procedure analogous to (17d), α-aminoboronic ester 23c (25 mg, 0.058 mmol) was coupled to pentapeptide 1h (33 mg, 0.043 mmol) with EDCI, HOAt, and sodium bicarbonate. The crude hexapeptide was deprotected with TFA, following a procedure analogous to (17e), and purified by HPLC to afford the desired hexapeptide 23d. HRMS found: $(M+H)^+=931.3968$.

Example 24

H-Asp-Glu-Val-Val-Pro-(1R)-1-amino-3-(2-fluoro)phenylpropylboronic acid (+)-pinanediol ester (24a) Following a procedure analogous to (8a), 2-fluorostyrene (2.4 g, 20 mmol) was treated with catecholborane, followed by (+)-pinanediol to provide the desired boronic ester 24a as a colorless oil (1.78 g, 30%).

(24b) Following a procedure analogous to (13b), boronic ester 24a (1.78 g, 5.89 mmol) was treated with n-butyllithium and dichloromethane. After HPLC purification, the desired α-chloroboronic ester 24b was obtained as a colorless oil (1.0 g, 48%).

(24c) Following a procedure analogous to (2c), α-chloroboronic ester 24b (1.00 g, 2.85 mmol) was converted to the aminoboronic ester hydrochloride 24c by treatment with lithium bis(trimethylsilyl)amide followed by hydrogen chloride. The desired product 24c was obtained as a white solid (0.37 mg, 35%). MS found: $(M+H)^+=332$.

(24d) Following a procedure analogous to (17d), α-aminoboronic ester 24c (21 mg, 0.057 mmol) was coupled to pentapeptide 1h (32 mg, 0.042 mmol) with EDCI, HOAt, and sodium bicarbonate. The crude hexapeptide was deprotected with TFA, following a procedure analogous to (17e), and purified by HPLC to afford the desired hexapeptide 24d. HRMS found: $(M+H)^+=871.4793$.

Example 25

H-Asp-Glu-Val-Val-Pro-(1R)-1-amino-3-(3-fluoro)phenylpropylboronic acid (+)-pinanediol ester (25a) Following a procedure analogous to (8a), 3-fluorostyrene (2.44 g, 20 mmol) was treated with catecholborane, followed by (+)-pinanediol to provide the desired boronic ester 25a as a colorless oil (3.4 g, 56%).

(25b) Following a procedure analogous to (13b), boronic ester 25a (1.7 g, 5.6 mmol) was treated with n-butyllithium and dichloromethane. After HPLC purification, the desired α-chloroboronic ester 25b was obtained as a colorless oil (0.865 g, 44%).

(25c) Following a procedure analogous to (2c), α-chloroboronic ester 25b (0.87 g, 2.48 mmol) was converted to the aminoboronic ester hydrochloride 25c by treatment with lithium bis(trimethylsilyl)amide followed by hydrogen chloride. The desired product 25c was obtained as a white solid (0.300 mg, 33%). MS found: $(M+H)^+=332$.

(25d) Following a procedure analogous to (17d), α-aminoboronic ester 25c (21 mg, 0.057 mmol) was coupled to pentapeptide 1h (32 mg, 0.042 mmol) with EDCI, HOAt, and sodium bicarbonate. The crude hexapeptide was deprotected with TFA, following a procedure analogous to (17e), and purified by HPLC to afford the desired hexapeptide 25d. HRMS found: $(M-H)^-=869.4623$.

Example 26

H-Asp-Glu-Val-Val-Pro-(1R)-1-amino-3-(2,6-difluoro)phenylpropylboronic acid (+)-pinanediol ester (26a) Following a procedure analogous to (8a), 2,6-difluorostyrene (3.0 g, 21.4 mmol) was treated with catecholborane, followed by (+)-pinanediol to provide the desired boronic ester 26a as a colorless oil (0.933 g, 14%).
(26b) Following a procedure analogous to (13b), boronic ester 26a (0.93 g, 2.9 mmol) was treated with n-butyllithium and dichloromethane. After HPLC purification, the desired α-chloroboronic ester 26b was obtained as a colorless oil (0.22 g, 20%).
(26c) Following a procedure analogous to (2c), α-chloroboronic ester 26b (0.22 g, 0.60 mmol) was converted to the aminoboronic ester hydrochloride 26c by treatment with lithium bis(trimethylsilyl)amide followed by hydrogen chloride. The desired product 26c was obtained as a white solid (0.150 mg, 65%). MS found: $(M+H)^+=350$.
(26d) Following a procedure analogous to (17d), α-aminoboronic ester 26c (30 mg, 0.081 mmol) was coupled to pentapeptide 1h (36 mg, 0.047 mmol) with EDCI, HOAt, and sodium bicarbonate. The crude hexapeptide was deprotected with TFA, following a procedure analogous to (17e), and purified by HPLC to afford the desired hexapeptide 26d. HRMS found: $(M+H)^+=889.4685$.

Example 27

H-Asp-Glu-Val-Val-Pro-(1R)-1-amino-3-(4-hydroxy)phenylpropylboronic acid (+)-pinanediol ester (27a) Following a procedure analogous to (8a), 4-t-butoxystyrene (3.53 g, 20 mmol) was treated with catecholborane, followed by (+)-pinanediol to provide the desired boronic ester 27a as a colorless oil (2.1 g, 29%).
(27b) Following a procedure analogous to (13b), boronic ester 27a (1.99 g, 5.6 mmol) was treated with n-butyllithium and dichloromethane. After HPLC purification, the desired α-chloroboronic ester 27b was obtained as a colorless oil (0.82 g, 36%).
(27c) Following a procedure analogous to (2c), α-chloroboronic ester 27b (0.82 g, 2.02 mmol) was converted to the aminoboronic ester hydrochloride 27c by treatment with lithium bis(trimethylsilyl)amide followed by hydrogen chloride. The desired product 27c was obtained as a white solid (0.180 mg, 24%). MS found: $(M+H)^+=330$.
(27d) Following a procedure analogous to (17d), α-aminoboronic ester 27c (24 mg, 0.066 mmol) was coupled to pentapeptide 1h (30 mg, 0.039 mmol) with EDCI, HOAt, and sodium bicarbonate. The crude hexapeptide was deprotected with TFA, following a procedure analogous to (17e), and purified by HPLC to afford the desired hexapeptide 27d. HRMS found: $(M+H)^+=869.4838$.

Example 28

Ac-Val-Pro-(1R)-1-amino-3-phenylpropylboronic acid (+)-pinanediol ester (28a) Isobutyl chloroformate (2.9 mL, 22 mmol) was added dropwise to a suspension of N-acetyl-L-valine (3.18 g, 20 mmol) and N-methylmorpholine (2.4 mL, 22 mmol) in dichloromethane (50 mL) at −10° C. The reaction mixture was stirred 30 min. A solution of L-proline benzyl ester (4.83 g, 20 mmol) and N-methylmorpholine (2.4 mL mL, 22 mmol) in dichloromethane (20 mL) was added portionwise. The reaction was stirred for 1 h at −10° C. and then warmed to rt and stirred overnight. The raction mixture was washed with 1 N hydrochloric acid (2×) and brine (1×), dried (MgSO$_4$), and concentrated under reduced pressure. The residue was purified by chromatography on silica gel (9:1 chloroform/methanol) to afford 7.3 g (100%) of a colorless oil. MS found: $(M+H)^+=347.2$.
(28b) A suspension of dipeptide 28a and palladium hydroxide (220 mg, 20 wt. % on charcoal) in methanol (50 mL) and acetic acid (0.5 mL) was hydrogenated (45 psi) for 1.5 h. The reaction mixture was filtered and concentrated under reduced pressure to provide dipeptide 28b (2.44 g, 92%). MS found: $(M+H)^+=257.3$.
(28c) Following a procedure analogous to (17d), α-aminoboronic ester 3c (35 mg, 0.10 mmol) was coupled to dipeptide 28b (26 mg, 0.10 mmol) with EDCI, HOAt, and sodium bicarbonate. The crude tripeptide was purified by HPLC to afford the desired tripeptide boronic ester 28c. HRMS found: $(M+H)^+=552.3598$.

Example 29

Ac-Val-Pro-(1R)-1-amino-3-(4-trifluoromethyl) phenylpropylboronic acid (+)-pinanediol ester
(29a) Following a procedure analogous to (17d), α-aminoboronic ester 14c (42 mg, 0.10 mmol) was coupled to dipeptide 28b (26 mg, 0.10 mmol) with EDCI, HOAt, and sodium bicarbonate. The crude tripeptide was purified by HPLC to afford the desired tripeptide boronic ester 29a. HRMS found: $(M+H)^+=620.3486$.

Example 30

Ac-Val-Pro-(1R)-1-amino-3-(4-phenoxy) phenylpropylboronic acid (+)-pinanediol ester
(30a) Following a procedure analogous to (17d), α-aminoboronic ester 17c (44 mg, 0.10 mmol) was coupled to dipeptide 28b (26 mg, 0.10 mmol) with EDCI, HOAt, and sodium bicarbonate. The crude tripeptide was purified by HPLC to afford the desired tripeptide boronic ester 30a. HRMS found: $(M+H)^+=644.3886$.

Example 31

Ac-Val-Pro-(1R)-1-amino-3-(4-hydroxy) phenylpropylboronic acid (+)-pinanediol ester
(31a) Following a procedure analogous to (17d), α-aminoboronic ester 27c (154 mg, 0.42 mmol) was coupled to dipeptide 28b (101 mg, 0.39 mmol) with EDCI, HOAt, and sodium bicarbonate. The crude tripeptide was purified by HPLC to afford the desired tripeptide boronic ester 31a (56 mg, 25%). HRMS found: $(M+H)^+=568.3563$.

Example 32

Ac-Val-Pro-(1R)-1-amino-3-(4-(4-methoxyphenoxy) phenyl) propylboronic acid (+)-pinanediol ester
(32a) A solution of tripeptide boronic ester 31a (20 mg, 0.035 mmol), 4-methoxyphenylboronic acid (32 mg, 0.21 mmol), copper(II) acetate (27 mg, 0.15 mmol), pyridine (0.016 mL, 0.19 mmol), and morpholine (0.011 mL, 0.100) in dichloromethane (1 mL) over molecular sieves (4 Å, oven dried) was stirred at rt overnight. The reaction mixture was concentrated under reduced pressure and the residue was purified by chromatography on silica gel (9:0.5 chloroform/methanol) followed by HPLC to afford the desired tripeptide boronic ester 32a. HRMS found: $(M+H)^+=674.3947$.

Example 33

Ac-Val-Pro-(1R)-1-amino-3-(4-(4-methylphenoxy) phenyl) propylboronic acid (+)-pinanediol ester (33a) A solution of tripeptide boronic ester 31a (20 mg, 0.035 mmol), 4-methylphenylboronic acid (26 mg, 0.19 mmol), copper(II) acetate (27 mg, 0.15 mmol), pyridine (0.016 mL, 0.19 mmol), and morpholine (0.011 mL, 0.100) in dichloromethane (1 mL) over molecular sieves (4 Å, oven dried) was stirred at rt overnight. The reaction mixture was concentrated under reduced pressure and the residue was purified by chromatography on silica gel (9:0.5 chloroform/methanol) followed by HPLC to afford the desired tripeptide boronic ester 33a. HRMS found: $(M+H)^+=658.4051$.

Example 34

(2-pyrazinecarbonyl)-Val-Val-Hyp(OBzl)-(1R)-1-amino-3-(4-trifluoromethyl)phenylpropylboronic acid (+)-pinanediol ester (34a) Following a procedure analogous to (17d), α-aminoboronic ester 14c (36 mg, 0.086 mmol) was coupled to thetripeptide (2-pyrazinecarbonyl)-Val-Val-Hyp(OBn)-OH (prepared in a manner analogous to example 1) (30 mg, 0.057 mmol) with EDCI, HOAt, and sodium bicarbonate. The crude material was purified by HPLC to afford the desired tetrapeptide 34a (23 mg, 45%). HRMS found: $(M+H)^+=889.4665$.

Example 35

H-Asp-Glu-Val-Val-Pro-(1R)-1-aminohexylboronic acid (+)-pinanediol ester (35a) Using a procedure analogous to (3a), n-pentylmagnesium bromide (2M solution in ether, 13.3 ml, 26.6 mmol) was reacted with triisopropyl borate and (+)-pinanediol. Silica gel chromatography (9:1 hexane/ethyl acetate) afforded the desired boronic ester 35a as a pale yellow oil (3.33 g, 50%).

(35b) Using a procedure analogous to (2b), boronic ester 35a (3.3 g, 13.2 mmol) was treated with n-butyllithium and dichloromethane in tetrahydrofuran to provide the desired α-chloroboronic ester 35b as a clear oil (2.5 g, 63%) after chromatography on silica gel.

(35c) Following a procedure analogous to (2c), α-chloroboronic ester 35b (2.5 g, 8.37 mmol) was converted to the aminoboronic ester hydrochloride 35c by treatment with lithium bis(trimethylsilyl)amide followed by hydrogen chloride. The desired product 35c (0.57 g, 22%) was obtained as a colorless oil. MS found: $(M+H)^+=280.2$.

(35d) Following a procedure analogous to (2d), α-aminoboronic ester (35c) (18 mg, 0.056 mmol) was coupled to pentapeptide 1h (29 mg, 0.038 mmol) with PyAOP and DIEA and purified by HPLC to afford the desired hexapeptide 35d (9 mg, 23%). MS found: $(M+H)^+=1031.7$.

(35e) Following a procedure analogous to (2e), the hexapeptide 35d (4 mg, 0.004 mmol) was deprotected with TFA and triisopropylsilane and purified by HPLC to afford the desired hexapeptide 35e as a white solid. HRMS found: $(M+H)^+=819.5$.

Example 36

H-Asp-Glu-Val-Val-Pro-(1R)-1-amino-5-methylhexylboronic acid (+)-pinanediol ester (36a) Using a procedure analogous to (3a), 4-methyl-3-pentenylmagnesium bromide (18.4 mmol) was reacted with triisopropyl borate and (+)-pinanediol. Silica gel chromatography (9:1 hexane/ethyl acetate) afforded the desired boronic ester 36a as a pale yellow oil (2.4 g, 50%).

(36b) Using a procedure analogous to (2b), boronic ester 36a (0.6 g, 13.2 mmol) was treated with n-butyllithium and dichloromethane in tetrahydrofuran to provide the desired α-chloroboronic ester 36b as a clear oil (0.58 g, 82%) after chromatography on silica gel.

(36c) Following a procedure analogous to (2c), α-chloroboronic ester 36b (252 mg, 0.81 mmol) was converted to the aminoboronic ester hydrochloride 36c by treatment with lithium bis(trimethylsilyl)amide followed by hydrogen chloride. The desired product 36c (0.26 g, 99%) was obtained as a colorless solid. HRMS found: $(M+H)^+=292.2$.

(36d) Following a procedure analogous to (2d), α-aminoboronic ester (36c) (80 mg, 0.244 mmol) was coupled to pentapeptide 1h (125 mg, 0.163 mmol) with PyAOP and DIEA and purified by HPLC to afford the desired hexapeptide 36d (135 mg, 79%). HRMS found: $(M+H)^+=1043.6$.

(36e) A solution of hexapeptide 36d (52 mg, 0.050 mmol) in methanol (2 mL) containing hydrochloric acid (1 drop) was hydrogenated (1 atm) over 20% palladium on carbon at room temperature overnight. The solution was filtered to yield the desired hexapeptide (50 mg, 96%). MS found: $(M+H)^+=1045.9$.

(36f) Following a procedure analogous to (2e), the hexapeptide 36e (50 mg, 0.048 mmol) was deprotected with TFA and triisopropylsilane and purified by HPLC to afford the desired hexapeptide 36e as a white solid (3 mg, 7.5%). MS found: $(M+H)^+=833.5$.

Example 37

H-Asp-Glu-Val-Val-Pro-(1R)-1-aminoheptylboronic acid (+)-pinanediol ester (37a) Using a procedure analogous to (3a), n-hexylmagnesium bromide (2M solution in ether, 32 ml, 64 mmol) was reacted with triisopropyl borate and (+)-pinanediol. Silica gel chromatography (9:1 hexane/ethyl acetate) afforded the desired boronic ester 37a as a pale yellow oil (10.6 g, 75%).

(37b) Using a procedure analogous to (2b), boronic ester 37a (10.6 g, 40.1 mmol) was treated with n-butyllithium and dichloromethane in tetrahydrofuran to provide the desired α-chloroboronic ester 37b as a clear oil (12 g, 95%) after chromatography on silica gel.

(37c) Following a procedure analogous to (2c), α-chloroboronic ester 37b (12 g, 38 mmol) was converted to the aminoboronic ester hydrochloride 37c by treatment with lithium bis(trimethylsilyl)amide followed by hydrogen chloride. The desired product 37c was obtained as a colorless oil.

(37d) Following a procedure analogous to (2d), α-aminoboronic ester (37c) (86 mg, 0.26 mmol) was coupled to pentapeptide 1h (50 mg, 0.065 mmol) with PyAOP and DIEA and purified by HPLC to afford the desired hexapeptide 37d (7 mg, 10%).

(37e) Following a procedure analogous to (2e), the hexapeptide 37d (7 mg, 0.007 mmol) was deprotected with TFA and triisopropylsilane and purified by HPLC to afford the desired hexapeptide 37e as a white solid. MS found: $(M+H)^+=833.6$.

Example 38

H-Asp-Glu-Val-Val-Pro-(1R)-1-amino-4-cyclobutylbutylboronic acid (+)-pinanediol ester (38a) A solution of cyclobutylbromide (5 g, 37 mmol) in ether (15 mL) was added slowly dropwise to a suspension of magnesium (1.8 g, 74 mmol) and iodine (1 granule) in ether (15 mL). The reaction mixture was then refluxed for 2 h. The solution was cooled to RT and then added slowly dropwise to a solution of allyl bromide (3.2 mL, 37 mmol) in ether (10 mL) at 0° C. The reaction mixture was allowed to warm to RT and stir overnight. The solution was diluted with ether and washed with saturated ammonium chloride solution. The solvent was removed by distillation at atmospheric pressure, and the desired olefin 38a was isolated by vacuum distillation as a colorless oil (1.65 g, 46%). $^{13}$C NMR δ (ppm) 137.0, 114.7, 41.0, 35.2, 27.8, 18.4.

(38b) Using a procedure analogous to (8a), olefin 38a (1.6 g, 16.5 mmol) was reacted with catecholborane and then (+)-pinanediol. After chromatography on silica gel (10:1 hexane/ethyl acetate), the desired boronic ester (38b) was isolated as a colorless oil (3.2 g, 70%).

(38c) Using a procedure analogous to (2b), boronic ester 38b (1 g, 3.6 mmol) was treated with n-butyllithium and dichloromethane in tetrahydrofuran to provide the desired α-chloroboronic ester 38c as a clear oil (1.05 g, 80%) after chromatography on silica gel.

(38d) Following a procedure analogous to (2c), α-chloroboronic ester 38c (0.5 g, 1.54 mmol) was converted to the aminoboronic ester hydrochloride 38d by treatment with lithium bis(trimethylsilyl)amide followed by hydrogen chloride. The desired product 38d (0.5 g, 94%) was obtained as a colorless oil. MS found: $(M+H)^+=306.3$.

(38e) Following a procedure analogous to (2d), α-aminoboronic ester (38d) (20 mg, 0.058 mmol) was coupled to pentapeptide 1h (30 mg, 0.039 mmol) with PyAOP and DIEA and purified by HPLC to afford the desired hexapeptide 38e. MS found: $(M+H)^+=1057.9$.

(38f) Following a procedure analogous to (2e), the hexapeptide 38e was deprotected with TFA and triisopropylsilane and purified by HPLC to afford the desired hexapeptide 38f as a white solid. MS found: $(M+H)^+=845.1$.

Example 39

H-Asp-Glu-Val-Val-Pro-(1R)-1-amino-5-ethylheptylboronic acid (+)-pinanediol ester (39a) Using a procedure analogous to (38a) 3-bromopropane was reacted with magnesium and then allyl bromide. The desired olefin 39a was isolated by vacuum distillation as a colorless oil (0.84 g, 14%).

(39b) Using a procedure analogous to (8a), olefin 39a (0.84 g, 7.5 mmol) was reacted with catecholborane and then (+)-pinanediol. After chromatography on silica gel (10:1 hexane/ethyl acetate), the desired boronic ester (39b) was isolated as a colorless oil (0.48 g, 87%).

(39c) Using a procedure analogous to (2b), boronic ester 39b (0.48 g, 1.6 mmol) was treated with n-butyllithium and dichloromethane in tetrahydrofuran to provide the desired α-chloroboronic ester 39c as a clear oil (0.186 g, 66%) after chromatography on silica gel.

(39d) Following a procedure analogous to (2c), α-chloroboronic ester 39c (0.5 g, 1.54 mmol) was converted to the aminoboronic ester hydrochloride 39d by treatment with lithium bis(trimethylsilyl)amide followed by hydrogen chloride. The desired product 39d (0.15 g, 77%) was obtained as a colorless oil.

(39e) Following a procedure analogous to (2d), α-aminoboronic ester (39d) (21 mg, 0.058 mmol) was coupled to pentapeptide 1h (30 mg, 0.039 mmol) with PyAOP and DIEA and purified by HPLC to afford the desired hexapeptide 39e. MS found: $(M+H)^+=1073.9$.

(39f) Following a procedure analogous to (2e), the hexapeptide 39e was deprotected with TFA and triisopropylsilane and purified by HPLC to afford the desired hexapeptide 39f as a white solid. MS found: $(M+H)^+=861.6$.

Table 1 provides representative Examples of the compounds of Formula (I) of the present invention.

TABLE 1

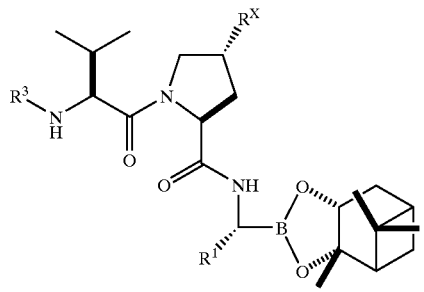

| Ex. | $R^1$ | $R^3$ | $R^X$ | MS $(M + H)^+$ |
|---|---|---|---|---|
| 2 | phenyl | H-Asp-Glu-Val- | H | 825.5 |
| 3 | 2-phenylethyl | H-Asp-Glu-Val- | H | 853.5 |
| 4 | 3-phenylpropyl | H-Asp-Glu-Val- | H | 867.5 |
| 5 | 4-phenylbutyl | H-Asp-Glu-Val- | H | 881.5 |
| 7 | 2-(2-naphthyl)ethyl | H-Asp-Glu-Val- | H | 903.5 |
| 8 | 2-(2-methylphenyl)ethyl | H-Asp-Glu-Val- | H | 867.5 |
| 9 | 2-(3-methylphenyl)ethyl | H-Asp-Glu-Val- | H | 867.5 |
| 10 | 2-(4-methylphenyl)ethyl | H-Asp-Glu-Val- | H | 867.5 |
| 11 | 2-(1,1'-biphenyl)-4-ylethyl | H-Asp-Glu-Val- | H | 929.5 |
| 12 | 2-(2,5-dimethylphenyl)ethyl | H-Asp-Glu-Val- | H | 881.5 |
| 13 | 2-(2,4-dimethylphenyl)ethyl | H-Asp-G1u-Val- | H | 881.5 |
| 14 | 2-(4-trifluoromethylphenyl)ethyl | H-Asp-Glu-Val- | H | 921.5 |
| 15 | 2-(3-trifluoromethylphenyl)ethyl | H-Asp-Glu-Val- | H | 921.5 |
| 16 | 2-(4-fluorophenyl)ethyl | H-Asp-Glu-Val- | H | 871.5 |
| 17 | 2-(4-phenoxyphenyl)ethyl | H-Asp-Glu-Val- | H | 945.5 |
| 18 | 2-(4-isopropylphenyl)ethyl | H-Asp-Glu-Val- | H | 895.5 |
| 19 | 2-(4-cyclohexylphenyl)-ethyl | H-Asp-Glu-Val- | H | 935.6 |
| 20 | 2-(4-tert-butylphenyl)ethyl | H-Asp-Glu-Val- | H | 909.6 |
| 21 | 2-(4-methoxyphenyl)ethyl | H-Asp-Glu-Val- | H | 883.5 |
| 22 | 2-(4-chlorophenyl)ethyl | H-Asp-Glu-Val- | H | 887.4 |
| 23 | 2-(4-bromophenyl)ethyl | H-Asp-Glu-Val- | H | 931.4 |
| 24 | 2-(2-fluorophenyl)ethyl | H-Asp-Glu-Val- | H | 871.5 |
| 25 | 2-(3-fluorophenyl)ethyl | H-Asp-Glu-Val- | H | 869.5 |
| 26 | 2-(2,6-difluorophenyl)ethyl | H-Asp-Glu-Val- | H | 889.5 |
| 27 | 2-(4-hydroxyphenyl)ethyl | H-Asp-Glu-Val- | H | 869.5 |
| 28 | 2-phenylethyl | Ac- | H | 552.4 |
| 29 | 2-(4-trifluoromethylphenyl)ethyl | Ac- | H | 620.3 |
| 30 | 2-(4-phenoxyphenyl)ethyl | Ac- | H | 644.4 |
| 31 | 2-(4-hydroxyphenyl)ethyl | Ac- | H | 568.4 |
| 32 | 2-(4-(4-methoxyphenoxy)-phenyl)ethyl | Ac- | H | 674.4 |
| 33 | 2-(4-(4-methylphenoxy)-phenyl)ethyl | Ac- | H | 658.4 |
| 34 | 2-(4-trifluoromethylphenyl)ethyl | (2-pyrazine-carbonyl)-Val- | OBzl | 889.5 |
| 35 | pentyl | H-Asp-Glu-Val- | H | 819.5 |
| 36 | 4-methylpentyl | H-Asp-Glu-Val- | H | 833.5 |
| 37 | hexyl | H-Asp-Glu-Val- | H | 833.6 |
| 38 | 3-cyclobutylpropyl | H-Asp-Glu-Val- | H | 845.1 |
| 39 | 4-ethylhexyl | H-Asp-Glu-Val- | H | 861.6 |

Utility

The compounds of Formula (I) are expected to inhibit the activity of Hepatitis C Virus NS3 protease. The NS3 protease inhibition is demonstrated using assays for NS3 protease activity, for example, using the assay described below for assaying inhibitors of NS3 protease. Thus, the compounds of Formula (I) are potentially useful in the cure and prevention of HCV infections. Additionally, compounds of the present invention demonstrate unexpected inhibitory selectivity of HCV NS3 protease over elastase inhibition. Additionally, it is expected that compounds of the present invention may show unexpected inhibitory selectivity of HCV NS3 protease over chymotrypsin inhibition.

Biological Activity

Expression and Purification of NS3 Protease

The plasmid cf1SODp600, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (serving as a expression tag) and a 15 amino acid His tag MRGSHHHHHHMGAQH. The NS3 protease constructs were cloned in the bacterial expression vector under the control of the T7 promoter and transformed in E. coli BL 21 (DE3) cells. Expression of the NS3 protease was obtained by addition of 1 mM IPTG and cells were grown for an additional 3 h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 ml/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/ml and cell lysate was incubated at 4° C. for 20 min. After centrifugation at 18,000 rpm for 30 min at 4° C. supernatant was applied on SP Sepharose column (Pharmacia), previously equilibrated at a flow rate 3 ml/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 ml/min, the column was then washed with a buffer A at a flow rate 2 ml/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 ml/min. Enzyme was eluted by applying 20 column volumes of a linear 0.1–0.5 M NaCl gradient. Based on SDS-PAGE analysis as well as HPLC analysis and active site titration, the purity of the HCV NS3 1a protease was greater than 95%. The enzyme was stored at −70° C. and diluted just prior to use.

NS3 Protease Enzyme Assays

Concentrations of protease were determined in the absence of NS4a by using the peptide ester substrate Ac-DED(Edans)EEAbuψ[COO]ASK(Dabcyl)-NH$_2$ (Taliani et al. *Anal. Biochem.* 240, 60–67, 1996.) and the inhibitor, H-Asp-Glu-Val-Val-Pro-boroAlg-OH and by using tight binding reaction conditions (Bieth, *Methods Enzymol.* 248, 59–85, 1995). Best data was obtained for an enzyme level of 50 nM. Alternately, protease (63 μg/ml) was allowed to react with 3 μM NS4a, 0.10 mM Ac-Glu-Glu-Ala-Cys-pNA, and varying level of H-Asp-Glu-Val-Val-Pro-boroAlg-OH (0–6 μM). Concentrations of protease were determined from linear plots of Activity vs. [inhibitor]. Molar concentrations of proteases were determined from the x-intercept. $K_m$ values were determined measuring the rate of hydrolysis of the ester substrate over a range of concentrations from 5.0 to 100 μM in the presence of 3 μM KKNS4a (KKGSVVIVGRIVLSGKPAIIPKK). Assay were run at 25° C., by incubating ~1 nM enzyme with NS4a for 5 min in 148 μl of buffer (50 mM Tri buffer, pH 7.0, 50% glycerol, 2% Chaps, and 5.0 mM DTT. Substrate (2.0 μl) in buffer was added and the reaction was allowed to proceed for 15 min. Reactions were quenched by adding 3.0 μL of 10% TFA, and the levels of hydrolysis were determined by HPLC. Aliquots (50 μL) were injected on the HPLC and linear gradients from 90% water, 10% acetonitrile and 0.1% TFA to 10% water, 90% acetonitrile and 0.1% TFA were run at a flow rate of 1.0 mL/min over a period of 30 min. HPLCs were run on a HP1090 using a Rainin 4.6×250 mm C18 column (cat # 83-201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 μM sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 μM was used for all fluorogenic assays run on the spectrometer.

NS3 Protease Inhibitor Evaluation In vitro

Inhibitor effectiveness was determined by measuring enzyme activity both in the presence and absence of inhibitor. Velocities were fit to the equation for competitive inhibition for individual reactions of inhibitors with the enzyme using $$v_i/v_o = [K_m(1+I/K_i)+S]/[K_m+S].$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the $IC_{50}$ and $K_i$'s are comparable measures of inhibitor effectiveness.

Compounds tested in the above assay are considered to be active if they exhibit a $K_i$ of ≦50 μM. Preferred compounds of the present invention have $K_i$'s of ≦1 μM. More preferred compounds of the present invention have $K_i$'s of ≦0.1 μM. Even more preferred compounds of the present invention have $K_i$'s of ≦0.01 μM. Still more preferred compounds of the present invention have $K_i$'s of ≦0.001 μM Using the methodology described above, compounds of the present invention were found to exhibit a $K_i$ of ≦50 μM, thereby confirming the utility of the compounds of the present invention as effective HCV NS3 protease inhibitors.

NS3 Protease Inhibitor Evaluation of in Cell Assay.

The following method was devised to assess inhibitory action of test compounds on the HCV NS3 protease in cultured cells. Because it is not presently possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease. When installed in cultured cells by one of a variety of standard methods, the substrate plasmid produces a stable polypeptide of approximately 50 KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The general organization of the two plasmids is disclosed in a PCT application PCT/US00/18655. The disclosure of which is hereby incorporated by reference. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 µL of 1% sodium dodecyl sulfate in 0.10 M Tris-HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Inhibitory Selectivity

In addition to the inhibitory activity against HCV NS3 protease exhibited by the compounds of Formula (1), Applicants have discovered unexpected benefit of selectivity over inhibition of elastase and/or chymotrypsin proteases. Most HCV NS3 protease inhibitors reported do not show selectivity over elastase. Selectivity of HCV NS3 over elastase can be calculated by dividing $IC_{50}$ (elastase) over $IC_{50}$ (HCV NS3). Similarily, selectivity of HCV NS3 over chymotrypsin can be calculated by dividing $IC_{50}$ (chymotrypsin) over $IC_{50}$ (HCV NS3).

Inhibition Evaluation of Elastase Protease

Human neutrophil elastase was obtained from ART Biochemicals, Athens, Ga. Stock solutions of lyophilized enzyme (1 mg/ml) were prepared in PBS buffer containing 10% glycerol and stored at –20° C. Human neutrophil elastase was assayed with the Meo-Suc-Ala-Ala-Pro-Val-p-nitroanilide (Sigma) as a substrate (C. Kettner and A. Shenvi, 1984). The hydrolysis of substrate was monitored at 405 nm on a Hewlett-Packard spectrophotometer. Kinetic parameters were determined in PBS buffer at room temperature with concentration of DMSO did not exceed 2%.

Representative compounds of the present invention have been tested using the assay discussed herein for selectivity over elastase. Table 2 shows unexpected result of inhibitory selectivity of HCV NS3 protease over elastase exihibited by the compounds of the instant invention. In Table 2, NA indicates that inhibition of elastase of the compound was not tested.

TABLE 2

| Ex. | Selectivity of HCV NS3 vs. elastase |
|---|---|
| 2 | NA |
| 3 | >10 |
| 4 | NA |
| 5 | 9 |
| 7 | NA |
| 8 | NA |
| 9 | >10 |
| 10 | >10 |
| 11 | >10 |
| 12 | NA |
| 13 | NA |
| 14 | >10 |
| 15 | NA |
| 16 | >10 |
| 17 | >10 |
| 18 | >10 |
| 19 | >10 |
| 20 | >10 |
| 21 | >10 |
| 22 | >10 |
| 23 | >10 |
| 24 | NA |
| 25 | NA |
| 26 | NA |
| 27 | >10 |
| 28 | NA |
| 29 | NA |
| 30 | NA |
| 31 | NA |
| 32 | NA |
| 33 | NA |
| 34 | 7 |
| 35 | NA |
| 36 | >10 |
| 37 | NA |
| 38 | NA |
| 39 | NA |

Inhibition Evaluation of Chymotryosin Protease

Human pancreatic chymotrypsin was obtained from Calbiochem, San Diego, Calif. Stock solutions of (20 µM) were prepared in 1 mM hydrochloric acid and stored at –20° C. Human pancreatic chymotrypsin was assayed with the Suc-Ala-Ala-Pro-Phe-p-nitroanilide (Calbiochem cathepsin G substrate #219407) as a substrate. The hydrolysis of substrate was monitored at 405 nm on a Titertek Multiscan MCC/340 plate reader. Kinetic parameters were determined in 0.1 M Tris, pH 7.8, 10 mM $CaCl_2$ buffer at room temperature with a concentration of DMSO that did not exceed 2%.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

Dosage and Formulation

The HCV protease inhibitor compounds of this invention can be administered as treatment for the control or prevention of hepatitis C virus infections by any means that produces contact of the active agent with the agent's site of action, i.e., the NS3 protease, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

I claim:

1. The compound (2-pyrazinecarbonyl)-Val-Val-Hyp (OBn)-(1R)-1-amino-3-(4-trifluoromethyl) phenylpropylboronic acid (+)-pinanediol ester, and pharmaceutically acceptable salts and solvates thereof.

* * * * *

UNITED STATES PATENT AND TRADEMARK OFFICE
CERTIFICATE OF CORRECTION

PATENT NO. : 6,846,806 B2
DATED : January 25, 2005
INVENTOR(S) : E. Scott Priestley It is certified that error appears in the above-identified patent and that said Letters Patent is hereby corrected as shown below:

<u>Title page, Item [54] and Column 1, line 2,</u>
Title, "PROTEIN" should be -- PROTEASE --.

Signed and Sealed this

Twenty-fourth Day of May, 2005

JON W. DUDAS
*Director of the United States Patent and Trademark Office*